US009873875B2

(12) United States Patent
Rossi et al.

(10) Patent No.: US 9,873,875 B2
(45) Date of Patent: *Jan. 23, 2018

(54) METHODS AND COMPOSITIONS FOR THE SPECIFIC INHIBITION OF GENE EXPRESSION BY DOUBLE-STRANDED RNA

(71) Applicants: CITY OF HOPE, Duarte, CA (US); INTEGRATED DNA TECHNOLOGIES, INC., Coralville, IA (US)

(72) Inventors: John J Rossi, Azusa, CA (US); Mark A. Behlke, Coralville, IA (US); Dongho Kim, Beverly Hills, CA (US)

(73) Assignees: CITY OF HOPE, Duarte, CA (US); INTEGRATED DNA TECHNOLOGIES, INC., Coralville, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/259,174

(22) Filed: Sep. 8, 2016

(65) Prior Publication Data

US 2016/0376590 A1 Dec. 29, 2016

Related U.S. Application Data

(60) Continuation of application No. 14/537,578, filed on Nov. 10, 2014, now Pat. No. 9,441,227, which is a continuation of application No. 13/491,937, filed on Jun. 8, 2012, now Pat. No. 8,883,996, which is a continuation of application No. 12/143,002, filed on Jun. 20, 2008, now abandoned, which is a division of application No. 11/797,216, filed on May 1, 2007, now abandoned.

(51) Int. Cl.
C07H 21/04 (2006.01)
C12N 15/113 (2010.01)
C12N 15/11 (2006.01)

(52) U.S. Cl.
CPC .......... *C12N 15/113* (2013.01); *C12N 15/111* (2013.01); *C12N 2310/14* (2013.01); *C12N 2310/33* (2013.01); *C12N 2310/53* (2013.01); *C12N 2310/533* (2013.01); *C12N 2320/35* (2013.01); *C12N 2320/51* (2013.01)

(58) Field of Classification Search
CPC .................................................. C07H 21/04
See application file for complete search history.

(56) References Cited

U.S. PATENT DOCUMENTS

| 5,624,803 | A  | 4/1997  | Noonberg et al. |
|-----------|----|---------|-----------------|
| 5,898,031 | A  | 4/1999  | Crooke          |
| 6,107,094 | A  | 8/2000  | Crooke          |
| 6,506,559 | B1 | 1/2003  | Fire et al.     |
| 7,452,987 | B2 | 11/2008 | Giese et al.    |
| 7,595,306 | B2 | 9/2009  | Bumcrot         |
| 2002/0086356 | A1 | 7/2002 | Tuschl et al. |
| 2002/0114784 | A1 | 8/2002 | Li et al. |
| 2003/0108923 | A1 | 6/2003 | Tuschl et al. |
| 2003/0190654 | A1 | 10/2003 | Heidenreich et al. |
| 2004/0002077 | A1 | 1/2004 | Taira et al. |
| 2004/0014956 | A1 | 1/2004 | Woolf et al. |
| 2004/0018176 | A1 | 1/2004 | Tolentino et al. |
| 2004/0023390 | A1 | 2/2004 | Davidson et al. |
| 2004/0147476 | A1 | 7/2004 | Satishchandran et al. |
| 2004/0152117 | A1 | 8/2004 | Giordano et al. |
| 2004/0175703 | A1 | 9/2004 | Kreutzer et al. |
| 2004/0180438 | A1 | 9/2004 | Pachuk |
| 2004/0192626 | A1 | 9/2004 | McSwiggen et al. |
| 2004/0203145 | A1 | 10/2004 | Zamore et al. |
| 2004/0224405 | A1 | 11/2004 | Leake et al. |
| 2004/0248299 | A1 | 12/2004 | Jayasena et al. |
| 2004/0259247 | A1 | 12/2004 | Tuschl et al. |
| 2005/0020525 | A1 | 1/2005 | McSwiggen et al. |
| 2005/0026160 | A1 | 2/2005 | Allerson et al. |
| 2005/0032733 | A1 | 2/2005 | McSwiggen et al. |

(Continued)

FOREIGN PATENT DOCUMENTS

WO 0104313 A1 1/2001
WO 2002004321 A2 6/2002

(Continued)

OTHER PUBLICATIONS

JP Appln No. 2007-504009, English translation of Office Action dated Aug. 9, 2012, 5 pages.
WO 2005/068630 (Jul. 28, 2005) with excerpt translation, 78 pages.
Elbashir, S.M., "Functional anatomy of siRNAs for mediating efficient RNAi in *Drosophila rnelanogaster* embryo lysate," The EMBO Journal, vol. 20, No. 23, pp. 6877-8888, 2001.
Tuschl, T. et al., "Small interfering RNAs: A revolutionary tool for the analysis of gene function and gene therapy," Molecular Interventions, American Society for Pharmacology and Experimental Therapeutics, Bethesda, MD, US, vol. 2, No. 3, Jun. 2002, pp. 158-167.
European Search Report dated Sep. 21, 2012; Reference: OWK/G28594EP-D1, Application No./Patent No. 12174021.1-2405; Applicant: City of Hope, 7 pages.

(Continued)

*Primary Examiner* — Kimberly Chong
(74) *Attorney, Agent, or Firm* — Rothwell, Figg, Ernst & Manbeck, P.C.

(57) ABSTRACT

The invention is directed to compositions and methods for selectively reducing the expression of a gene product from a desired target gene in a cell, as well as for treating diseases caused by the expression of the gene. More particularly, the invention is directed to compositions that contain double stranded RNA ("dsRNA"), and methods for preparing them, that are capable of reducing the expression of target genes in eukaryotic cells. The dsRNA has a first oligonucleotide sequence that is between 25 and about 30 nucleotides in length and a second oligonucleotide sequence that anneals to the first sequence under biological conditions. In addition, a region of one of the sequences of the dsRNA having a sequence length of at least 19 nucleotides is sufficiently complementary to a nucleotide sequence of the RNA produced from the target gene to trigger the destruction of the target RNA by the RNAi machinery.

1 Claim, 31 Drawing Sheets

(56) References Cited

U.S. PATENT DOCUMENTS

| | | |
|---|---|---|
| 2005/0039224 A1 | 2/2005 | Pachuk et al. |
| 2005/0042646 A1 | 2/2005 | Davidson et al. |
| 2005/0048647 A1 | 3/2005 | Taira et al. |
| 2005/0186586 A1 | 8/2005 | Zamore et al. |
| 2005/0233329 A1 | 10/2005 | McSwiggen et al. |
| 2005/0239728 A1 | 10/2005 | Pachuk et al. |
| 2005/0244858 A1 | 11/2005 | Rossi et al. |
| 2005/0277610 A1 | 12/2005 | Rossi et al. |
| 2005/0282186 A1 | 12/2005 | Haeberli et al. |
| 2006/0009402 A1 | 1/2006 | Zamore et al. |
| 2006/0009409 A1 | 1/2006 | Woolf et al. |
| 2006/0135456 A1 | 6/2006 | Hannon et al. |
| 2006/0217331 A1 | 9/2006 | Vargeese et al. |
| 2006/0287267 A1 | 12/2006 | Vaish et al. |
| 2007/0265220 A1 | 11/2007 | Rossi et al. |
| 2008/0146788 A1 | 6/2008 | Bhat et al. |
| 2009/0018321 A1 | 1/2009 | Rossi et al. |
| 2009/0029466 A1 | 1/2009 | Rossi et al. |
| 2009/0029936 A1 | 1/2009 | Rossi et al. |
| 2009/0035854 A1 | 2/2009 | Rossi et al. |
| 2009/0036661 A1 | 2/2009 | Rossi et al. |
| 2009/0043083 A1 | 2/2009 | Rossi et al. |
| 2009/0325181 A1 | 12/2009 | Rossi et al. |
| 2009/0325285 A1 | 12/2009 | Rossi et al. |
| 2009/0325286 A1 | 12/2009 | Rossi et al. |
| 2009/0326046 A1 | 12/2009 | Rossi et al. |
| 2010/0003758 A1 | 1/2010 | Rossi et al. |
| 2010/0004317 A1 | 1/2010 | Rossi et al. |
| 2010/0004318 A1 | 1/2010 | Rossi et al. |
| 2010/0004434 A1 | 1/2010 | Rossi et al. |
| 2010/0004435 A1 | 1/2010 | Rossi et al. |
| 2010/0004436 A1 | 1/2010 | Rossi et al. |
| 2010/0069465 A1 | 3/2010 | Rossi et al. |

FOREIGN PATENT DOCUMENTS

| | | |
|---|---|---|
| WO | 02/055693 A2 | 7/2002 |
| WO | 03/079757 A2 | 10/2003 |
| WO | 2004011647 A1 | 2/2004 |
| WO | 2004015107 A2 | 2/2004 |
| WO | 2004027030 A2 | 4/2004 |
| WO | 2004029215 A2 | 4/2004 |
| WO | 2004035765 A2 | 4/2004 |
| WO | 2004065600 A2 | 8/2004 |
| WO | 2004076629 A2 | 9/2004 |
| WO | 2005014806 A2 | 2/2005 |
| WO | 2005019453 A2 | 3/2005 |
| WO | 2005040388 A2 | 5/2005 |
| WO | 2005/120230 A2 | 12/2005 |
| WO | 2005121370 A2 | 12/2005 |
| WO | 2006035434 A2 | 4/2006 |

OTHER PUBLICATIONS

English translation of First Office Action in corresponding Chinese Patent Application No. 200880021385.2, Application dated Apr. 11, 2008, 19 pages.

Amarzguioui, M. et al., "Approaches for Chemically Synthesized siRNA and Vector-Mediated RNAi," FEBS Letters, 2005, vol. 579, No. 26, pp. 5974-5981, copyright 2005 Federation of European Biochemical Societies, Published by Elsevier B.V.

Chiu, Y.I. et al., "siRNA Function in RNAi: A Chemical Modification Analysis," RNA, 2003, vol. 9, No. 9, pp. 1034-1048.

Collingwood, M.A. et al., "Chemical Modification Patterns Compatible with High Potency Dicer-Substrate Small Interfering RNA," Oligonucleotides, 2003, vol. 18, No. 2, pp. 187-200, copyright Mary Ann Liebert, Inc.

EP Communication dated Mar. 9, 2011, extended European search report, Ref: H8/P41889EP; Appln No. 08742798.5-1212 / 2155772 PCT/US2008004726, City of Hope et al., 4 pages.

Peek, A.S. et al., "Design of Active Small Interfering RNAs,", Current Opinion in Molecular Theraputics, 2007, vol. 9, No. 2, pp. 110-118, copyright The Thomson Corporation ISSN 1464-8431.

Singapore IPO Office Action dated Mar. 1, 2011, Singapore Patent Application No. 200907195-2, 12 pages.

Non-Final Office Action dated Apr. 14, 2006. U.S. Appl. No. 11/079,906, filed Mar. 15, 2005; Response to Office Action dated Aug. 14, 2008, 51 pages.

Non-Final Office Action dated Dec. 1, 2008, U.S. Appl. No. 11/079,906, filed Mar. 15, 2005; Response to Office Action dated Jun. 1, 2009, 49 pages.

Final Office Action dated Sep. 18, 2009, U.S. Appl. No. 11/079,906, filed Mar. 15, 2005; Response to Office Action dated May 18, 2010, 53 pages.

Non-Final Office Action dated Nov. 19, 2007, U.S. Appl. No. 11/079,476, filed Mar. 15, 2005; Response to Office Action dated May 19, 2008, 24 pages.

Non-Final Office Action dated Sep. 5, 2008, U.S. Appl. No. 11/709,476, filed Mar. 15, 2005; Response to Office Action dated Feb. 5, 2009, 23 pages.

Supplemental Response to Office Action dated Apr. 16, 2009, 4 pages, U.S. Appl. No. 11/079,476, filed Mar. 15, 2005.

Final Office Action dated Jul. 15, 2009, U.S. Appl. No. 11/079,476, filed Mar. 15, 2005; Response to Office Action dated Jan. 15, 2010, 19 pages.

Advisory Action dated Feb. 19, 2010, U.S. Appl. No. 11/079,476, filed Mar. 15, 2005.

Non-Final Office Action dated Dec. 31, 2009, U.S. Appl. No. 11/797,210, filed May 1, 2007.

Non-Final Office Action dated Mar. 20, 2009, U.S. Appl. No. 12/137,914, filed Jun. 12, 2008; Response to Office Action dated Jul. 20, 2009, 19 pages.

Non-Final Office Action dated Mar. 19, 2009, U.S. Appl. No. 12/138,215, filed Jun. 12, 2008; Response to Office Action dated Jul. 20, 2009, 14 pages.

Final Office Action dated Apr. 30, 2010, U.S. Appl. No. 12/138,215, filed Jun. 12, 2008.

Non-Final Office Action dated Jun. 19, 2009, U.S. Appl. No. 12/143,006, filed Jun. 20, 2006; Response to Office Action dated Oct. 16, 2009, 32 pages.

Non-Final Office Action dated Jun. 15, 2009, U.S. Appl. No. 12/143,009, filed Jun. 20, 2008; Response to Office Action dated Oct. 14, 2009, 32 pages.

Non-Final Office Action dated Jun. 10, 2009, U.S. Appl. No. 12/143,024, filed Jun. 20, 2008; Response to Office Action dated Oct. 13, 2009, 23 pages.

Non-Final Office Action dated Apr. 3, 2009, U.S. Appl. No. 12/143,027, filed Jun. 20, 2008; Response to Office Action dated Oct. 5, 2009, 20 pages.

Choung, S. et al., "Chemical modification of siRNAs to improve serum stability without loss of efficacy," Biochemical and Biophysical Research Communications, 342 (2006), pp. 919-927, © 2006 Elsevier Inc.

Rose, S.D. et al., "Functional polarity is introduced by Dicer processing of short substrate RNAs," Nucleic Acids Research, 2005, vol. 33, No. 13, pp. 4140-4156, © The Author 2005, published by Oxford University Press.

International Search Report dated Sep. 2, 2008, PCT/US 08/04726, International filing date, Apr. 11, 2008, 4 pages.

Paroo, et al., "Challenges for RNAi in vivo," Trends in Biotechnology (2004), vol. 22(8) 390-394, Elsevier.

Caplen, N.J., "RNAi as a Gene Therapy Aoproach," Expert Opinion. Biol. Thera. (2003) vol. 3(4) 575-586. Ashley Publications Ltd.

Adams, A., "RNA therapeutics enter clinical trials," Scientist (2005), vol. 19:Issue 1, 4 pages. Institute for Scientific Information.

Novina et al., "The RNAi Revolution," Nature 2004, vol. 430: 161-164, Nature Pubiishing Group.

Grunweller et al, "Comparison of different antisense strategies in mammalian cells using locked nucleic acids, 2'-O-methyl RNA, phosphorothiates and small interfering RNA," Nucleic Acids Research, 2003, vol. 32, No. 12, pp. 3185-3193.

Hannoush et al, "Remarkable Stability of Hairpins Containing 2', 5'-linked RNA Loops," J. Am. Chem. Soc. 2001, vol. 123, pp. 12366-12374.

(56) References Cited

OTHER PUBLICATIONS

Amarzguioui, M. et al., "Tolerance for Mutations and Chemical Modifications in a siRNA," Nucleic Acids Research, vol. 31, No. 2, 2003, pp. 589-595.
Braasch et al., "RNA Interference in Mammalian Cells by Chemically-Modified RNA," Biochemistry, vol. 42, 2003, pp. 7967-7975.
Bernstein, E., et al. "Role for a bidentate ribonuclease in the initiation step of RNA interference," Nature, vol. 409, (2001) pp. 363-366.
Caplen, N.J., et al, "Specific inhibition of gene expression by small double-stranded RNAs in invertebrate and vertebrate systems," Proc. Nat'l Acad. Sci., USA, 2001, vol. 98, No. 17, pp. 9742-9747.
Elbashir, S.M., et al., "Duplexes of 21-nucleotide RNAs mediate RNA interference in cultured mammalian cells," Nature, vol. 411, (2001) pp. 494-498.
Elbashir, S.M., et al., "RNA interference is mediated by 21- and 22-nucleotide RNAs," Genes & Development, vol. 15, pp. 188-200, 2001.
Elmen, J., et al., "Locked nucleic acid (LNA) mediated improvements in siRNA stability and functionality," Nucleic Acids Res., vol. 33, No. 1, 2005, pp. 439-447.
Fire, A., et al., "Potent and specific genetic Interference by double-stranded RNA in Caenorhabditis elegans," Nature, Feb. 1998, vol. 391, pp. 806-811.
Harborth, J., et al., "Sequence, chemical, and structural variation of small interfering RNAs and short hairpin RNAs and the effect on mammalian gene silencing," Antisense Nucleic Acid Drug Dev., (2003), vol. 13, pp. 83-105.
Hemmings-Mieszczak, M., et al., "Independent combinatorial effect of antisense oligonucleotides and RNAI-mediated specific inhibition of the recombinant rat P2X3 receptor," Nucleic Acids Res., Apr. 2003, vol. 31, No. 8, pp. 2117-2126.
Hohjoh, H., "RNA interference (RNAi) induction with various types of synthetic oligonucleotide duplexes in cultured human cells," FEBS Lett, (2002) vol. 521, pp. 195-199.
Kim, D.H., at al., "Synthetic dsRNA Dicer substrates enhance RNAi potency and efficacy," Nat. Biotechnology, Feb. 2005, vol. 23, No. 2, pp. 222-226.
Khvorova, A., et al., "Functional siRNAs and miRNAs exhibit strand bias," Cell, vol. 115, Oct. 2003, pp. 209-216.
Kurreck, J., et al., "Design of antisense oligonucleotides stabilized by locked nucleic acids," Nucleic Acids Res., 2002, vol. 30, pp. 1911-1918.
Krol, J., et al., "Structural features of microRNA (miRNA) precursors and their relevance to miRNA biogenesis and small interfering RNA/short hairpin RNA design," J. Biological Chemistry, vol. 279, No. 40, Oct. 2004, pp. 42230-42239.
Martinez, J., et al, "Single-stranded antisense siRNAs guide target RNA cleavage in RNAi," Cell, Sep. 2002, vol. 110, pp. 563-574.
McManus, et al., "Gene Silencing in Mammals by Small Interfering RNAs," Nature Reviews Genetics, Oct. 2002, vol. 3, pp. 737-747.
Murchison, E.P., et al., "miRNAs on the move: miRNA biogenesis and the RNAi machinery," Curr. Opin. Cell Biology, Jun. 2004, vol. 16, No. 3, pp. 223-229.
Parrish, S., et al., "Functional anatomy of a dsRNA trigger: differential requirement for the two trigger strands in RNA interference," Mol. Cell, Nov. 2000, vol. 6, pp. 1077-1087.
Paul, C., et al, "Effective expression of small interfering RNA in human cells," Nat. Biotech, May 2002, vol. 20, pp. 505-508.
Reynolds, A., et al., "Rational siRNA design for RNA interference," Nat. Biotechnol. (2004), vol. 22, No. 3, pp. 326-330.
Scherer et al., "Approaches for the Sequence-Specific Knockdown of mRNA," Nature Biotechnology, Dec. 2003, vol. 21, No. 12, pp. 1457-1465.
Schwarz, D.S., et al., "Asymmetry in the assembly of the RNAi enzyme complex," Cell, 2003, vol. 115, pp. 199-208.
Siolas, D., et al., "Synthetic shRNAs as potent RNAi triggers," Nat. Biotechnology, Feb. 2005, vol. 23, No. 2, pp. 227-231.
Tomari, Y., et al., "A protein sensor for siRNA asymmetry," Science, vol. 306, Nov. 2004, pp. 1377-1380.
Tuschl, T., "Expanding small RNA interference," Nat Biotech., vol. 20, May 2002, pp. 446-448.
Ui-Tei K., et al., "Guideiines for the selection of highly effective siRNA sequences for mammalian and chick RNA interference," Nucleic Acids Res., (2004), vol. 32, No. 3, pp. 936-948.
Vermeulen, A., et al, "The contributions of dsRNA structure of Dicer specificity and efficiency," RNA, May 2005, vol. 11, No. 5, pp. 674-682.
Williams, Bryan R.G., "Dicing with siRNA," Nature Biotechnology, vol. 23, No. 2, pp. 181-182, Feb. 2005.
Zamore, P. et al., "RNAi: Double-Stranded RNA Directs the ATP-Dependent Cleavage of mRNA at 21 to 23 Nucleotide Intervals," Cell, vol. 101, pp. 25-33, Mar. 31, 2000.
Czauderna et al., "Structural Variations and Stabilising Modifications of Synthetic siRNAs in Mammalian Cells," Nucleic Acids Research 2003, vol. 31, No. 11, pp. 2705-2716.
Zhang at al., "Human Dicer Preferentially Cleaves dsRNAs at their Termini Without a Requirement for ATP," EMBO 2002, vol. 21, No. 21, pp. 5875-5085.
European Office Action dated Nov. 24, 2014, EP Application No. 05 732 148.1, 5 pages.
European Office Action dated Nov. 24, 2014, EP Application No. 12 174 021.1, 5 pages.

| RNA | Concentration | Hour | 2 X or more/16282 | -2 X or less/16282 |
|---|---|---|---|---|
| Site I/21mer | 50 nM | 24 | 11 | 5 |
|  |  | 48 | 21 | 20 |
| Site I/27mer | 5 nm | 24 | 10* | 4* |
|  |  | 48 | 9* | 23* |
|  | 25 nM | 24 | 71* | 3* |
|  |  | 48 | 22* | 0* |
| * none of them are the identical gene |||||

| NAME | | SEQUENCE (SEQ ID NO:) |
|---|---|---|
| target gene | 5' | acggcaagctgaccctgaagttcatctgcaccaccggcaagctgcccg (116) |
| | | |
| parent 21mer | 5' | ACCCUGAAGUUCAUCUGCACC (11) |
| | 3' | ACUGGGACUUCAAGUAGACGU (12) |
| | | |
| L 27mer | 5' | AAGCUGACCCUGAAGUUCAUCUGCACC (41) |
| | 3' | UUCGACUGGGACUUCAAGUAGACGUGG (42) |
| | | |
| L 27mer v2.1 | 5' | AAGCUGACCCUGAAGUUCAUCUGCACC (41) |
| | 3' | ttCGACUGGGACUUCAAGUAGACGUp (102) |
| | | |
| L 27mer v2.1 diced | 5' | AAGCUG ACCCUGAAGUUCAUCUGCACC (41) |
| | 3' | ttCG ACUGGGACUUCAAGUAGACGUp (102) |
| | | |
| R 27mer | 5' | UGACCCUGAAGUUCAUCUGCACCACCG (103) |
| | 3' | ACUGGGACUUCAAGUAGACGUGGUGGC (104) |
| | | |
| R 27mer v2.1 | 5' | pACCCUGAAGUUCAUCUGCACCACcg (111) |
| | 3' | ACUGGGACUUCAAGUAGACGUGGUGGC (112) |
| | | |
| R 27mer v2.1 diced | 5' | pACCCUGAAGUUCAUCUGCACC ACcg (111) |
| | 3' | ACUGGGACUUCAAGUAGACGU GGUGGC (112) |

Figure 11

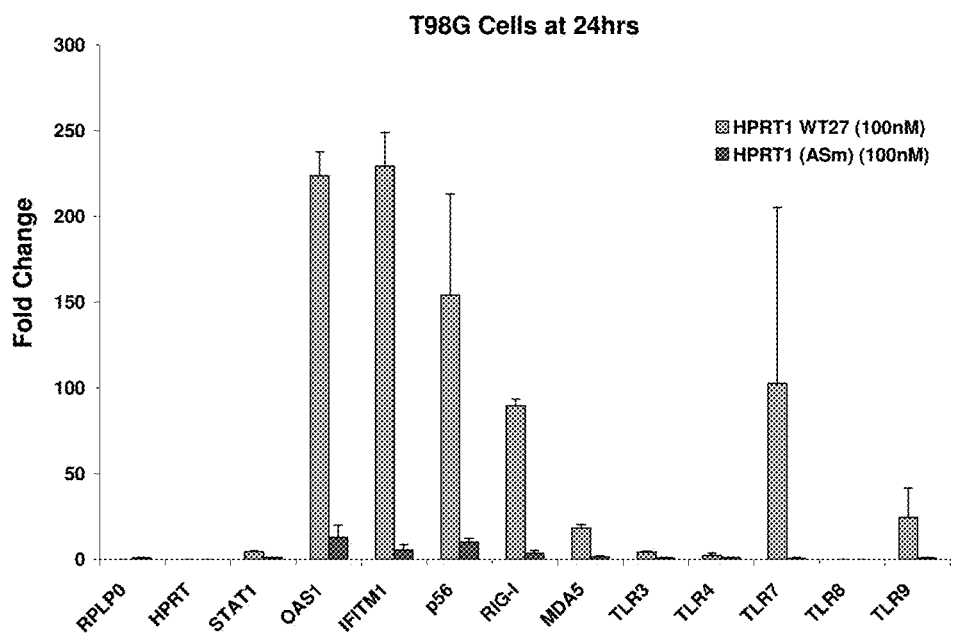
Figure 17A
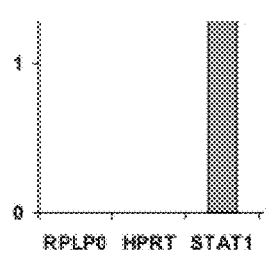 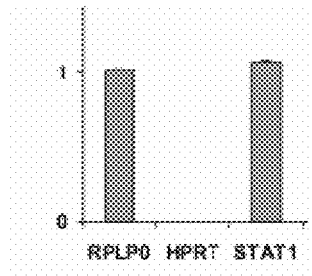
Figure 17B            Figure 17C

METHODS AND COMPOSITIONS FOR THE SPECIFIC INHIBITION OF GENE EXPRESSION BY DOUBLE-STRANDED RNA

CROSS-REFERENCE TO RELATED APPLICATION

The present application is a continuation of U.S. patent application Ser. No. 14/537,578 filed 10 Nov. 2014, which in turn is a continuation of U.S. patent application Ser. No. 13/491,937 filed 8 Jun. 2012, now U.S. Pat. No. 8,883,996, which in turn is a continuation of U.S. patent application Ser. No. 12/143,002 filed 20 Jun. 2008, which in turn is a division of U.S. patent application Ser. No. 11/797,216 filed 1 May 2007. Each of these applications is incorporated herein by reference in its entirety.

STATEMENT REGARDING FEDERALLY SPONSORED RESEARCH AND DEVELOPMENT

The present invention was made in part with Government support under Grant Numbers AI29329 and HL074704 awarded by the National Institute of Health. The Government has certain rights in this invention.

SEQUENCE LISTING SUBMISSION

The present application is being filed along with a Sequence Listing in electronic format. The Sequence Listing is entitled 1954581SequenceListing.txt, created on 4 Aug. 2016 and is 57 kb in size. The information in the electronic format of the Sequence Listing is incorporated herein by reference in its entirety.

FIELD OF THE INVENTION

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The present invention pertains to compositions and methods for gene-specific inhibition of gene expression by double-stranded ribonucleic acid (dsRNA) effector molecules. The compositions and methods are useful in modulating gene expression in a variety of applications, including therapeutic, diagnostic, target validation, and genomic discovery.

BACKGROUND OF THE INVENTION

Suppression of gene expression by double-stranded RNA (dsRNA) has been demonstrated in a variety of systems including plants (post-transcriptional gene suppression) (Napoli et al., 1990), fungi (quelling) (Romano and Marcino, 1992), and nematodes (RNA interference) (Fire et al., 1998). Double-stranded RNA (dsRNA) is significantly more stable than single-stranded RNA (ssRNA). This difference is pronounced in the intracellular environment (Raemdonck et al., 2006). However, unmodified siRNAs are rapidly degraded in serum, which is a fairly nuclease rich environment. Chemical modification can significantly stabilize the siRNA and improve potency both in vitro and in vivo. Extensive medicinal chemistry has been done over the past 20 years for applications where synthetic nucleic acids are used for experimental or therapeutic applications in vivo, such as in the antisense and ribozyme fields, and hundreds of compounds have been tested in a search for modifications that improve nuclease stability, increase binding affinity, and sometimes also improve pharmacodynamic properties of synthetic nucleic acids (Matteucci, 1997; Manoharan, 2002; Kurreck, 2003). Many of these modifications have already been tested and found to have utility as modifiers for use in traditional 21mer siRNAs. Several reviews have provided summaries of recent experience with 21mer siRNAs and chemical modifications (Zhang et al., 2006; Nawrot and Sipa, 2006; Rana, 2007). Modification patterns have not been tested or optimized for use in longer RNAs, such as Dicer-substrate siRNAs (DsiRNAs).

Early attempts to suppress gene expression using long dsRNAs in mammalian systems failed due to activation of interferon pathways that do not exist in lower organisms. Interferon responses are triggered by dsRNAs (Stark et al., 1998). In particular, the protein kinase PKR is activated by dsRNAs of greater than 30 bp long (Manche et al., 1992) and results in phosphorylation of translation initiation factor eIF2α which leads to arrest of protein synthesis and activation of 2'5'-oligoadenylate synthetase (2'-5'-OAS), which leads to RNA degradation (Minks et al., 1979).

In *Drosophila* cells and cell extracts, dsRNAs of 150 bp length or greater were seen to induce RNA interference while shorter dsRNAs were ineffective (Tuschl et al., 1999). Long double-stranded RNA, however, is not the active effector molecule; long dsRNAs are degraded by an RNase III class enzyme called Dicer (Bernstein et al., 2001) into very short 21-23 bp duplexes that have 2-base 3'-overhangs (Zamore et al., 2000). These short RNA duplexes, called siRNAs, direct the RNAi response in vivo and transfection of short chemically synthesized siRNA duplexes of this design permits use of RNAi methods to suppress gene expression in mammalian cells without triggering unwanted interferon responses (Elbashir et al., 2001a). The antisense strand of the siRNA duplex serves as a sequence-specific guide that directs activity of an endoribonuclease function in the RNA induced silencing complex (RISC) to degrade target mRNA (Martinez et al., 2002).

In studying the size limits for RNAi in *Drosophila* embryo extracts in vitro, a lower threshold of around 38 bp double-stranded RNA was established for activation of RNA interference using exogenously supplied double-stranded RNA and duplexes of 36, 30, and 29 bp length (Elbashir et al., 2001b). The short 30-base RNAs were not cleaved into active 21-23-base siRNAs and therefore were deemed inactive for use in RNAi (Elbashir et al., 2001b). Continuing to work in the *Drosophila* embryo extract system, the same group later carefully mapped the structural features needed for short chemically synthesized RNA duplexes to function as siRNAs in RNAi pathways. RNA duplexes of 21-bp length with 2-base 3'-overhangs were most effective, duplexes of 20, 22, and 23-bp length had slightly decreased potency but did result in RNAi mediated mRNA degradation, and 24 and 25-bp duplexes were inactive (Elbashir et al., 2001c).

Some of the conclusions of these earlier studies may be specific to the *Drosophila* system employed. Other investigators established that longer siRNAs can work in human cells. However, duplexes in the 21-23-bp range have been shown to be more active and have become the accepted design (Caplen et al., 2001). Essentially, chemically synthesized duplex RNAs that mimicked the natural products that result from Dicer degradation of long duplex RNAs were identified to be the preferred compound for use in RNAi.

Approaching this problem from the opposite direction, investigators studying size limits for RNAi in *Caenorhabditis elegans* found that although a microinjected 26-bp RNA duplex could function to suppress gene expression, it required a 250-fold increase in concentration compared with an 81-bp duplex (Parrish et al., 2000).

Despite the attention given to RNAi research recently, the field is still in the early stages of development. Not all siRNA molecules are capable of targeting the destruction of their complementary RNAs in a cell. As a result, complex sets of rules have been developed for designing RNAi molecules that will be effective. Those having skill in the art expect to test multiple siRNA molecules to find functional compositions. (Ji et al., 2003) Some artisans pool several siRNA preparations together to increase the chance of obtaining silencing in a single study. (Ji et al., 2003) Such pools typically contain 20 nM of a mixture of siRNA oligonucleotide duplexes or more (Ji et al., 2003), despite the fact that a siRNA molecule can work at concentrations of 1 nM or less (Holen et al., 2002). This technique can lead to artifacts caused by interactions of the siRNA sequences with other cellular RNAs ("off target effects"). (Scherer et al., 2003) Off target effects can occur when the RNAi oligonucleotides have homology to unintended targets or when the RISC complex incorporates the unintended strand from and RNAi duplex. (Scherer et al., 2003) Generally, these effects tend to be more pronounced when higher concentrations of RNAi duplexes are used. (Scherer et al., 2003)

In addition, the duration of the effect of an effective RNAi treatment is limited to about 4 days (Holen et al., 2002). Thus, researchers must carry out siRNA experiments within 2-3 days of transfection with an siRNA duplex or work with plasmid or viral expression vectors to obtain longer term silencing.

One major factor that inhibits the effect of siRNAs is the degradation of siRNAs by nucleases. A 3'-exonuclease is the primary nuclease activity present in serum and modification of the 3'-ends of antisense DNA oligonucleotides is crucial to prevent degradation (Eder et al., 1991). An RNase-T family nuclease has been identified called ERI-1 which has 3'→5' exonuclease activity that is involved in regulation and degradation of siRNAs (Kennedy et al., 2004; Hong et al., 2005). This gene is also known as Thex1 (NM_02067) in mice or THEX1 (NM_153332) in humans and is involved in degradation of histone mRNA; it also mediates degradation of 3'-overhangs in siRNAs, but does not degrade duplex RNA (Yang et al., 2006). It is therefore reasonable to expect that 3'-end-stabilization of siRNAs will improve stability.

XRN1 (NM_019001) is a 5'→3' exonuclease that resides in P-bodies and has been implicated in degradation of mRNA targeted by miRNA (Rehwinkel et al., 2005) and may also be responsible for completing degradation initiated by internal cleavage as directed by a siRNA. XRN2 (NM_012255) is a distinct 5'→3' exonuclease that is involved in nuclear RNA processing. Although not currently implicated in degradation or processing of siRNAs and miRNAs, these both are known nucleases that can degrade RNAs and may also be important to consider.

RNase A is a major endonuclease activity in mammals that degrades RNAs. It is specific for ssRNA and cleaves at the 3'-end of pyrimidine bases. SiRNA degradation products consistent with RNase A cleavage can be detected by mass spectrometry after incubation in serum (Turner et al., 2007). The 3'-overhangs enhance the susceptibility of siRNAs to RNase degradation. Depletion of RNase A from serum reduces degradation of siRNAs; this degradation does show some sequence preference and is worse for sequences having poly A/U sequence on the ends (Haupenthal et al., 2006). This suggests the possibility that lower stability regions of the duplex may "breathe" and offer transient single-stranded species available for degradation by RNase A. RNase A inhibitors can be added to serum and improve siRNA longevity and potency (Haupenthal et al., 2007).

In 21mers, phosphorothioate or boranophosphate modifications directly stabilize the internucleoside phosphate linkage. Boranophosphate modified RNAs are highly nuclease resistant, potent as silencing agents, and are relatively non-toxic. Boranophosphate modified RNAs cannot be manufactured using standard chemical synthesis methods and instead are made by in vitro transcription (IVT) (Hall et al., 2004 and Hall et al., 2006). Phosphorothioate (PS) modifications can be easily placed in the RNA duplex at any desired position and can be made using standard chemical synthesis methods. The PS modification shows dose-dependent toxicity, so most investigators have recommended limited incorporation in siRNAs, favoring the 3'-ends where protection from nucleases is most important (Harborth et al., 2003; Chiu and Rana, 2003; Braasch et al., 2003; Amarzguioui et al., 2003). More extensive PS modification can be compatible with potent RNAi activity; however, use of sugar modifications (such as 2'-O-methyl RNA) may be superior (Choung et al., 2006).

A variety of substitutions can be placed at the 2'-position of the ribose which generally increases duplex stability ($T_m$) and can greatly improve nuclease resistance. 2'-O-methyl RNA is a naturally occurring modification found in mammalian ribosomal RNAs and transfer RNAs. 2'-O-methyl modification in siRNAs is known, but the precise position of modified bases within the duplex is important to retain potency and complete substitution of 2'-O-methyl RNA for RNA will inactivate the siRNA. For example, a pattern that employs alternating 2'-O-methyl bases can have potency equivalent to unmodified RNA and is quite stable in serum (Choung et al., 2006; Czauderna et al., 2003).

The 2'-fluoro (2'-F) modification is also compatible with siRNA function; it is most commonly placed at pyrimidine sites (due to reagent cost and availability) and can be combined with 2'-O-methyl modification at purine positions; 2'-F purines are available and can also be used. Heavily modified duplexes of this kind can be potent triggers of RNAi in vitro (Allerson et al., 2005; Prakash et al., 2005; Kraynack and Baker, 2006) and can improve performance and extend duration of action when used in vivo (Morrissey et al., 2005a; Morrissey et al., 2005b). A highly potent, nuclease stable, blunt 19mer duplex containing alternative 2'-F and 2'-O-Me bases is taught by Allerson. In this design, alternating 2'-O-Me residues are positioned in an identical pattern to that employed by Czauderna, however the remaining RNA residues are converted to 2'-F modified bases. A highly potent, nuclease resistant siRNA employed by Morrissey employed a highly potent, nuclease resistant siRNA in vivo. In addition to 2'-O-Me RNA and 2'-F RNA, this duplex includes DNA, RNA, inverted abasic residues, and a 3'-terminal PS internucleoside linkage. While extensive modification has certain benefits, more limited modification of the duplex can also improve in vivo performance and is both simpler and less costly to manufacture. Soutschek et al. (2004) employed a duplex in vivo and was mostly RNA with two 2'-O-Me RNA bases and limited 3'-terminal PS internucleoside linkages.

Locked nucleic acids (LNAs) are a different class of 2'-modification that can be used to stabilize siRNAs. Patterns of LNA incorporation that retain potency are more restricted than 2'-O-methyl or 2'-F bases, so limited modification is preferred (Braasch et al., 2003; Grunweller et al., 2003; Elmen et al., 2005). Even with limited incorporation, the use of LNA modifications can improve siRNA performance in vivo and may also alter or improve off target effect profiles (Mook et al., 2007).

Synthetic nucleic acids introduced into cells or live animals can be recognized as "foreign" and trigger an immune response Immune stimulation constitutes a major class of off-target effects which can dramatically change experimental results and even lead to cell death. The innate immune system includes a collection of receptor molecules that specifically interact with DNA and RNA that mediate these responses, some of which are located in the cytoplasm and some of which reside in endosomes (Marques and Williams, 2005; Schlee et al., 2006). Delivery of siRNAs by cationic lipids or liposomes exposes the siRNA to both cytoplasmic and endosomal compartments, maximizing the risk for triggering a type 1 interferon (IFN) response both in vitro and in vivo (Morrissey et al., 2005b; Sioud and Sorensen, 2003; Sioud, 2005; Ma et al., 2005). RNAs transcribed within the cell are less immunogenic (Robbins et al., 2006) and synthetic RNAs that are immunogenic when delivered using lipid-based methods can evade immune stimulation when introduced unto cells by mechanical means, even in vivo (Heidel et al., 2004). However, lipid based delivery methods are convenient, effective, and widely used. Some general strategy to prevent immune responses is needed, especially for in vivo application where all cell types are present and the risk of generating an immune response is highest. Use of chemically modified RNAs may solve most or even all of these problems.

Although certain sequence motifs are clearly more immunogenic than others, it appears that the receptors of the innate immune system in general distinguish the presence or absence of certain base modifications which are more commonly found in mammalian RNAs than in prokaryotic RNAs. For example, pseudouridine, N6-methyl-A, and 2'-O-methyl modified bases are recognized as "self" and inclusion of these residues in a synthetic RNA can help evade immune detection (Kariko et al., 2005). Extensive 2'-modification of a sequence that is strongly immunostimulatory as unmodified RNA can block an immune response when administered to mice intravenously (Morrissey et al., 2005b). However, extensive modification is not needed to escape immune detection and substitution of as few as two 2'-O-methyl bases in a single strand of a siRNA duplex can be sufficient to block a type 1 IFN response both in vitro and in vivo; modified U and G bases are most effective (Judge et al., 2006). As an added benefit, selective incorporation of 2'-O-methyl bases can reduce the magnitude of off-target effects (Jackson et al., 2006). Use of 2'-O-methyl bases should therefore be considered for all siRNAs intended for in vivo applications as a means of blocking immune responses and has the added benefit of improving nuclease stability and reducing the likelihood of off-target effects.

Although cell death can results from immune stimulation, assessing cell viability is not an adequate method to monitor induction of IFN responses. IFN responses can be present without cell death, and cell death can result from target knockdown in the absence of IFN triggering (for example, if the targeted gene is essential for cell viability). Relevant cytokines can be directly measured in culture medium and a variety of commercial kits exist which make performing such assays routine. While a large number of different immune effector molecules can be measured, testing levels of IFN-α, TNF-α, and IL-6 at 4 and 24 hours post transfection is usually sufficient for screening purposes. It is important to include a "transfection reagent only control" as cationic lipids can trigger immune responses in certain cells in the absence of any nucleic acid cargo. Including controls for IFN pathway induction should be considered for cell culture work. It is essential to test for immune stimulation whenever administering nucleic acids in vivo, where the risk of triggering IFN responses is highest.

There is therefore a need to provide a chemical modification pattern that would enhance the efficacy of a dsRNA, particularly DsiRNA. The modifications 1) should not reduce potency; 2) should not interfere with Dicer processing; 3) should improve stability in biological fluids (reduce nuclease sensitivity); 4) should block or evade detection by the innate immune system; 5) should not be toxic; and 6) should not increase cost or impact ease of manufacturing.

The invention provides compositions useful in RNAi for inhibiting gene expression and provides methods for their use. In addition, the invention provides RNAi compositions and methods designed to maximize potency, enhance Dicer processing, improve stability while evading the immune system and are not toxic. Additionally, various embodiments of the invention are suited for high throughput, small scale synthesis to meet research needs as well as large scale manufacturing for therapeutic applications. These and other advantages of the invention, as well as additional inventive features, will be apparent from the description of the invention provided herein.

BRIEF SUMMARY OF THE INVENTION

The present invention is directed to compositions that contain double stranded RNA ("dsRNA"), and methods for preparing them, that are capable of reducing the expression of target genes in eukaryotic cells. More particularly, the invention is directed to Dicer substrate RNAs with modifications that are functionally improved.

Thus, in a first aspect, the present invention provides novel compositions for RNA interference (RNAi). The compositions comprise dsRNA which is a precursor molecule, i.e., the dsRNA of the present invention is processed in vivo to produce an active siRNA. The dsRNA is processed by Dicer to an active siRNA which is incorporated into the RISC complex for RNA interference of a target gene. The precursor molecule is also termed a precursor RNAi molecule herein.

In one embodiment, the dsRNA, i.e., the precursor RNAi molecule, has a length sufficient such that it is processed by Dicer to produce an siRNA. According to this embodiment, the dsRNA comprises a first oligonucleotide sequence (also termed the sense strand) that is between 26 and about 30 nucleotides in length and a second oligonucleotide sequence (also termed the antisense strand) that anneals to the first sequence under biological conditions, such as the conditions found in the cytoplasm of a cell. In addition, a region of one of the sequences, particularly of the antisense strand, of the dsRNA has a sequence length of at least 19 nucleotides, for example, from about 19 to about 23 nucleotides, such as 21 nucleotides that are sufficiently complementary to a nucleotide sequence of the RNA produced from the target gene to trigger an RNAi response.

In a second embodiment, the dsRNA, i.e., the precursor RNAi molecule, has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3' overhang on the antisense strand and (ii) the dsRNA has a modified 3' end on the sense strand to direct orientation of Dicer binding and processing of the dsRNA to an active siRNA. According to this embodiment, the sense strand comprises 22-28 nucleotides and the antisense strand comprises 24-30 nucleotides. In one embodiment, the dsRNA has an overhang on the 3' end of the antisense strand. In another embodiment, the sense strand is modified for Dicer binding and processing by suitable modifiers located at the 3' end of the sense strand. Suitable modifiers include nucleotides such as deoxyribonucleotides, acyclonucleotides and the like and sterically hindered molecules, such as fluorescent molecules and the like. When nucleotide modifiers are used, they replace ribonucleotides in the dsRNA such that the length of the dsRNA does not change. In another embodiment, the dsRNA has an overhang on the 3' end of the antisense strand and the sense strand is modified for Dicer processing. In another embodiment, the 5' end of the sense strand has a phosphate. In another embodiment, the 5' end of the antisense strand has a phosphate. In another embodiment, the antisense strand or the sense strand or both strands have one or more 2'-O-methyl modified nucleotides. In another embodiment, the antisense strand contains 2'-O-methyl modified nucleotides. In another embodiment, the antisense stand contains a 3' overhang that is comprised of 2'-O-methyl modified nucleotides. The antisense strand could also include additional 2'-O-methyl modified nucleotides. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are in the 21-nucleotide region adjacent to the 3' end of the antisense strand and are sufficiently complementary to a nucleotide sequence of the RNA produced from the target gene. Further in accordance with this embodiment, the dsRNA, i.e., the precursor RNAi molecule, may also have one or more of the following additional properties: (a) the antisense strand has a right shift from the typical 21mer (i.e., the antisense strand includes nucleotides on the right side of the molecule when compared to the typical 21mer), (b) the strands may not be completely complementary, i.e., the strands may contain simple mismatch pairings and (c) base modifications such as locked nucleic acid(s) may be included in the 5' end of the sense strand.

In a third embodiment, the sense strand comprises 25-28 nucleotides, wherein the 2 nucleotides on the 3' end of the sense strand are deoxyribonucleotides. The sense strand contains a phosphate at the 5' end. The antisense strand comprises 26-30 nucleotides and contains a 3' overhang of 1-4 nucleotides. The nucleotides comprising the 3' overhang are modified with 2'-O-methyl RNA. The antisense strand contains alternating 2'-O-methyl modified nucleotides beginning at the first monomer of the antisense strand adjacent to the 3' overhang, and extending 15-19 nucleotides from the first monomer adjacent to the 3' overhang. For example, for a 27 nucleotide antisense strand and counting the first base at the 5'-end of the antisense strand as position number 1, 2'OMe modifications would be placed at bases 9, 11, 13, 15, 17, 19, 21, 23, 25, 26, and 27. In one embodiment, the DsiRNA comprises:

```
5'  pXXXXXXXXXXXXXXXXXXXXXXXDD
3'  YXXXXXXXXXXXXXXXXXXXXXXXXXXp
``` wherein "X"=RNA, "p"=a phosphate group, "X"=2'-O-methyl RNA, "Y" is an overhang domain comprised of 1-4 RNA monomers that are optionally 2'-O-methyl RNA monomers, and "D"=DNA. The top strand is the sense strand, and the bottom strand is the antisense strand.

In a fourth embodiment, the dsRNA, i.e., the precursor RNAi molecule, has several properties which enhance its processing by Dicer. According to this embodiment, the dsRNA has a length sufficient such that it is processed by Dicer to produce an siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the sense strand comprises 24-30 nucleotides and the antisense strand comprises 22-28 nucleotides. In one embodiment, the dsRNA has an overhang on the 3' end of the sense strand. In another embodiment, the antisense strand is modified for Dicer binding and processing by suitable modifiers located at the 3' end of the antisense strand. Suitable modifiers include nucleotides such as deoxyribonucleotides, acyclonucleotides and the like and sterically hindered molecules, such as fluorescent molecules and the like. When nucleotide modifiers are used, they replace ribonucleotides in the dsRNA such that the length of the dsRNA does not change. In another embodiment, the dsRNA has an overhang on the 3' end of the sense strand and the antisense strand is modified for Dicer processing. In one embodiment, the antisense strand has a 5' phosphate. The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the RNA produced from the target gene. Further in accordance with this embodiment, the dsRNA, i.e., the precursor RNAi molecule, may also have one or more of the following additional properties: (a) the antisense strand has a left shift from the typical 21mer (i.e., the antisense strand includes nucleotides on the left side of the molecule when compared to the typical 21mer) and (b) the strands may not be completely complementary, i.e., the strands may contain simple mismatch pairings.

In a second aspect, the present invention provides a method for making a dsRNA, i.e., a precursor RNAi molecule, that has enhanced processing by Dicer. According to this method an antisense strand siRNA having a length of at least 19 nucleotides is selected for a given target gene using conventional techniques and algorithms. In one embodiment, the antisense siRNA is modified to include 5-11 ribonucleotides on the 5' end to give a length of 24-30 nucleotides. When the antisense strand has a length of 21 nucleotides, then 3-9 nucleotides, or 4-7 nucleotides or 6 nucleotides are added on the 5' end. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has 22-28 nucleotides. The sense strand is substantially complementary with the antisense strand to anneal to the antisense strand under biological conditions. In one embodiment, the sense strand is synthesized to contain a modified 3' end to direct Dicer processing of the antisense strand. In another embodiment, the antisense strand of the dsRNA has a 3' overhang. In a further embodiment, the sense strand is synthesized to contain a modified 3' end for Dicer binding and processing and the antisense strand of the dsRNA has a 3' overhang.

In a second embodiment of this method, the antisense siRNA is modified to include 1-9 ribonucleotides on the 5' end to give a length of 22-28 nucleotides. When the antisense strand has a length of 21 nucleotides, then 1-7 ribonucleotides, or 2-5 ribonucleotides and or 4 ribonucleotides are added on the 3'end. The added ribonucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. A sense strand is then produced that has 24-30 nucleotides. The sense strand is substantially complementary with the antisense strand to anneal to the antisense strand under biological conditions. In one embodiment, the antisense strand is synthesized to contain a modified 3' end to direct Dicer processing. In another embodiment, the sense strand of the dsRNA has a 3' overhang. In a further embodiment, the antisense strand is synthesized to contain a modified 3' end for Dicer binding and processing and the sense strand of the dsRNA has a 3' overhang.

In a third aspect, the present invention provides pharmaceutical compositions containing the disclosed dsRNA compositions.

In a fourth aspect, the present invention provides methods for selectively reducing the expression of a gene product from a desired target gene in a cell, as well as for treating diseases caused by the expression of the gene. In one embodiment, the method involves introducing into the environment of a cell an amount of a dsRNA of the present invention such that a sufficient portion of the dsRNA can enter the cytoplasm of the cell to cause a reduction in the expression of the target gene.

The compositions and methods have an unanticipated level of potency of the RNAi effect. Although the invention is not intended to be limited by the underlying theory on which it is believed to operate, it is thought that this level of potency and duration of action are caused by the fact the dsRNA serves as a substrate for Dicer which appears to facilitate incorporation of one sequence from the dsRNA into the RISC complex that is directly responsible for destruction of the RNA from the target gene.

BRIEF DESCRIPTION OF THE DRAWINGS

FIGS. 1A-1C: Transfections were performed using (FIG. 1A) 50 nM, (FIG. 1B) 200 pM and (FIG. 1C) 50 pM of the indicated dsRNAs. FIG. 1D: Dose-response testing of longer dsRNAs. Transfections were performed with the indicated concentrations of dsRNA. FIG. 1E: Depicts in vitro Dicer reactions with the same longer RNAs. Concentrations and conditions were as described in the Examples. FIG. 1F: Dose-response curve of dsRNAs transfected into NIH3T3 cells that stably express EGFP. Each graph point represents the average (with s.d.) of three independent measurements.

FIG. 2A: Cleavage of dsRNAs by recombinant Dicer. Each RNA duplex was incubated in the presence or absence of recombinant human Dicer for 24 h, separated using nondenaturing PAGE and visualized (see Examples). FIG. 2B: RNA duplexes used in this test. Oligos were conjugated with 6FAM at the 5' ends, the 3' ends or both as shown by the circles. Top and bottom lines indicate sense and antisense strands in duplex configuration, with the sense in a 5'-to-3' orientation (left to right) and the antisense in a 3'-to-5' orientation (left to right). FIG. 2C: 6FAM end-modification affects in vitro Dicer activity. RNA duplexes were incubated with 0.5 units of recombinant human Dicer for 8 h and the products resolved on a 7.5% nondenaturing polyacrylamide gel. The RNAs were visualized by ethidium bromide staining. FIG. 2D: 6FAM modification affects RNAi activity. RNA duplexes at 200 pM were cotransfected with the EGFP expression plasmid and assayed at 24 h for EGFP fluorescence as described. Reported values for EGFP expression represent the average of two independent experiments. The relative levels of fluorescence were normalized to those for luciferase. FIG. 2E: 27mer duplex RNAs are processed to 21mers in vivo. Total RNA was prepared from cells transfected with duplex 3 and duplex 5 at 10 nM. RNA was hybridized with a 21mer $^{32}$P-labeled oligonucleotide probe. The hybridized samples were separated by nondenaturing PAGE and visualized by autoradiography. Size markers are $^{32}$P end labeled 21mer and 27mer RNA duplexes.

FIG. 3A: Seven possible 21+2 siRNAs predicted from Dicing the 27mer dsRNA were tested individually or as a pool in co-transfection assays with the EGFP reporter construct in HEK293 cells. Each graph depicts the average of duplicate experiments. FIG. 3B: Comparison of in vitro Diced 27mer dsRNA versus intact 27mer dsRNA for RNAi. The respective RNAs were co-transfected as in FIG. 4A at the indicated concentrations of dsRNAs. For the Diced products, a 1 µM 27mer dsRNA was incubated in Dicer reaction buffer without (column 3) or with Dicer (column 4) at 37° C. for 12 hours. The mixtures were diluted in water and used directly for co-transfection with the EGFP reporter. To control for possible artifacts of residual Dicer in the diluted mixes, the samples in column 4 were phenol extracted and ethanol precipitated prior to transfection (column 5).

FIG. 5A: Enhanced duration of RNAi by 27mer dsRNAs. Levels of EGFP were determined after transfection of 5 nM of a 21+2 siRNA or the 27mer dsRNA into NIH3T3 cells stably expressing EGFP. Graphic representation of EGFP silencing mediated by a 21+2 siRNA as compared to the 27mer dsRNA. Duplicate samples were taken on the indicated days and EGFP expression was determined by fluorometry. FIG. 5B: 27mer dsRNAs, targeting sites refractory to 21mer siRNAs, can elicit RNAi. The dsRNAs were transfected along with the EGFP reporter construct, and EGFP expression was determined (Methods). Column 1, mock; column 2, 21+2 siRNA targeting EGFPS2; column 3, 27mer dsRNA targeting EGFPS2; column 4, 21+2 siRNA targeting EGFPS3; column 5, 27mer dsRNA targeting EGFPS3. FIGS. 5C and 5D: Comparison of 21mer siRNA and 27mer dsRNA in downregulation of endogenous transcripts. RNAs for a 21+2 siRNA and 27+0 dsRNA were designed to target sites in the hnRNP H mRNA (FIG. 5C) or La mRNA (FIG. 5D). HnRNP H knockdown was assayed by western blot and La knockdown by northern blot analyses. The dsRNAs were used at the indicated concentrations. β-Actin was used as an internal specificity and loading standard in both experiments.

" FIGS. 7A and 7B: Interferon alpha (FIG. 7A) and interferon beta (FIG. 7B) assays: column 1, positive control for IFN induction (Kim et al., 2004); column 2, no RNA; column 3, chemically synthesized 21+2 siRNA; column 4, chemically synthesized 27+0 dsRNA. FIG. 7C: PKR activation assay. The long dsRNA used for PKR activation (Kim et al., 2004) and the in vitro PKR activation assay (Manche et al, 1992) have been previously described. Duplex RNAs were transfected as indicated. FIG. 7D: Summary of microarray analysis.

FIG. 10A: Compares the potency of the duplexes EGFPS2-21+2, EGFPS2-27+0, EGFPS2-27/25 L and EGFPS2-25/27 R. FIG. 10B: Compares the potency of the duplexes EGFPS1-27/25 L and EGFPS1-25/27 R.

FIG. 11 is an illustration showing two embodiments of the present invention with respect to the target sequence and the relationship between the target sequence and each embodiment.

FIG. 17A shows the relative change in expression levels of a variety of immune pathway genes in T98G cells before and after transfection with unmodified vs. ASm modified DsiRNAs. The 2'-O-methyl modified DsiRNAs resulted in minimal alterations in gene expression levels while unmodified DsiRNAs resulted in over a 200-fold increase in expression of certain genes. Relative mRNA levels were assessed by qRT-PCR at 24 h post transfection.

FIGS. 17B and 17C provide finer detail views of the control gene assay results. In 17B, unmodified HPRT-specific DsiRNAs resulted in reduction of HPRT mRNA levels as well as a reduction of the mRNA levels of a control non-targeted housekeeping gene RPLP0, which is characteristic of a Type-I IFN response. In 17C, the ASm modified HPRT-specific DsiRNA resulted in reduction of HPRT mRNA levels with no change in expression of the control RPLP0 gene.

DETAILED DESCRIPTION OF THE INVENTION

Figure 1A:
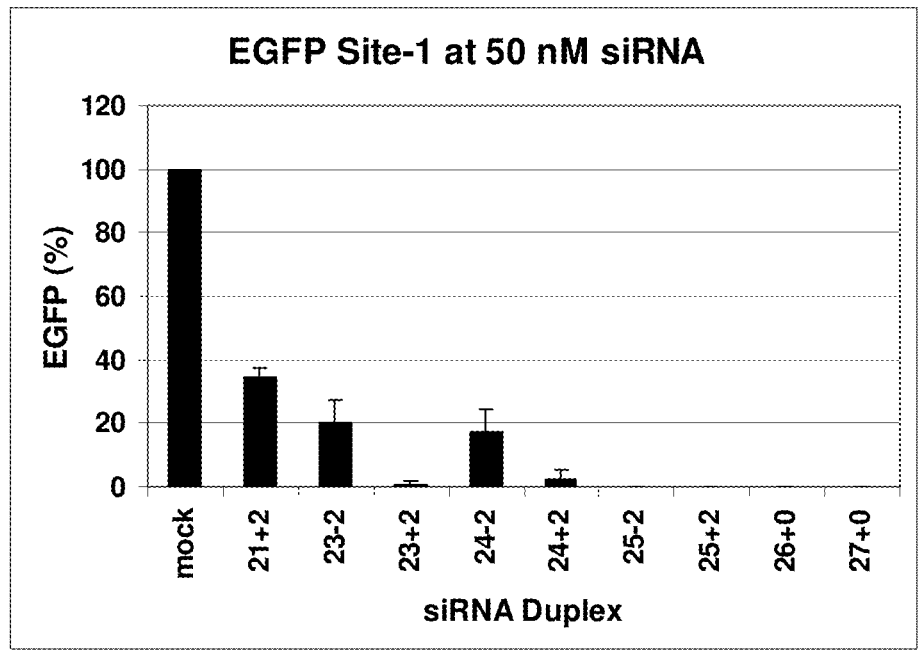
FIGS. 1A-1F show that 27mer dsRNAs are more potent effectors of RNAi than a 21+2 siRNA. EGFP expression levels were determined after cotransfection of HEK293 cells with a fixed amount of EGFP expression plasmid and varying concentrations of dsRNAs.

The present invention is directed to compositions that contain double stranded RNA ("dsRNA"), and methods for preparing them, that are capable of reducing the expression of target genes in eukaryotic cells. One of the strands of the dsRNA contains a region of nucleotide sequence that has a length that ranges from about 19 to about 30 nucleotides that can direct the destruction of the RNA transcribed from the target gene.

In a first aspect, the present invention provides novel compositions for RNA interference (RNAi). The compositions comprise dsRNA which is a precursor molecule, i.e., the dsRNA of the present invention is processed in vivo to produce an active siRNA. The dsRNA is processed by Dicer to an active siRNA which is incorporated into the RISC complex. The precursor molecule is also termed a precursor RNAi molecule herein. As used herein, the term active siRNA refers to a double stranded nucleic acid in which each strand comprises RNA, RNA analog(s) or RNA and DNA. The siRNA comprises between 19 and 23 nucleotides or comprises 21 nucleotides. The active siRNA has 2 bp overhangs on the 3' ends of each strand such that the duplex region in the siRNA comprises 17-21 nucleotides, or 19 nucleotides. Typically, the antisense strand of the siRNA is sufficiently complementary with the target sequence of the target gene.

The phrase "duplex region" refers to the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

As used herein, a siRNA having a sequence "sufficiently complementary" to a target mRNA sequence means that the siRNA has a sequence sufficient to trigger the destruction of the target mRNA by the RNAi machinery (e.g., the RISC complex) or process. The siRNA molecule can be designed such that every residue of the antisense strand is complementary to a residue in the target molecule. Alternatively, substitutions can be made within the molecule to increase stability and/or enhance processing activity of said molecule. Substitutions can be made within the strand or can be made to residues at the ends of the strand.

In one embodiment of the first aspect of the present invention, the dsRNA, i.e., the precursor RNAi molecule, has a length sufficient such that it is processed by Dicer to produce an siRNA. According to this embodiment, a suitable dsRNA contains one oligonucleotide sequence, a first sequence, that is at least 25 nucleotides in length and no longer than about 30 nucleotides. This sequence of RNA can be between about 26 and 29 nucleotides in length. This sequence can be about 27 or 28 nucleotides in length or 27 nucleotides in length. The second sequence of the dsRNA can be any sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotides sequence will have about 21 or more complementary base pairs, or about 25 or more complementary base pairs with the first oligonucleotide sequence. In one embodiment, the second sequence is the same length as the first sequence, and the dsRNA is blunt ended. In another embodiment, the ends of the dsRNA have overhangs.

In certain aspects of this first embodiment, the first and second oligonucleotide sequences of the dsRNA exist on separate oligonucleotide strands that can be and typically are chemically synthesized. In some embodiments, both strands are between 26 and 30 nucleotides in length. In other embodiments, both strands are between 25 and 30 nucleotides in length. In one embodiment, both strands are 27 nucleotides in length, are completely complementary and have blunt ends. The dsRNA can be from a single RNA oligonucleotide that undergoes intramolecular annealing or, more typically, the first and second sequences exist on separate RNA oligonucleotides. In one embodiment, one or both oligonucleotide strands are capable of serving as a substrate for Dicer. In other embodiments, at least one modification is present that promotes Dicer to bind to the double-stranded RNA structure in an orientation that maximizes the double-stranded RNA structure's effectiveness in inhibiting gene expression. The dsRNA can contain one or more deoxyribonucleic acid (DNA) base substitutions.

Suitable dsRNA compositions that contain two separate oligonucleotides can be chemically linked outside their annealing region by chemical linking groups. Many suitable chemical linking groups are known in the art and can be used. Suitable groups will not block Dicer activity on the dsRNA and will not interfere with the directed destruction of the RNA transcribed from the target gene. Alternatively, the two separate oligonucleotides can be linked by a third oligonucleotide such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

The first and second oligonucleotides are not required to be completely complementary. In fact, in one embodiment, the 3'-terminus of the sense strand contains one or more mismatches. In one aspect, about two mismatches are incorporated at the 3'terminus of the sense strand. In another embodiment, the dsRNA of the invention is a double stranded RNA molecule containing two RNA oligonucleotides each of which is 27 nucleotides in length and, when annealed to each other, have blunt ends and a two nucleotide mismatch on the 3'-terminus of the sense strand (the 5'-terminus of the antisense strand). The use of mismatches or decreased thermodynamic stability (specifically at the 3'-sense/5'-antisense position) has been proposed to facilitate or favor entry of the antisense strand into RISC (Schwarz et al., 2003; Khvorova et al., 2003), presumably by affecting some rate-limiting unwinding steps that occur with entry of the siRNA into RISC. Thus, terminal base composition has been included in design algorithms for selecting active 21mer siRNA duplexes (Ui-Tei et al., 2004; Reynolds et al., 2004). With Dicer cleavage of the dsRNA of this embodiment, the small end-terminal sequence which contains the mismatches will either be left unpaired with the antisense strand (become part of a 3'-overhang) or be cleaved entirely off the final 21-mer siRNA. These "mismatches", therefore, do not persist as mismatches in the final RNA component of RISC. It was surprising to find that base mismatches or destabilization of segments at the 3'-end of the sense strand of Dicer substrate improved the potency of synthetic duplexes in RNAi, presumably by facilitating processing by Dicer.

It has been found empirically that these longer dsRNA species of from 25 to about 30 nucleotides give unexpectedly effective results in terms of potency and duration of action. Without wishing to be bound by the underlying theory of the invention, it is thought that the longer dsRNA species serve as a substrate for the enzyme Dicer in the cytoplasm of a cell. In addition to cleaving the dsRNA of the invention into shorter segments, Dicer is thought to facilitate the incorporation of a single-stranded cleavage product derived from the cleaved dsRNA into the RISC complex that is responsible for the destruction of the cytoplasmic RNA derived from the target gene. The studies described herein have shown that the cleavability of a dsRNA species by Dicer corresponds with increased potency and duration of action of the dsRNA species.

In a second embodiment of the first aspect of the present invention, the dsRNA, i.e., the precursor RNAi molecule, has several properties which enhance its processing by Dicer. According to this embodiment, the dsRNA has a length sufficient such that it is processed by Dicer to produce an active siRNA and at least one of the following properties: (i) the dsRNA is asymmetric, e.g., has a 3' overhang on the antisense strand and (ii) the dsRNA has a modified 3' end on the sense strand to direct orientation of Dicer binding and processing of the dsRNA to an active siRNA. According to this embodiment, the longest strand in the dsRNA comprises 24-30 nucleotides. In one embodiment, the dsRNA is asymmetric such that the sense strand comprises 22-28 nucleotides and the antisense strand comprises 24-30 nucleotides. Thus, the resulting dsRNA has an overhang on the 3' end of the antisense strand. The overhang is 1-3 nucleotides, for example 2 nucleotides. The sense strand may also have a 5' phosphate.

In another embodiment, the sense strand is modified for Dicer processing by suitable modifiers located at the 3' end of the sense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotides modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the sense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing of the antisense strand. In a further embodiment of the present invention, two terminal DNA bases are substituted for two ribonucleotides on the 3'-end of the sense strand forming a blunt end of the duplex on the 3' end of the sense strand and the 5' end of the antisense strand, and a two-nucleotide RNA overhang is located on the 3'-end of the antisense strand. This is an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are in the 21-nucleotide region adjacent to the 3' end of the antisense strand and are sufficiently complementary to a nucleotide sequence of the RNA produced from the target gene.

Further in accordance with this embodiment, the dsRNA, i.e., the precursor RNAi molecule, may also have one or more of the following additional properties: (a) the antisense strand has a right shift from the typical 21mer, (b) the strands may not be completely complementary, i.e., the strands may contain simple mismatch pairings and (c) base modifications such as locked nucleic acid(s) may be included in the 5' end of the sense strand. A "typical" 21mer siRNA is designed using conventional techniques. In one technique, a variety of sites are commonly tested in parallel or pools containing several distinct siRNA duplexes specific to the same target with the hope that one of the reagents will be effective (Ji et al., 2003). Other techniques use design rules and algorithms to increase the likelihood of obtaining active RNAi effector molecules (Schwarz et al., 2003; Khvorova et al., 2003; Ui-Tei et al., 2004; Reynolds et al., 2004; Krol et al., 2004; Yuan et al., 2004; Boese et al., 2005). High throughput selection of siRNA has also been developed (U.S. published patent application No. 2005/0042641 A1, incorporated herein by reference). Potential target sites can also be analyzed by secondary structure predictions (Heale et al., 2005). This 21mer is then used to design a right shift to include 3-9 additional nucleotides on the 5' end of the 21mer. The sequence of these additional nucleotides may have any sequence. In one embodiment, the added ribonucleotides are based on the sequence of the target gene. Even in this embodiment, full complementarity between the target sequence and the antisense siRNA is not required.

The first and second oligonucleotides are not required to be completely complementary. They only need to be substantially complementary to anneal under biological conditions and to provide a substrate for Dicer that produces a siRNA sufficiently complementary to the target sequence. Locked nucleic acids, or LNA's, are well known to a skilled artisan (Elman et al., 2005; Kurreck et al., 2002; Crinelli et al., 2002; Braasch and Corey, 2001; Bondensgaard et al., 2000; Wahlestedt et al., 2000). In one embodiment, an LNA is incorporated at the 5' terminus of the sense strand. In another embodiment, an LNA is incorporated at the 5' terminus of the sense strand in duplexes designed to include a 3' overhang on the antisense strand.

In one embodiment, the dsRNA has an asymmetric structure, with the sense strand having a 25-base pair length, and the antisense strand having a 27-base pair length with a 2 base 3'-overhang. In another embodiment, this dsRNA having an asymmetric structure further contains 2 deoxynucleotides at the 3' end of the sense strand in place of two of the ribonucleotides.

Suitable dsRNA compositions that contain two separate oligonucleotides can be linked by a third structure. The third structure will not block Dicer activity on the dsRNA and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the dsRNA is a manner such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

In a third embodiment of the first aspect of the present invention, the dsRNA, i.e., the precursor RNAi molecule, has several properties which enhances its processing by Dicer. According to this embodiment, the dsRNA has a length sufficient such that it is processed by Dicer to produce an siRNA and at least one of the following properties: (i) the dsRNA is asymmetric, e.g., has a 3' overhang on the sense strand and (ii) the dsRNA has a modified 3' end on the antisense strand to direct orientation of Dicer binding and processing of the dsRNA to an active siRNA. According to this embodiment, the longest strand in the dsRNA comprises 24-30 nucleotides. In one embodiment, the sense strand comprises 24-30 nucleotides and the antisense strand comprises 22-28 nucleotides. Thus, the resulting dsRNA has an overhang on the 3' end of the sense strand. The overhang is 1-3 nucleotides, such as 2 nucleotides. The antisense strand may also have a 5' phosphate.

In another embodiment, the antisense strand is modified for Dicer processing by suitable modifiers located at the 3' end of the antisense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in dNMPs. Other nucleotide modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, 1-3 nucleotide modifiers, or 2 nucleotide modifiers are substituted for the ribonucleotides on the 3' end of the antisense strand. When sterically hindered molecules are utilized, they are attached to the ribonucleotide at the 3' end of the antisense strand. Thus, the length of the strand does not change with the incorporation of the modifiers. In another embodiment, the invention contemplates substituting two DNA bases in the dsRNA to direct the orientation of Dicer processing. In a further invention, two terminal DNA bases are located on the 3' end of the antisense strand in place of two ribonucleotides forming a blunt end of the duplex on the 5' end of the sense strand and the 3' end of the antisense strand, and a two-nucleotide RNA overhang is located on the 3'-end of the sense strand. This is an asymmetric composition with DNA on the blunt end and RNA bases on the overhanging end.

The sense and antisense strands anneal under biological conditions, such as the conditions found in the cytoplasm of a cell. In addition, a region of one of the sequences, particularly of the antisense strand, of the dsRNA has a sequence length of at least 19 nucleotides, wherein these nucleotides are adjacent to the 3' end of antisense strand and are sufficiently complementary to a nucleotide sequence of the RNA produced from the target gene.

Further in accordance with this embodiment, the dsRNA, i.e., the precursor RNAi molecule, may also have one or more of the following additional properties: (a) the antisense strand has a right shift from the typical 21mer and (b) the strands may not be completely complementary, i.e., the strands may contain simple mismatch pairings. A "typical" 21mer siRNA is designed using conventional techniques, such as described above. This 21mer is then used to design a right shift to include 1-7 additional nucleotides on the 5' end of the 21mer. The sequence of these additional nucleotides may have any sequence. Although the added ribonucleotides may be complementary to the target gene sequence, full complementarity between the target sequence and the antisense siRNA is not required. That is, the resultant antisense siRNA is sufficiently complementary with the target sequence. The first and second oligonucleotides are not required to be completely complementary. They only need to be substantially complementary to anneal under biological conditions and to provide a substrate for Dicer that produces a siRNA sufficiently complementary to the target sequence.

In one embodiment, the dsRNA has an asymmetric structure, with the antisense strand having a 25-base pair length, and the sense strand having a 27-base pair length with a 1-4 base 3'-overhang. In another embodiment, this dsRNA having an asymmetric structure further contains 2 deoxynucleotides at the 3' end of the antisense strand.

Suitable dsRNA compositions that contain two separate oligonucleotides can be linked by a third structure. The third structure will not block Dicer activity on the dsRNA and will not interfere with the directed destruction of the RNA transcribed from the target gene. In one embodiment, the third structure may be a chemical linking group. Many suitable chemical linking groups are known in the art and can be used. Alternatively, the third structure may be an oligonucleotide that links the two oligonucleotides of the dsRNA is a manner such that a hairpin structure is produced upon annealing of the two oligonucleotides making up the dsRNA composition. The hairpin structure will not block Dicer activity on the dsRNA and will not interfere with the directed destruction of the RNA transcribed from the target gene.

One feature of the dsRNA compositions of the present invention is that they can serve as a substrate for Dicer. Typically, the dsRNA compositions of this invention will not have been treated with Dicer, other RNases, or extracts that contain them. In the current invention this type of pretreatment can prevent Dicer annealing. Several methods are known and can be used for determining whether a dsRNA composition serves as a substrate for Dicer. For example, Dicer activity can be measured in vitro using the Recombinant Dicer Enzyme Kit (GTS, San Diego, Calif.) according to the manufacturer's instructions. Dicer activity can be measured in vivo by treating cells with dsRNA and maintaining them for 24 h before harvesting them and isolating their RNA. RNA can be isolated using standard methods, such as with the RNeasy™ Kit (Qiagen) according to the manufacturer's instructions. The isolated RNA can be separated on a 10% PAGE gel which is used to prepare a standard RNA blot that can be probed with a suitable labeled deoxyoligonucleotide, such as an oligonucleotide labeled with the Starfire® Oligo Labeling System (Integrated DNA Technologies, Inc., Coralville, Iowa).

The effect that a dsRNA has on a cell can depend upon the cell itself. In some circumstances a dsRNA could induce apoptosis or gene silencing in one cell type and not another. Thus, it is possible that a dsRNA could be suitable for use in one cell and not another. To be considered "suitable" a dsRNA composition need not be suitable under all possible circumstances in which it might be used, rather it need only be suitable under a particular set of circumstances.

Modifications can be included in the dsRNA, i.e., the precursor RNAi molecule, of the present invention so long as the modification does not prevent the dsRNA composition from serving as a substrate for Dicer. In one embodiment, one or more modifications are made that enhance Dicer processing of the dsRNA. In a second embodiment, one or more modifications are made that result in more effective RNAi generation. In a third embodiment, one or more modifications are made that support a greater RNAi effect. In a fourth embodiment, one or more modifications are made that result in greater potency per each dsRNA molecule to be delivered to the cell. Modifications can be incorporated in the 3'-terminal region, the 5'-terminal region, in both the 3'-terminal and 5'-terminal region or in some instances in various positions within the sequence. With the restrictions noted above in mind any number and combination of modifications can be incorporated into the dsRNA. Where multiple modifications are present, they may be the same or different. Modifications to bases, sugar moieties, the phosphate backbone, and their combinations are contemplated. Either 5'-terminus can be phosphorylated.

Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like (see, e.g., Amarzguioui et al., 2003). Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Locked nucleic acids, or LNA's, could also be incorporated. Many other modifications are known and can be used so long as the above criteria are satisfied. Examples of modifications are also disclosed in U.S. Pat. Nos. 5,684,143, 5,858,988 and 6,291,438 and in U.S. published patent application No. 2004/0203145 A1, each incorporated herein by reference. Other modifications are disclosed in Herdewijn (2000), Eckstein (2000), Rusckowski et al. (2000), Stein et al. (2001); Vorobjev et al. (2001).

One or more modifications contemplated can be incorporated into either strand. The placement of the modifications in the DsiRNA can greatly affect the characteristics of the DsiRNA, including conferring greater potency and stability, reducing toxicity, enhance Dicer processing, and minimizing an immune response. In one embodiment, the antisense strand or the sense strand or both strands have one or more 2'-O-methyl modified nucleotides. In another embodiment, the antisense strand contains 2'-O-methyl modified nucleotides. In another embodiment, the antisense stand contains a 3' overhang that is comprised of 2'-O-methyl modified nucleotides. The antisense strand could also include additional 2'-O-methyl modified nucleotides.

Additionally, the dsRNA structure can be optimized to ensure that the oligonucleotide segment generated from Dicer's cleavage will be the portion of the oligonucleotide that is most effective in inhibiting gene expression. For example, in one embodiment of the invention a 27-bp oligonucleotide of the dsRNA structure is synthesized wherein the anticipated 21 to 22-bp segment that will inhibit gene expression is located on the 3'-end of the antisense strand. The remaining bases located on the 5'-end of the antisense strand will be cleaved by Dicer and will be discarded. This cleaved portion can be homologous (i.e., based on the sequence of the target sequence) or non-homologous and added to extend the nucleic acid strand.

In one embodiment, the sense strand comprises 24-26 nucleotides, wherein the 2 nucleotides on the 3' end of the sense strand are deoxyribonucleotides. The sense strand contains a phosphate at the 5' end. The antisense strand comprises 26-29 nucleotides and contains a 3' overhang of 1-4 nucleotides. The nucleotides comprising the 3' overhang are modified with 2'-O-methyl. The antisense strand contains alternating 2'-O-methyl modified nucleotides beginning at the first monomer of the antisense strand adjacent to the 3' overhang, and extending 15-19 nucleotides from the first monomer adjacent to the 3' overhang, whereby the remaining 21-22 base pair antisense strand post-Dicer cleavage will contain the modified nucleotides. For example, for a 27 nucleotide antisense strand and counting the first base at the 5'-end of the antisense strand as position number 1, 2'OMe modifications would be placed at bases 9, 11, 13, 15, 17, 19, 21, 23, 25, 26, and 27 In one embodiment, the DsiRNA comprises:

```
5' pXXXXXXXXXXXXXXXXXXXXXXXDD

3' YXXXXXXXXXXXXXXXXXXXXXXXXXXp
``` wherein "X"=RNA, "p"=a phosphate group, "X"=2'-O-methyl modified RNA, "Y" is an overhang domain comprised of 1-4 RNA monomers that are optionally 2'-O-methyl RNA monomers, and "D"=DNA. The top strand is the sense strand, and the bottom strand is the antisense strand.

RNA may be produced enzymatically or by partial/total organic synthesis, and modified ribonucleotides can be introduced by in vitro enzymatic or organic synthesis. In one embodiment, each strand is prepared chemically. Methods of synthesizing RNA molecules are known in the art, in particular, the chemical synthesis methods as described in Verma and Eckstein (1998) or as described herein.

As is known, RNAi methods are applicable to a wide variety of genes in a wide variety of organisms and the disclosed compositions and methods can be utilized in each of these contexts. Examples of genes which can be targeted by the disclosed compositions and methods include endogenous genes which are genes that are native to the cell or to genes that are not normally native to the cell. Without limitation these genes include oncogenes, cytokine genes, idiotype (Id) protein genes, prion genes, genes that expresses molecules that induce angiogenesis, genes for adhesion molecules, cell surface receptors, proteins involved in metastasis, proteases, apoptosis genes, cell cycle control genes, genes that express EGF and the EGF receptor, multi-drug resistance genes, such as the MDR1 gene.

More specifically, the target mRNA of the invention specifies the amino acid sequence of a cellular protein (e.g., a nuclear, cytoplasmic, transmembrane, or membrane-associated protein). In another embodiment, the target mRNA of the invention specifies the amino acid sequence of an extracellular protein (e.g., an extracellular matrix protein or secreted protein). As used herein, the phrase "specifies the amino acid sequence" of a protein means that the mRNA sequence is translated into the amino acid sequence according to the rules of the genetic code. The following classes of proteins are listed for illustrative purposes: developmental proteins (e.g., adhesion molecules, cyclin kinase inhibitors, Wnt family members, Pax family members, Winged helix family members, Hox family members, cytokines/lymphokines and their receptors, growth/differentiation factors and their receptors, neurotransmitters and their receptors); oncogene-encoded proteins (e.g., ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES); tumor suppressor proteins (e.g., APC, BRCA1, BRCA2, MADH4, MCC, NF I, NF2, RB I, TP53, and WTI); and enzymes (e.g., ACC synthases and oxidases, ACP desaturases and hydroxylases, ADP-glucose pyrophorylases, ATPases, alcohol dehydrogenases, amylases, amyloglucosidases, catalases, cellulases, chalcone synthases, chitinases, cyclooxygenases, decarboxylases, dextriinases, DNA and RNA polymerases, galactosidases, glucanases, glucose oxidases, granule-bound starch synthases, GTPases, helicases, hemicellulases, integrases, inulinases, invertases, isomerases, kinases, lactases, lipases, lipoxygenases, lysozymes, nopaline synthases, octopine synthases, pectinesterases, peroxidases, phosphatases, phospholipases, phosphorylases, phytases, plant growth regulator synthases, polygalacturonases, proteinases and peptidases, pullanases, recombinases, reverse tranScriptases, RUBISCOs, topoisomerases, and xylanases).

In one aspect, the target mRNA molecule of the invention specifies the amino acid sequence of a protein associated with a pathological condition. For example, the protein may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. Pathogens include RNA viruses such as flaviviruses, picornaviruses, rhabdoviruses, filoviruses, retroviruses, including lentiviruses, or DNA viruses such as adenoviruses, poxviruses, herpes viruses, cytomegaloviruses, hepadnaviruses or others. Additional pathogens include bacteria, fungi, helminths, schistosomes and trypanosomes. Other kinds of pathogens can include mammalian transposable elements. Alternatively, the protein may be a tumor-associated protein or an autoimmune disease-associated protein.

The target gene may be derived from or contained in any organism. The organism may be a plant, animal, protozoa, bacterium, virus or fungus. See e.g., U.S. Pat. No. 6,506, 559, incorporated herein by reference.

In another aspect, the present invention provides for a pharmaceutical composition comprising the dsRNA of the present invention. The dsRNA sample can be suitably formulated and introduced into the environment of the cell by any means that allows for a sufficient portion of the sample to enter the cell to induce gene silencing, if it is to occur. Many formulations for dsRNA are known in the art and can be used so long as dsRNA gains entry to the target cells so that it can act. See, e.g., U.S. published patent application Nos. 2004/0203145 A1 and 2005/0054598 A1, each incorporated herein by reference. For example, dsRNA can be formulated in buffer solutions such as phosphate buffered saline solutions, liposomes, micellar structures, and capsids. Formulations of dsRNA with cationic lipids can be used to facilitate transfection of the dsRNA into cells. For example, cationic lipids, such as lipofectin (U.S. Pat. No. 5,705,188, incorporated herein by reference), cationic glycerol derivatives, and polycationic molecules, such as polylysine (published PCT International Application WO 97/30731, incorporated herein by reference), can be used. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

It can be appreciated that the method of introducing dsRNA into the environment of the cell will depend on the type of cell and the make up of its environment. For example, when the cells are found within a liquid, one preferable formulation is with a lipid formulation such as in lipofectamine and the dsRNA can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate dsRNA in a buffer or saline solution and directly inject the formulated dsRNA into cells, as in studies with oocytes. The direct injection of dsRNA duplexes may also be done. For suitable methods of introducing dsRNA see U.S. published patent application No. 2004/0203145 A1, incorporated herein by reference.

Suitable amounts of dsRNA must be introduced and these amounts can be empirically determined using standard methods. Typically, effective concentrations of individual dsRNA species in the environment of a cell will be about 50 nanomolar or less 10 nanomolar or less, or compositions in which concentrations of about 1 nanomolar or less can be used. In other embodiment, methods utilize a concentration of about 200 picomolar or less and even a concentration of about 50 picomolar or less can be used in many circumstances.

The method can be carried out by addition of the dsRNA compositions to any extracellular matrix in which cells can live provided that the dsRNA composition is formulated so that a sufficient amount of the dsRNA can enter the cell to exert its effect. For example, the method is amenable for use with cells present in a liquid such as a liquid culture or cell growth media, in tissue explants, or in whole organisms, including animals, such as mammals and especially humans.

Expression of a target gene can be determined by any suitable method now known in the art or that is later developed. It can be appreciated that the method used to measure the expression of a target gene will depend upon the nature of the target gene. For example, when the target gene encodes a protein the term "expression" can refer to a protein or transcript derived from the gene. In such instances the expression of a target gene can be determined by measuring the amount of mRNA corresponding to the target gene or by measuring the amount of that protein. Protein can be measured in protein assays such as by staining or immunoblotting or, if the protein catalyzes a reaction that can be measured, by measuring reaction rates. All such methods are known in the art and can be used. Where the gene product is an RNA species expression can be measured by determining the amount of RNA corresponding to the gene product. Several specific methods for detecting gene expression are described in Example 1. The measurements can be made on cells, cell extracts, tissues, tissue extracts or any other suitable source material.

The determination of whether the expression of a target gene has been reduced can be by any suitable method that can reliably detect changes in gene expression. Typically, the determination is made by introducing into the environment of a cell undigested dsRNA such that at least a portion of that dsRNA enters the cytoplasm and then measuring the expression of the target gene. The same measurement is made on identical untreated cells and the results obtained from each measurement are compared.

The dsRNA can be formulated as a pharmaceutical composition which comprises a pharmacologically effective amount of a dsRNA and pharmaceutically acceptable carrier. A pharmacologically or therapeutically effective amount refers to that amount of a dsRNA effective to produce the intended pharmacological, therapeutic or preventive result. The phrases "pharmacologically effective amount" and "therapeutically effective amount" or simply "effective amount" refer to that amount of an RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA composition may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration. In some embodiments, the pharmaceutical compositions are administered by intravenous or intraparenteral infusion or injection.

In general a suitable dosage unit of dsRNA will be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Pharmaceutical composition comprising the dsRNA can be administered once daily. However, the therapeutic agent may also be dosed in dosage units containing two, three, four, five, six or more sub-doses administered at appropriate intervals throughout the day. In that case, the dsRNA contained in each sub-dose must be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. In this embodiment, the dosage unit contains a corresponding multiple of the daily dose. Regardless of the formulation, the pharmaceutical composition must contain dsRNA in a quantity sufficient to inhibit expression of the target gene in the animal or human being treated. The composition can be compounded in such a way that the sum of the multiple units of dsRNA together contain a sufficient dose.

Data can be obtained from cell culture assays and animal studies to formulate a suitable dosage range for humans. The dosage of compositions of the invention lies within a range of circulating concentrations that include the $ED_{50}$ (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the $IC_{50}$ (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

In a further aspect, the present invention relates to a method for treating a subject having a disease or at risk of developing a disease caused by the expression of a target gene. In this embodiment, the dsRNA can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method comprises administering a pharmaceutical composition of the invention to the patient (e.g., human), such that expression of the target gene is silenced. Because of their high specificity, the dsRNAs of the present invention specifically target mRNAs of target genes of diseased cells and tissues.

In the prevention of disease, the target gene may be one which is required for initiation or maintenance of the disease, or which has been identified as being associated with a higher risk of contracting the disease. In the treatment of disease, the dsRNA can be brought into contact with the cells or tissue exhibiting the disease. For example, dsRNA substantially identical to all or part of a mutated gene associated with cancer, or one expressed at high levels in tumor cells, e.g. aurora kinase, may be brought into contact with or introduced into a cancerous cell or tumor gene.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state of condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

The present invention can also be used to treat a variety of immune disorders, in particular those associated with overexpression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, the invention relates to a method for treating viral diseases, including but not limited to human papilloma virus, hepatitis C, hepatitis B, herpes simplex virus (HSV), HIV-AIDS, poliovirus, and smallpox virus. dsRNAs of the invention are prepared as described herein to target expressed sequences of a virus, thus ameliorating viral activity and replication. The molecules can be used in the treatment and/or diagnosis of viral infected tissue, both animal and plant. Also, such molecules can be used in the treatment of virus-associated carcinoma, such as hepatocellular cancer.

The dsRNA of the present invention can also be used to inhibit the expression of the multi-drug resistance 1 gene ("MDR1"). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs and Ling, 1994). Moreover, expression of Pgp has been linked to the development of MDR in human cancer, particularly in the leukemias, lymphomas, multiple myeloma, neuroblastoma, and soft tissue sarcoma (Fan et al.). Recent studies showed that tumor cells expressing MDR-associated protein (MRP) (Cole et al., 1992), lung resistance protein (LRP) (Scheffer et al., 1995) and mutation of DNA topoisomerase II (Beck, 1989) also may render MDR.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Anand, 1992; Guthrie and Fink, 1991; Harlow and Lane, 1988, *Antibodies*, (Cold Spring Harbor Laboratory Press, Cold Spring Harbor, N.Y.); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish (Danio rerio)*, (4th Ed., Univ. of Oregon Press, Eugene, 2000).

EXAMPLES

The present invention is described by reference to the following Examples, which are offered by way of illustration and are not intended to limit the invention in any manner Standard techniques well known in the art or the techniques specifically described below were utilized.

Example 1

Preparation of Double-Stranded RNA Oligonucleotides

Oligonucleotide Synthesis and Purification

RNA oligonucleotides were synthesized using solid phase phosphoramidite chemistry, deprotected and desalted on NAP-5 columns (Amersham Pharmacia Biotech, Piscataway, N.J.) using standard techniques (Damha and Olgivie, 1993; Wincott et al., 1995). The oligomers were purified using ion-exchange high performance liquid chromatography (IE-HPLC) on an Amersham Source 15Q column (1.0 cm×25 cm) (Amersham Pharmacia Biotech, Piscataway, N.J.) using a 15 mM step-linear gradient. The gradient varied from 90:10 Buffers A:B to 52:48 Buffers A:B, where Buffer A was 100 mM Tris pH 8.5 and Buffer B was 100 mM Tris pH 8.5, 1 M NaCl. Samples were monitored at 260 nm and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 μm inner diameter and contained ssDNA 100R Gel (Beckman-Coulter). Typically, about 0.6 nmole of oligonucleotide was injected into a capillary, ran in an electric field of 444 V/cm and detected by UV absorbance at 260 nm Denaturing Tris-Borate-7 M-urea running buffer was purchased from Beckman-Coulter. Oligoribonucleotides were at least 90% pure as assessed by CE for use in experiments described below. Compound identity was verified by matrix-assisted laser desorption ionization time-of-flight (MALDI-TOF) mass spectroscopy on a Voyager DE™ Biospectrometry Work Station (Applied Biosystems, Foster City, Calif.) following the manufacturer's recommended protocol. Relative molecular masses of all oligomers were within 0.2% of expected molecular mass.

Preparation of Duplexes

Single-stranded RNA (ssRNA) oligomers were resuspended at 100 μM concentration in duplex buffer consisting of 100 mM potassium acetate, 30 mM HEPES, pH 7.5. Complementary sense and antisense strands were mixed in equal molar amounts to yield a final solution of 50 μM duplex. Samples were heated to 95° C. for 5' and allowed to cool to room temperature before use. Double-stranded RNA (dsRNA) oligomers were stored at −20° C. Single-stranded RNA oligomers were stored lyophilized or in nuclease-free water at −80° C.

Nomenclature

For consistency, the following nomenclature has been employed throughout the specification and Examples. Names given to duplexes indicate the length of the oligomers and the presence or absence of overhangs. A "21+2" duplex contains two RNA strands both of which are 21 nucleotides in length, also termed a 21mer siRNA duplex, and having a 2 base 3'-overhang. A "21-2" design is a 21mer siRNA duplex with a 2 base 5'-overhang. A 21-0 design is a 21mer siRNA duplex with no overhangs (blunt). A "21+2UU" is a 21mer duplex with 2-base 3'-overhang and the terminal 2 bases at the 3'-ends are both U residues (which may result in mismatch with target sequence). A "25/27" is an asymmetric duplex having a 25 base sense strand and a 27 base antisense strand with a 2-base 3'-overhang. A "27/25" is an asymmetric duplex having a 27 base sense strand and a 25 base antisense strand.

Example 2

Increased Potency of 25Mers

This example demonstrates that dsRNAs having strands that are 25 nucleotides in length or longer have surprisingly increased potency in mammalian systems than known 21mer to 23mer siRNAs.

During investigations of the effects of different 5' and 3' end structures of dsRNAs made through bacteriophage T7 in vitro transcription (Kim et al., 2004), we observed that some seemed to have greater potency than synthetic 21mer siRNAs directed to the same target site, and that this property seemed to correlate with length. To further explore this phenomenon, we systematically studied the silencing properties of chemically synthesized duplex RNAs of different lengths and designs.

Cell Culture, Transfection, and EGFP Assays

HEK 293 cells were split in 24-well plates to 60% confluency in DMEM medium 1 d before transfection. After adding the aliquot of each RNA, 50 μl of Opti Media containing the reporter vectors was added. Next, 50 μl of Opti Media containing 1.5 μl of Lipofectamine 2000 (Invitrogen) was mixed and incubated for 15 min. The cells were then added in 0.4 ml of DMEM medium. To normalize for transfection efficiency, each assay included cotransfection of the target and/or duplex RNAs with either firefly luciferase or a red fluorescent protein (RFP) reporter plasmid (all other assays). For the luciferase assay, the Steady Glo Luciferase assay kit was used according to manufacturer's instructions (Promega). For RFP cotransfection, the indicated amount of EGFP reporter plasmid (pLEGFP-C1 vector, Clontech) was transfected with 20 ng of RFP reporter plasmid (pDsRed2-C1, BD Sciences). After 24 h, RFP expression was monitored by fluorescence microscopy. Only experiments where transfection efficiency was >90% (as assessed by RFP expression) were evaluated. EGFP expression was measured 24 h later. EGFP expression was determined either from the median number of EGFP-fluorescent cells determined by FACS (live cells) or by fluorometer readings (cell extracts).

For EGFP assays using NIH3T3 cells stably expressing EGFP, measurements were determined using a VersaFluor Fluorometer (Bio-Rad) using excitation filter D490 and emission filter D520. Before transfections, cells were seeded to approximately 30% confluency in a 24-well plate. On day 0, cells were transfected as described above and the medium was changed on day 1 after transfection. The first EGFP assay was carried out on day 3. For extract preparation $1 \times 10^5$ cells were taken and $1 \times 10^4$ cells were further propagated for the day 6 EGFP assays. On days 6 and 9 the same procedure was repeated.

Extract measurements of EGFP were obtained as follows: $1 \times 10^5$ cells were suspended in 300 μl of PBS and sonicated for 10 s followed by a 2-min microcentrifugation. The supernatants were used for fluorescence measurements. Percentages of EGFP expression were determined relative to extracts prepared from untreated NIH3T3 cells.

Nucleic Acid Reagents

The reporter system employed EGFP either as a transfection plasmid vector pEGFP-C1 (Clontech, Palo Alto, Calif.) or as a stable transformant in an NIH 3T3 cell line. The coding sequence of EGFP is shown in Table 1, from Genbank accession #U55763. The ATG start codon and TAA stop codons are highlighted in bold font and sites target by siRNA reagents in this Example and other Examples are underscored.

TABLE 1

| Nucleotide Sequence of EGFP |
|---|
| atggtgagcaagggcgaggagctgttcaccggggtggtgcccatcctgg |
| tcgagctggacggcgacgtaaacggccacaagttcagcgtgtccggcga |
| gggcgaggcgatgccacctacg<u>gcaagctgaccctgaagttcatctgc</u> |
| <u>accaccggcaagc</u>tgcccgtgccctggcccaccctcgtgaccaccctga |
| cctacggcgtgcagtgcttcagccgctaccccgaccac<u>atgaagcagca</u> |
| <u>cgacttcttcaagtccgccatg</u>cccgaaggctacgtccaggagcgcacc |
| atcttcttcaaggacgacggcaactacaagacccgcgccgaggt<u>gaagt</u> |
| <u>tcgagggcgacaccctggtgaaccgcat</u>cgagctgaagggcatcgactt |

TABLE 1-continued

Nucleotide Sequence of EGFP caaggaggacggcaacatcctggggcacaagctggagtacaactacaac agccacaacgtctatatcatggccgacaagcagaagaacggcatcaagg tgaacttcaagatccgccacaacatcgaggacggcagcgtgcagctcgc cgaccactaccagcagaacaccccatcggcgacggccccgtgctgctg cccgacaaccactacctgagcacccagtccgccctgagcaaagacccca acgagaagcgcgatcacatggtcctgctggagttcgtgaccgccgccgg gatcactctcggcatggacgagctgtacaagtaa
(SEQ ID NO: 1)

Site-1 used for siRNA targeting in EGFP for this example was:

SITE 1:
(SEQ ID NO: 2)
5' GCAAGCUGACCCUGAAGUUCAUCUGCACCACCGGCAAGC 3'.

RNA duplexes were synthesized and prepared as described in Example 1. RNA duplexes targeting EGFP Site-1 are summarized in Table 2. Some sequences had the dinucleotide sequence "UU" placed at the 3'-end of the sense strand (Elbashir et al., 2001c; Hohjoh, 2002). Mismatches that resulted from including 3'-terminal "UU" or where a mismatch was intentionally positioned are highlighted in bold and underscored.

TABLE 2

Summary of Oligonucleotide Reagents, EGFP Site-1

| Sequence | Name | SEQ ID NO. |
| --- | --- | --- |
| 5' GCAAGCUGACCCUGAAGUUCAUCUGCACCACCGGCAAGC 3' | EGFP Site-1 | SEQ ID NO: 2 |
| 5' GCAAGCUGACCCUGAAGUUCA<br>3' UUCGACUGGGACUUCAAGUAG | EGFPS1-21 − 2 | SEQ ID No: 3<br>SEQ ID No: 4 |
| 5' AAGCUGACCCUGAAGUUCAUC<br>3' UUCGACUGGGACUUCAAGUAG | EGFPS1-21 + 0 | SEQ ID No: 5<br>SEQ ID No: 6 |
| 5' CCUGAAGUUCAUCUGCACCAC<br>3' UGGGACUUCAAGUAGACGUGG | EGFPS1-21 + 2(1) | SEQ ID No: 7<br>SEQ ID No: 8 |
| 5' CCCUGAAGUUCAUCUGCACCA<br>3' CUGGGACUUCAAGUAGACGUG | EGFPS1-21 + 2(2) | SEQ ID No: 9<br>SEQ ID No: 10 |
| 5' ACCCUGAAGUUCAUCUGCACC<br>3' ACUGGGACUUCAAGUAGACGU | EGFPS1-21 + 2(3) | SEQ ID No: 11<br>SEQ ID No: 12 |
| 5' GACCCUGAAGUUCAUCUGCAC<br>3' GACUGGGACUUCAAGUAGACG | EGFPS1-21 + 2(4) | SEQ ID No: 13<br>SEQ ID No: 14 |
| 5' UGACCCUGAAGUUCAUCUGCA<br>3' CGACUGGGACUUCAAGUAGAC | EGFPS1-21 + 2(5) | SEQ ID No: 15<br>SEQ ID No: 16 |
| 5' CUGACCCUGAAGUUCAUCUGC<br>3' UCGACUGGGACUUCAAGUAGA | EGFPS1-21 + 2(6) | SEQ ID No: 17<br>SEQ ID No: 18 |
| 5' GCUGACCCUGAAGUUCAUCUG<br>3' UUCGACUGGGACUUCAAGUAG | EGFPS1-21 + 2(7) | SEQ ID No: 19<br>SEQ ID No: 20 |
| 5' GCAAGCUGACCCUGAAGUUCAUU<br>3' UUCGACUGGGACUUCAAGUAGAC | EGFPS1-23 − 2UU | SEQ ID No: 21<br>SEQ ID No: 22 |
| 5' GCUGACCCUGAAGUUCAUCUGUU<br>3' UUCGACUGGGACUUCAAGUAGAC | EGFPS1-23 + 2UU | SEQ ID No: 23<br>SEQ ID No: 24 |
| 5' GCAAGCUGACCCUGAAGUUCAUUU<br>3' UUCGACUGGGACUUCAAGUAGACG | EGFPS1-24 − 2UU | SEQ ID No: 25<br>SEQ ID No: 26 |
| 5' GCUGACCCUGAAGUUCAUCUGCUU<br>3' UUCGACUGGGACUUCAAGUAGACG | EGFPS1-24 + 2UU | SEQ ID No: 27<br>SEQ ID No: 28 |
| 5' GCAAGCUGACCCUGAAGUUCAUCUU<br>3' UUCGACUGGGACUUCAAGUAGACGU | EGFPS1-25 − 2UU | SEQ ID No: 29<br>SEQ ID No: 30 |
| 5' GCUGACCCUGAAGUUCAUCUGCAUU<br>3' UUCGACUGGGACUUCAAGUAGACGU | EGFPS1-25 + 2UU | SEQ ID No: 31<br>SEQ ID No: 32 |
| 5' AAGCUGACCCUGAAGUUCAUCUGCAC<br>3' UUCGACUGGGACUUCAAGUAGACGUG | EGFPS1-26 + 0 | SEQ ID No: 33<br>SEQ ID No: 34 |
| 5' AAGCUGACCCUGAAGUUCAUCUGCUU<br>3' UUCGACUGGGACUUCAAGUAGACGUG | EGFPS1-26 + 0UU | SEQ ID No: 35<br>SEQ ID No: 36 |

TABLE 2-continued

Summary of Oligonucleotide Reagents, EGFP Site-1

| Sequence | Name | SEQ ID NO. |
|---|---|---|
| 5' GCAAGCUGACCCUGAAGUUCAUCUUU<br>3' UUCGACUGGGACUUCAAGUAGACGUG | EGFPS1-26 - 2UU | SEQ ID No: 37<br>SEQ ID No: 38 |
| 5' GCUGACCCUGAAGUUCAUCUGCACUU<br>3' UUCGACUGGGACUUCAAGUAGACGUG | EGFPS1-26 + 2UU | SEQ ID No: 39<br>SEQ ID No: 40 |
| 5' AAGCUGACCCUGAAGUUCAUCUGCACC<br>3' UUCGACUGGGACUUCAAGUAGACGUGG | EGFPS1-27 + 0 | SEQ ID No: 41<br>SEQ ID No: 42 |
| 5' F-AAGCUGACCCUGAAGUUCAUCUGCACC<br>3' UUCGACUGGGACUUCAAGUAGACGUGG-F | EGFPS1-27 + 0<br>FAM #1 | SEQ ID No: 43<br>SEQ ID No: 44 |
| 5' AAGCUGACCCUGAAGUUCAUCUGCACC-F<br>3' UUCGACUGGGACUUCAAGUAGACGUGG-F | EGFPS1-27 + 0<br>FAM #2 | SEQ ID No: 45<br>SEQ ID No: 44 |
| 5' F-AAGCUGACCCUGAAGUUCAUCUGCACC<br>3' F-UUCGACUGGGACUUCAAGUAGACGUGG | EGFPS1-27 + 0<br>FAM #4 | SEQ ID No: 43<br>SEQ ID No: 46 |
| 5' AAGCUGACCCUGAAGUUCAUCUGCACC-F<br>3' F-UUCGACUGGGACUUCAAGUAGACGUGG | EGFPS1-27 + 0<br>FAM #5 | SEQ ID No: 45<br>SEQ ID No: 46 |
| 5' AAGCUGACCCUGAAGUUCAUCUGCAUU<br>3' UUCGACUGGGACUUCAAGUAGACGUGG | EGFPS1-27 + 0UU | SEQ ID No: 47<br>SEQ ID No: 48 |
| 5' GCAAGCUGACCCUGAAGUUCAUCUGUU<br>3' UUCGACUGGGACUUCAAGUAGACGUGG | EGFPS1-27 - 2UU | SEQ ID No: 49<br>SEQ ID No: 50 |
| 5' GCUGACCCUGAAGUUCAUCUGCACAUU<br>3' UUCGACUGGGACUUCAAGUAGACGUGG | EGFPS1-27 + 2UU/<br>25 | SEQ ID No: 51<br>SEQ ID No: 52 |
| 5' AAGCUGACCCUGAAGAUCAUCUGCAUU<br>3' UUCGACUGGGACUUCUAGUAGACGUGG | EGFPS1-27 + 0UU/<br>16 | SEQ ID No: 53<br>SEQ ID No: 54 |
| 5' AAGCUGACCCUGAAGAACAUCUGCAUU<br>3' UUCGACUGGGACUUCUUGUAGACGUGG | EGFPS1-27 + 0UU/<br>16, 17 | SEQ ID No: 55<br>SEQ ID No: 56 |
| 5' AAGCUGACCCUGAACAACAUCUGCAUU<br>3' UUCGACUGGGACUUGUUGUAGACGUGG | EGFPS1-27 + 0UU/<br>15, 16, 17 | SEQ ID No: 57<br>SEQ ID No: 58 |
| 5' AAGCUGACCCUGUUCAUCAUCUGCACC<br>3' UUCGACUGGGACAAGUAGUAGACGUGG | EGFPS1-27 + 0-mut | SEQ ID No: 59<br>SEQ ID No: 60 |
| 5' AAGCUGACCCUGAAGUUCAUCUGCACCA<br>3' UUCGACUGGGACUUCAAGUAGACGUGGU | EGFPS1-28 + 0 | SEQ ID No: 61<br>SEQ ID No: 62 |
| 5' AAGCUGACCCUGAAGUUCAUCUGCACCAC<br>3' UUCGACUGGGACUUCAAGUAGACGUGGUG | EGFPS1-29 + 0 | SEQ ID No: 63<br>SEQ ID No: 64 |
| 5' AAGCUGACCCUGAAGUUCAUCUGCACCACC<br>3' UUCGACUGGGACUUCAAGUAGACGUGGUGG | EGFPS1-30 + 0 | SEQ ID No: 65<br>SEQ ID No: 66 |
| 5' AAGCUGACCCUGAAGUUCAUCUGCACCACCGGCAA<br>3' UUCGACUGGGACUUCAAGUAGACGUGGUGGCCGUU | EGFPS1-35 + 0 | SEQ ID NO: 67<br>SEQ ID NO: 68 |
| 5' AAGCUGACCCUGAAGUUCAUCUGCACCACCGGCAAGCUGC<br>3' UUCGACUGGGACUUCAAGUAGACGUGGUGGCCGUUCGACG | EGFPS1-40 + 0 | SEQ ID NO: 69<br>SEQ ID NO: 70 |
| 5' AAGCUGACCCUGAAGUUCAUCUGCACCACCGGCAAGCUGCCCGUG<br>3' UUCGACUGGGACUUCAAGUAGACGUGGUGGCCGUUCGACGGGCAC | EGFPS1-45 + 0 | SEQ ID NO: 71<br>SEQ ID NO: 72 |

Results

An expanded set of synthetic RNA duplexes of varying length containing 3' overhangs, 5' overhangs or blunt ends were tested for their relative potency in a model system targeting site 1' in EGFP (Kim et al., 2003). We carried out our initial transfections using 50 nM of the various RNA duplexes (FIG. 1A). The real potency of the longer duplexes was shown only when transfections were done at subnanomolar concentrations. Using duplex RNA concentrations of 200 pM (FIG. 1B) and 50 pM (FIG. 1C), we observed that potency increased with length. Blunt, 5'-overhanging and 3'-overhanging ends were of similar potency. Increased potencies of the longer duplex RNAs were observed even in the NIH3T3 cells stably expressing EGFP (FIG. 1F). Duplexes longer than 27 nt were synthesized and tested for RNAi efficacy (FIG. 1D). Maximal inhibitory activity was seen at a duplex length of 27 bp (FIG. 1D). Longer duplexes showed progressive loss of functional RNAi activity and by 40-45 bp were wholly inactive at the tested concentrations, which also correlated with poor in vitro cleavage of these duplexes by Dicer (FIG. 1E).

Example 3

Dicer Substrates

This example demonstrates a method for determining whether a dsRNA serves as a substrate for Dicer.

In Vitro Dicer Cleavage Assays

RNA duplexes (100 pmol) were incubated in 20 μl of 20 mM Tris pH 8.0, 200 mM NaCl, 2.5 mM $MgCl_2$ with 1 unit of recombinant human Dicer (Stratagene) for 24 h. A 3 μl aliquot of each reaction (15 pmol RNA) was separated in a 15% nondenaturing polyacrylamide gel, stained with GelStar (Ambrex) and visualized using UV excitation.

Results

Figure 2A:
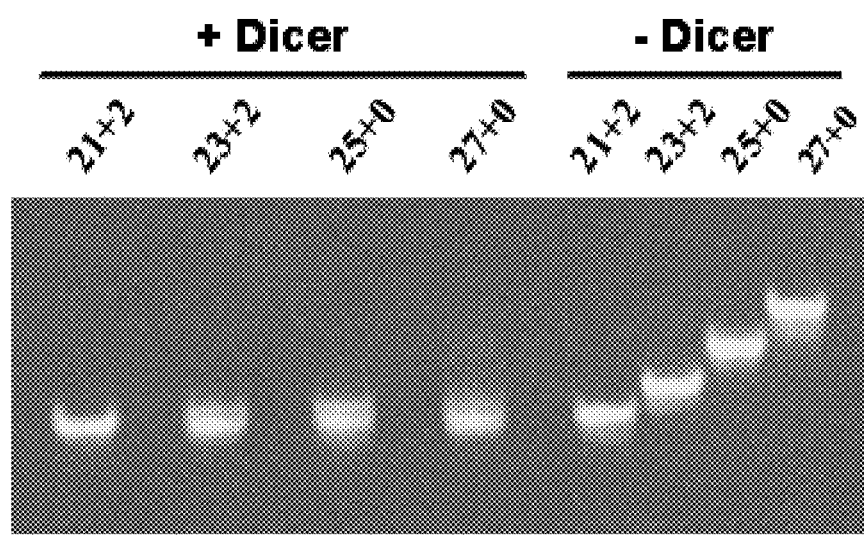
FIGS. 2A-2E show that Dicer processing correlates with RNAi activity.

Incubation of 21-bp to 27-bp RNA duplexes with recombinant human Dicer resulted in cleavage of the 23mer, 25mer and 27mer duplexes, but not the 21mer duplex (FIG. 2A). Determinations of relative efficiencies of Dicer cleavage were not possible under the in vitro conditions recommended by the supplier owing to the slow kinetics of this reaction. Aside from the possibility that the dsRNAs longer than 30 bp may need to be preprocessed by Drosha, a micro RNA processing enzyme, to be good substrates for Dicer, we do not have an explanation for why these longer dsRNAs are both poor substrates for Dicer and poor triggers for RNAi.

Example 4

Effect of End-Modification on Dicer Activity

The effect of end-modification of dsRNA was tested using the in vitro Dicer cleavage assay described in Example 3.

Figure 2B:
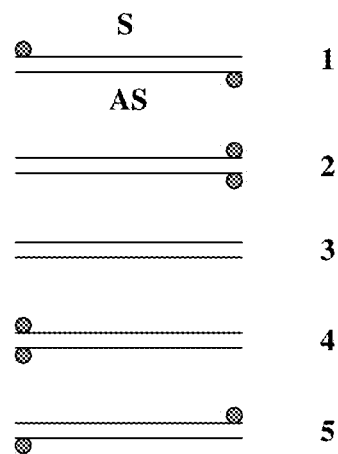
Figure 2C:
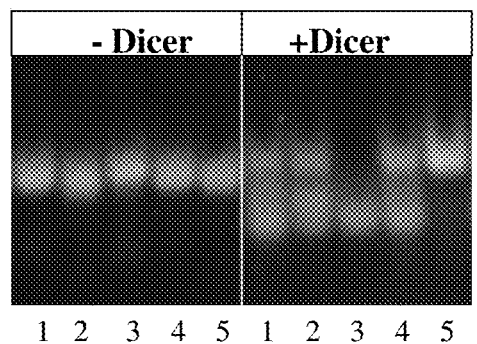
Figure 2D:
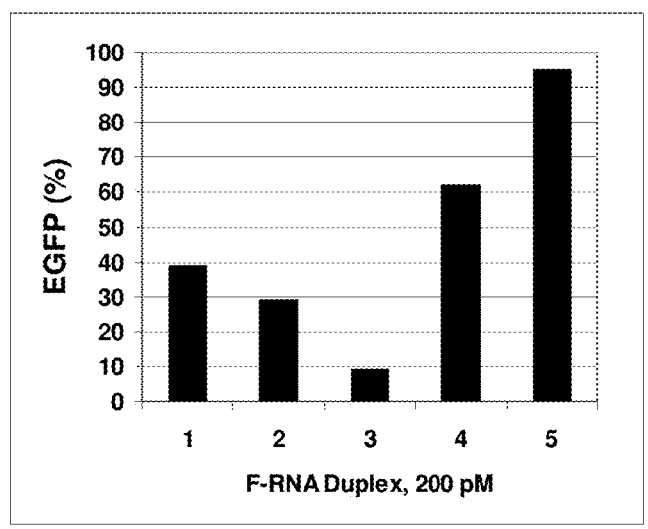

For the 27mer duplexes, we tested the effects of fluorescein end-modification on Dicer activity and the ability to trigger RNAi silencing. RNA oligonucleotides were synthesized for the EGFPS1 site with 6-carboxyfluorescein (6FAM) attached to the 5' end of the sense (S) strand, 3' end of the S-strand, 5' end of the antisense (AS) strand and 3' end of the AS strand. Pairwise combinations were used to make duplex RNAs (FIG. 2B). Duplex 3 was the unmodified wild-type EGFPS1 27+0 duplex. The structure of the 6FAM modified duplexes are shown in Table 2. RNA duplexes were incubated for 24 h with recombinant human Dicer, separated by nondenaturing polyacrylamide gel electrophoresis (PAGE), stained and visualized by UV excitation (FIG. 2C). Unlike in earlier experiments, in which RNA duplexes were fully cleaved during a 24-h incubation (FIG. 2A), all of the modified duplexes showed some degree of resistance to cleavage by Dicer. Only the unmodified wild-type sequence (duplex 3) was fully cleaved in the in vitro Dicer reaction. The duplex bearing a 3'-6FAM on the S strand and a 3'-6FAM on the AS strand (duplex 5) was totally resistant to cleavage under these conditions. Functional potencies of these five duplexes were compared in EGFP cotransfection assays (FIG. 2D) using 200 pM RNA concentrations. Parallel to the patterns seen for in vitro Dicer cleavage, all of the 27mer duplexes with 6FAM-modified ends were less potent than the unmodified duplexes in reducing EGFP expression. Duplexes 1, 2 and 4, which showed partial cleavage with recombinant Dicer, had three- to six-fold reduced RNAi activity. Duplex 5, which showed no cleavage with recombinant Dicer, had minimal RNAi activity, establishing a direct correlation between the relative effectiveness of in vitro cleavage by Dicer and RNAi in cell culture.

Example 5

In Vivo Processing by Dicer

This example confirms that the 27mer dsRNA are processed in vivo by Dicer.

Assay for Intracellular Processing of 27Mer RNAs

RNA duplexes were transfected as described above into HEK293 cells in a six-well plate at 10 nM. After 14 h, total RNA was prepared as described below. First, 20 μg of total RNA was heated for 10 min at 75° C. and mixed with $^{32}P$ 5'-end-labeled oligonucleotide probe (5'-ACCCTGAAGT-TCATCTGCACC-3'; SEQ ID NO:73) and hybridized in 150 mM NaCl, 50 mM Tris-HCl, pH. 7.4, 1 mM EDTA) at 24° C. Samples were loaded on 7.5% nondenaturing polyacrylamide gel and separated at 200 V for 3 h at 4° C., and the gel was exposed to X-ray film. $^{32}P$-end-labeled 27mer and 21mer duplex RNA oligos were used as size standards.

Results

Figure 2E:
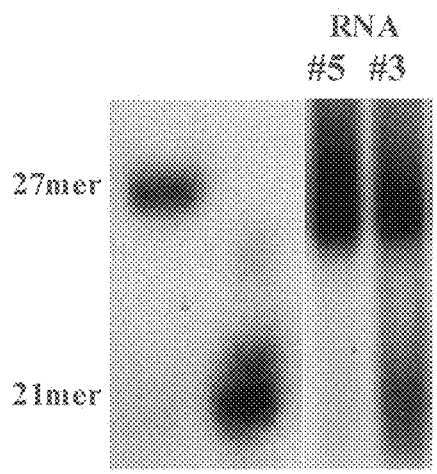

To confirm that the 27mer dsRNAs are processed by Dicer in vivo, we transfected HEK293 cells with 10 nM of the duplex 3 (unmodified) or duplex 5 (both 3' ends modified with 6FAM). After 14 h, total RNA was isolated and hybridized with a $^{32}P$ end labeled 21mer probe oligo (S strand). RNA was separated by nondenaturing PAGE and visualized by autoradiography (FIG. 2E). Similar to the results seen with in vitro Dicer cleavage, in RNA prepared from cells transfected with duplex 3 (unmodified 27mer), a smaller species was observed migrating with a 21mer duplex marker, consistent with Dicer cleavage product. This 21mer species was not detected in RNA from cells transfected with duplex 5 (3' end-modified 27mer).

Example 6

Potency of dsRNAs

This example examines the potency of potential cleavage products of the 27mer by Dicer.

Figure 3A:
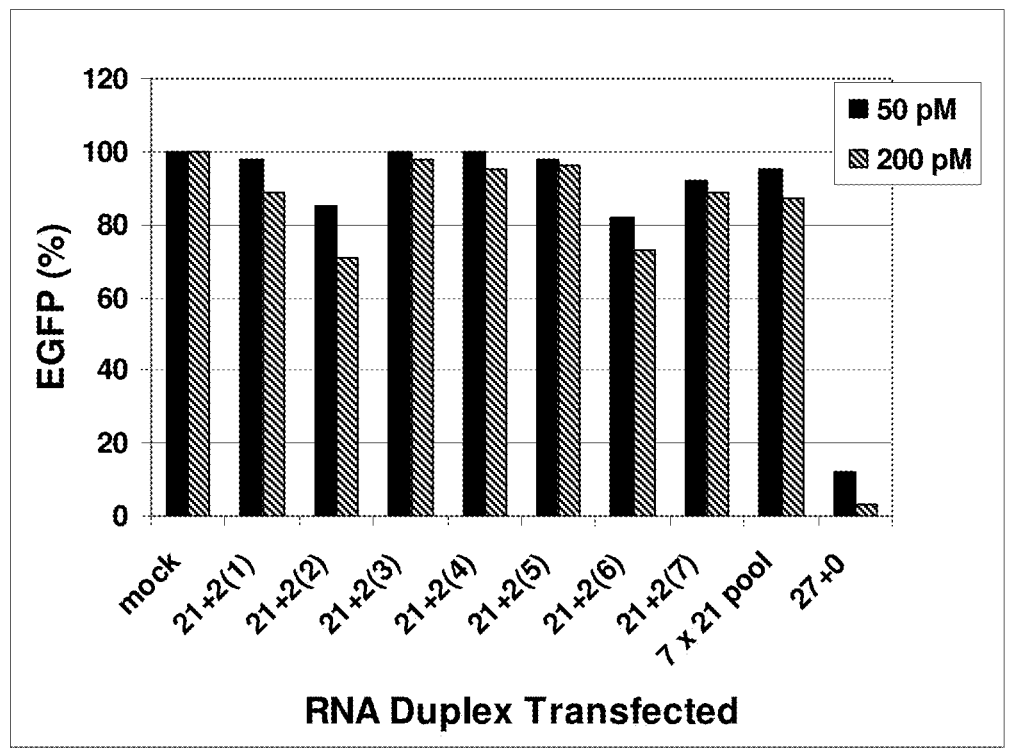
FIG. 3A-3B show RNAi activity of various 21+2 siRNAs.
Figure 3B:
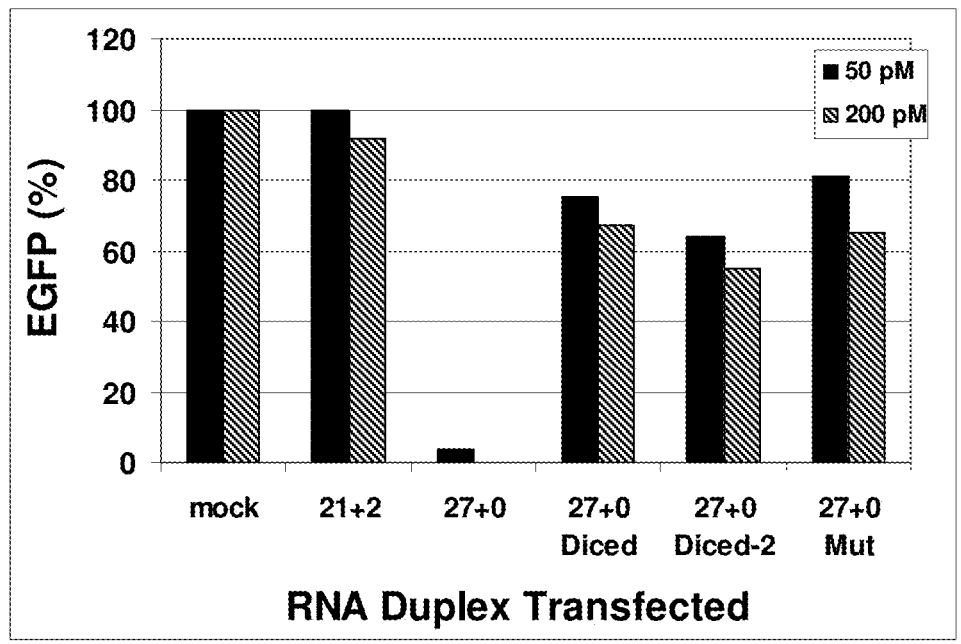

Cleavage of a 27mer by Dicer could result in a variety of distinct 21mers depending on where cleavage occurs; it is possible that one or a mix of these possible 21mers is significantly more potent than the specific 21mer that we used as our standard for comparison. To test this possibility we synthesized seven different 21mers that could be derived from the EGFPS1 27+0 duplex, walking in single-base steps along the antisense strand, using the traditional 21+2 design. These seven duplexes were tested for RNAi activity in the HEK293 cell cotransfection assay individually and as a pool (FIG. 3A). At concentrations of 50 or 200 pM, neither the individual 21mer duplexes nor the pooled set of seven 21mer duplexes showed activity comparable to the 27mer duplex. In vitro Dicer cleavage of the 27mers before transfection did not significantly enhance efficacy (FIG. 3B). As an additional control, we transfected a mutated EGFP 27mer duplex (Table 2), EGFPS1-27+0/mut) harboring four consecutive, centrally placed mismatched bases. The mismatches virtually eliminated any RNAi activity (FIG. 3B).

Example 7

Analysis of Dicer Cleavage Products

This example analyzed the in vitro Dicer cleavage products by mass spectroscopy.

Electrospray-Ionization Liquid Chromatography Mass Spectroscopy

Electrospray-ionization liquid chromatography mass spectroscopy (ESI-LCMS) of duplex RNAs before and after treatment with Dicer were done using an Oligo HTCS system (Novatia), which consisted of ThermoFinnigan TSQ7000, Xcalibur data system, ProMass data processing software and Paradigm MS4 HPLC (Michrom BioResources). The liquid chromatography step used before injection into the mass spectrometer (LC-MS) removes most of the cations complexed with the nucleic acids; some sodium ions can remain bound to the RNA and are visualized as minor +22 or +44 species, reflecting the net mass gain seen with substitution of sodium for hydrogen.

Results

Figure 4A:
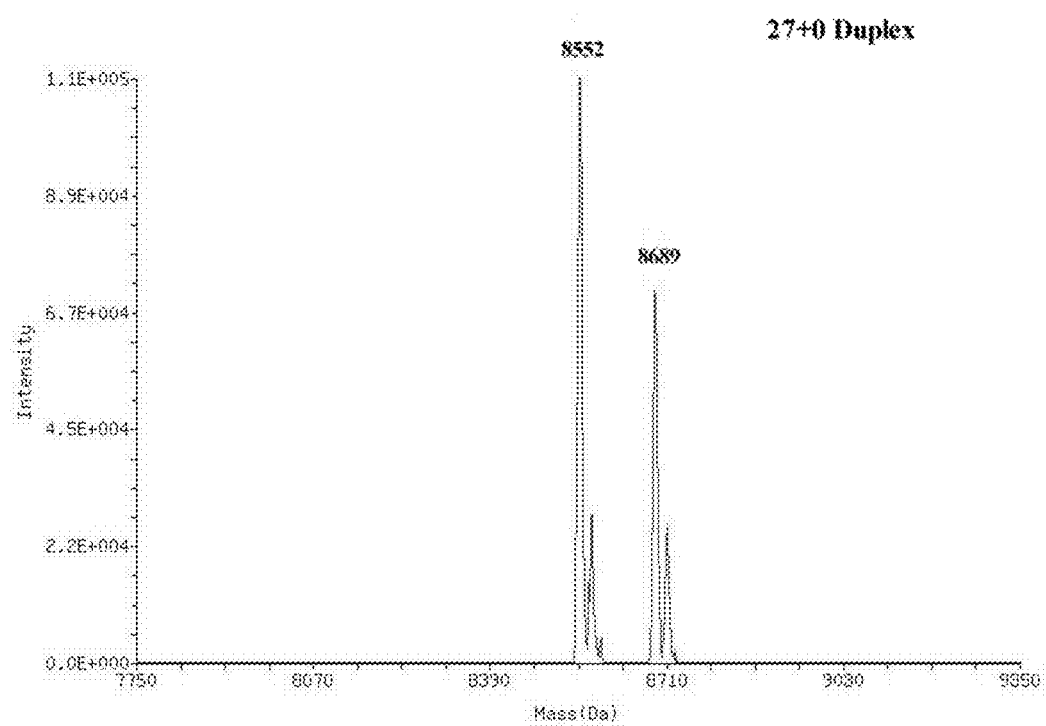
FIGS. 4A and 4B show ESI mass spectra of the 27mer duplex EGFPS1 27+0 before (FIG. 4A) and after (FIG. 4B) incubation with Dicer. Duplexes separate into single strands and the measured mass of each strand is indicated. Dicer digestion is performed in the presence of high salt and some "shadow" peaks represent +1 or +2 Na species.
Figure 4B:
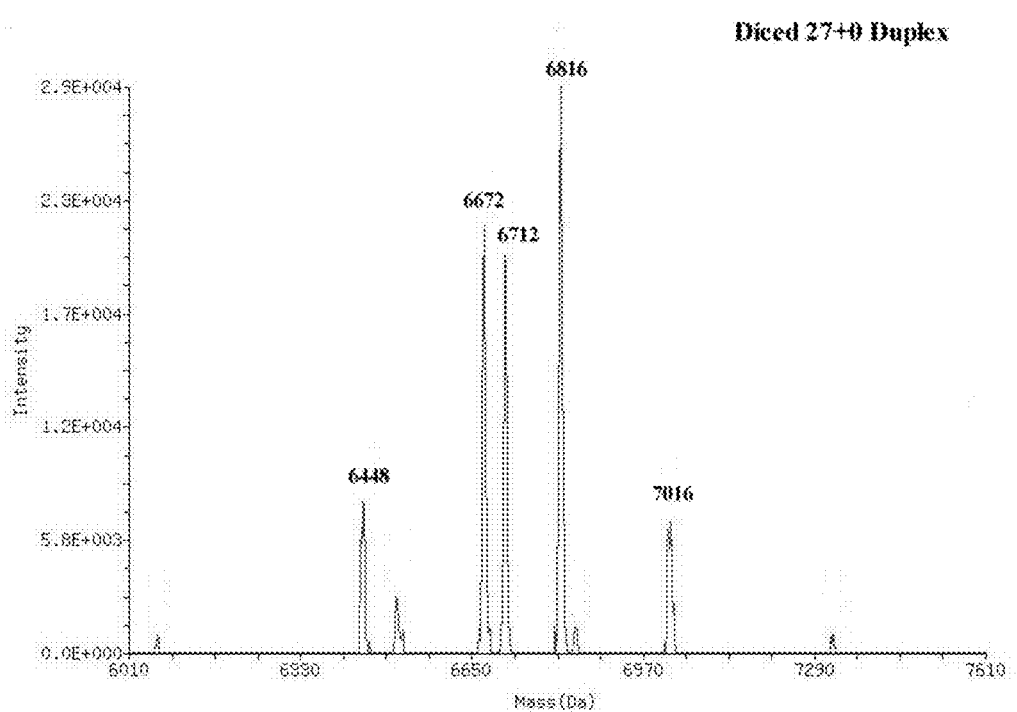
Figure 5A:
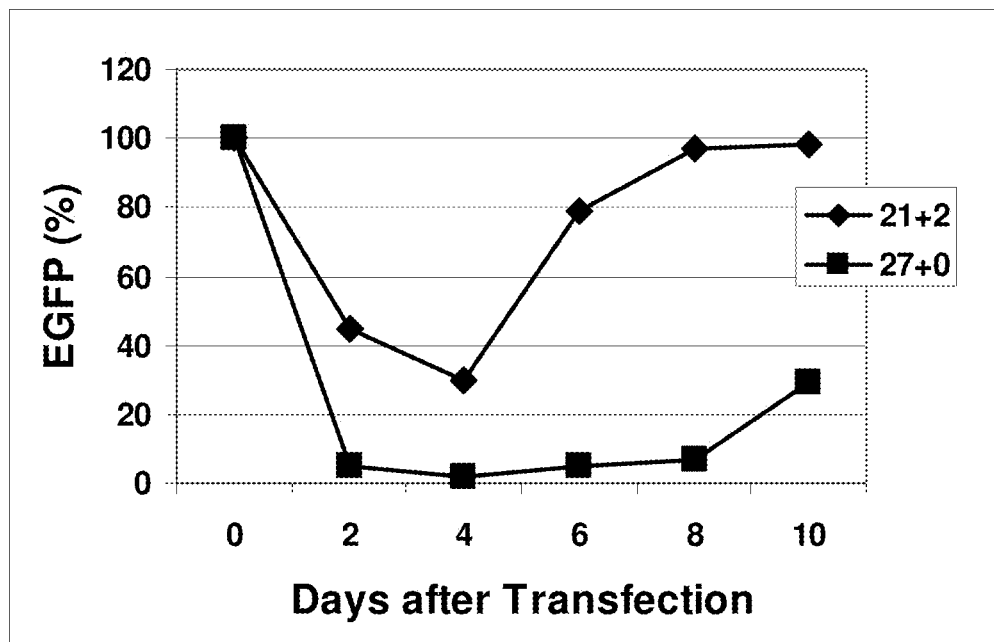
FIGS. 5A-5D show features of 27mer dsRNA in RNAi.

The species that are actually produced by incubation of the EGFPS1 27+0 duplex with recombinant Dicer in vitro were identified using electrospray ionization mass spectrometry (ESI MS) (FIGS. 4A and 4B). Calculated masses for each possible digestion product that could result from in vitro Dicer cleavage are shown in Table 3. The ESI MS analyses of the in vitro cleavage products are consistent with the known activity of this enzyme.

transfection. Cell extracts were prepared and measured for EGFP fluorescence using a fluorometer (FIG. 5A). EGFP suppression lasted approximately 4 d using the 21+2 siRNA, consistent with previous observations (Persengiev et al., 2004), whereas inhibition obtained with the 27+0 dsRNA persisted up to 10 d. A class of 'hyperfunctional' 21+2 siRNAs has been reported showing a similar extended duration of silencing (Reynolds et al., 2004); however, these sequences are rare and difficult to find or predict. Use of the 27mer dsRNA design may permit longer, more potent RNAi to be achieved at a greater variety of target sites.

Example 9

Effect of 27Mer dsRNA on Site Selection

A frequent problem in using RNAi as a tool to systematically inhibit the expression of any gene is that not all target sites are equally susceptible to suppression by siRNAs (Sherer and Rossi, 2004), necessitating complex design algorithms to predict effective sites (Reynolds et al., 2004; Ui-Tei et al., 2004; Amarzguioui and Prydz, 2004). We therefore asked whether the increased potency of the 27mer dsRNA permits effective targeting at sites that are not active using traditional 21mer siRNAs. Duplex RNAs were made having 21+2 and 27+0 designs to two sites in EGFP ('EGFP-S2' and 'EGFP-S3') both previously shown to be refractory to RNAi using standard siRNAs (Kime and Rossi, 2003).

TABLE 3

Molecular Weights of Possible 21mer Duplexes Derived from the 27mer Duplex by Dicer Processing

| Sequence (SEQ ID NO:) | Name | Mol Wt* |
|---|---|---|
| 5' AAGCUGACCCUGAAGUUCAUCUGCACC (41) | EGFPS1-27 + 0 | 8552 |
| 3' UUCGACUGGGACUUCAAGUAGACGUGG (42) | | 8689 |
| 5' ACCCUGAAGUUCAUCUGCACC (11) | EGFPS1-21 + 2(3) | 6672** |
| 3' ACUGGGACUUCAAGUAGACGU (12) | | 6816** |
| 5' GACCCUGAAGUUCAUCUGCAC (13) | EGFPS1-21 + 2(4) | 6712** |
| 3' GACUGGGACUUCAAGUAGACG (14) | | 6855 |
| 5' UGACCCUGAAGUUCAUCUGCA (15) | EGFPS1-21 + 2(5) | 6713** |
| 3' CGACUGGGACUUCAAGUAGAC (16) | | 6815** |
| 5' CUGACCCUGAAGUUCAUCUGC (17) | EGFPS1-21 + 2(6) | 6689 |
| 3' UCGACUGGGACUUCAAGUAGA (18) | | 6816** |
| 5' GCUGACCCUGAAGUUCAUCUG (19) | EGFPS1-21 + 2(7) | 6729 |
| 3' UUCGACUGGGACUUCAAGUAG (20) | | 6793 |

*Molecular weight of 27mer is the original chemically synthesized duplex with hydroxyl ends.
Calculated weights of 21mers assume 5'phosphate on each strand after Dicer Processing.
**Indicates masses that were consistent with visualized peaks in FIG. 4B.

Example 8

Further Characterization of Inhibitory Properties of 27Mer dsRNA

To further characterize the inhibitory properties of the 27mer dsRNA in cells stably expressing the EGFP target, stably transfected NIH3T3 cells expressing EGFP were transfected with 21+2 and 27+0 dsRNA duplexes (both at 5 nM). To obtain a quantitative estimate of the duration of gene suppression, we carried out a time-course experiment, observing EGFP expression on days 2, 4, 6, 8 and 10 after Nucleic Acid Reagents The reporter system employed EGFP as in SEQ ID NO:1 above. Site-2 (also termed bad site I) and Site-3 (also termed bad site 2) in EGFP were targeted. RNA duplexes were synthesized and prepared as described in Example 1. Site-2 and Site 3 used for siRNA targeting in EGFP for this example were:

SITE 2:
(SEQ ID NO: 74)
5' UGAAGCAGCACGACUUCUUCAAGUCCGCCAUG 3'
and

SITE 3:
(SEQ ID NO: 75)
5' UGAAGUUCGAGGGCGACACCCUGGUGAACCGCAU 3'.

RNA duplexes targeting EGFP Site-2 and EGFP Site-3 are summarized in Table 4.

TABLE 4

Summary of Oligonucleotide Reagents, EGFP Site-2

| Sequence | Name | SEQ ID NO: |
|---|---|---|
| 5' UGAAGCAGCACGACUUCUUCAAGUCCGCCAUG 3' | EGFP Site-2 | SEQ ID NO: 74 |
| 5' GCAGCACGACUUCUUCAAGUU<br>3' UUCGUCGUGCUGAAGAAGUUC | EGFPS2-21 + 2 | SEQ ID NO: 76<br>SEQ ID NO: 77 |
| 5' AAGCAGCACGACUUCUUCAAGUCCGCC<br>3' UUCGUCGUGCUGAAGAAGUUCAGGCGG | EGFPS2-27 + 0 | SEQ ID NO: 78<br>SEQ ID NO: 79 |
| 5' UGAAGUUCGAGGGCGACACCCUGGUGAACCGCAU 3' | EGFP Site-3 | SEQ ID NO: 75 |
| 5' GUUCGAGGGCGACACCCUGUU<br>3' UUCAAGCUCCCGCUCUGGGAC | EGFPS3-21 + 2 | SEQ ID NO: 80<br>SEQ ID NO: 81 |
| 5' GUUCGAGGGCGACACCCUGGUGAAC<u>UU</u><br>3' UUCAAGCUCCCGCUCUGGGACCACUUGGC | EGFPS3-27 + 0UU | SEQ ID NO: 82<br>SEQ ID NO: 83 |

Results

Figure 5B:
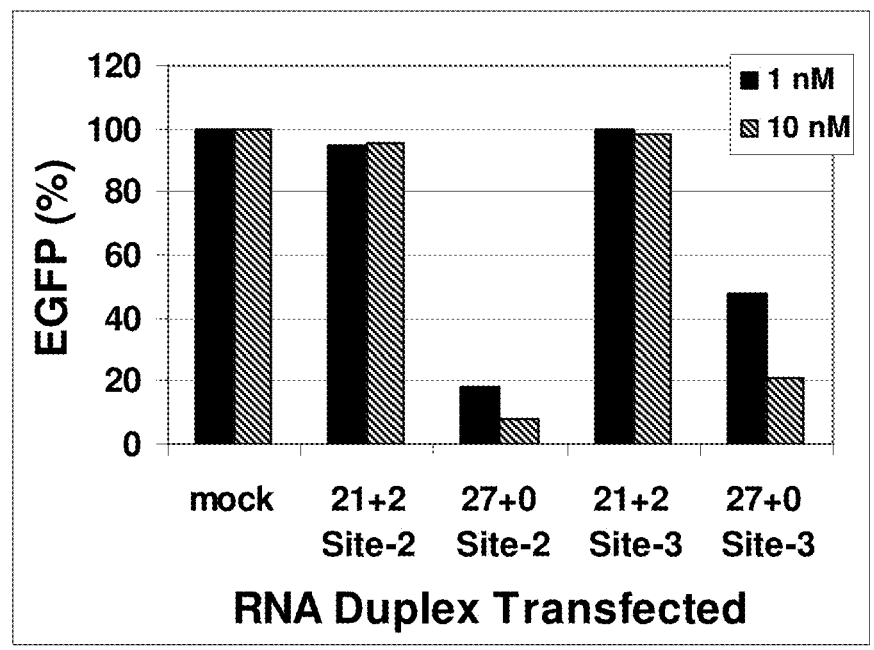

The duplexes were transfected into HEK293 cells using the cotransfection assay format (FIG. 5B) at 1 nM and 10 nM. At these doses, standard 21+2 siRNAs were ineffective at both sites, whereas the 27mer dsRNAs reduced EGFP expression by 80-90% at EGFP-S2 and by 50% (1 nM) and 80% (10 nM) at EGFP-S3. Despite the increased potency of Dicer substrate dsRNAs, empirical testing of target sites is still useful to find the most sensitive targets for RNAi. In this regard, it is important that Dicer products of some 27mers generated poorly functional siRNAs. By better understanding Dicer substrate preferences, it should be possible to design substrate RNAs that will generate the desired 21mers. We have observed that a two-base 3' overhang on only one end of the 27mer will preferentially guide Dicer to cleave 21-23 nt upstream of the two-base 3' overhang.

This example demonstrates that dsRNAs of the invention can efficiently target sites within the EGFP gene that were previously considered poor targets by previously known methods. Use of the method of the invention will therefore simplify site selection and design criteria for RNAi. This example also shows that the intentional placement of mismatches at the 3'-terminus of the sense strand increases the potency of the 27mer duplex.

Example 10

Effect of 27Mer dsRNA on Other Genes

To ensure that the increased potency of the 27mer dsR-NAs was not an artifact of targeting a reporter construct, we targeted two endogenous transcripts, human hnRNP H mRNA (Markovtsov et al., 2000) and mRNA encoding the La protein (Wolin and Cedervall, 2002).

RNAi Assays Against hnRNP H and La

HEK293 cells were plated to 30% confluency in a six-well plate. The next day, the cells were transfected with the indicated amount of dsRNA, and the medium was changed on the following day. The cells were harvested in 300 µl PBS 72 h after transfection. Extracts were prepared as described above for the EGFP assays. For western blots, 2 µl of cell extract was loaded on a 10% SDS-PAGE gel. Endogenous hnRNP H was detected using a rabbit polyclonal anti-hnRNP H antibody (Markovtsov et al., 2000) and anti-rabbit antibody conjugated to alkaline phosphatase (Sigma). β-Actin was detected with a mouse-derived anti-actin antibody (Sigma) and anti-mouse antibody conjugated to alkaline phosphatase (Sigma). For northern blot analyses, harvested cells were mixed with RNA STAT-60 (Tel-Test B) and total RNA was extracted according to the manufacturer's protocol. RNA was electrophoresed in a 6% denaturing polyacrylamide gel, transferred to a nylon membrane and probed with $^{32}$P-end-labeled oligos (La, 5'-CCAAAGGTACCCA-GCCTTCATCCAGTT-3' (SEQ ID NO:84); β-actin, 5'-GT-GAGGATGCCTCTCTTGCTCTGGGCCTCG-3' (SEQ ID NO:85)). Hybridizations were carried out in 10 ml of hybridization solution (1 ml 50×Denhardt's, 3 ml 20×SSPE, 0.5 ml 10% SDS) for 3 h at 37° C. After hybridization, the blot was washed three times with 2×SSPE at 37° C.

Nucleic Acid Reagents

The coding sequence of *Homo sapiens* heterogeneous nuclear ribonucleoprotein H (hnRPH) mRNA (Genbank accession No. NM_005520) is shown in Table 5. The ATG start codon and TAA stop codons are highlighted in bold font and site target by siRNA reagents is underscored.

TABLE 5

Nucleotide Sequence of HNRPH ttttttttttcgtcttagccacgcagaagtcgcgtgtctagtttgttt cgacgccggaccgcgtaagagacgatgatgttgggcacggaaggtgga gagggattcgtggtgaaggtccggggcttgccctggtcttgctcggcc gatgaagtgcagaggttttttttctgactgcaaaattcaaaatggggct caaggtattcgtttcatctacaccagagaaggcagaccaagtggcgag gcttttt<u>gttgaacttgaatcagaagatgaagtcaaattggc</u>cctgaaa aaagacagagaaactatgggacacagatatgttgaagtattcaagtca aacaacgttgaaatggattgggtgttgaagcatactggtccaaatagt cctgacacggccaatgatggctttgtacggcttagaggacttcccttt

TABLE 5-continued

Nucleotide Sequence of HNRPH ggatgtagcaaggaagaaattgttcagttcttctcagggttggaaatc
gtgccaaatgggataacattgccggtggacttccaggggaggagtacg
ggggaggccttcgtgcagtttgcttcacaggaaatagctgaaaaggct
ctaaagaaacacaaggaaagaatagggcacaggtatattgaaatcttt
aagagcagtagagctgaagttagaactcattatgatccaccacgaaag
cttatggccatgcagcggccaggtccttatgacagacctggggctggt
agagggtataacagcattggcagaggagctggctttgagaggatgagg
cgtggtgcttatggtggaggctatggaggctatgatgattacaatggc
tataatgatggctatggatttgggtcagatagatttggaagagacctc
aattactgttttcaggaatgtctgatcacagatacggggatggtggc
tctactttccagagcacaacaggacactgtgtacacatgcggggatta
ccttacagagctactgagaatgacatttataattttttttcaccgctc
aaccctgtgagagtacacattgaaattggtcctgatggcagagtaact
ggtgaagcagatgtcgagttcgcaactcatgaagatgctgtggcagct
atgtcaaaagacaaagcaaatgcaacacagatatgtagaactcttc
ttgaattctacagcaggagcaagcggtggtgcttacgaacacagatat
gtagaactcttcttgaattctacagcaggagcaagcggtggtgcttat
ggtagccaaatgatgggaggcatgggcttgtcaaaccagtccagctac
gggggcccagccagccagcagctgagtgggggttacggaggcggctac
ggtggccagagcagcatgagtggatacgaccaagttttacaggaaaac
tccagtgattttcaatcaaacattgcataggtaaccaaggagcagtga
acagcagctactacagtagtggaagccgtgcatctatgggcgtgaacg
gaatgggagggttgtctagcatgtccagtatgagtggtggatggggaa
tgtaattgatcgatcctgatcactgactcttggtcaacctttttttt
ttttttttttctttaagaaaacttcagtttaacagtttctgcaataca
agcttgtgatttatgcttactctaagtggaaatcaggattgttatgaa
gacttaaggcccagtattttgaatacaatactcatctaggatgtaac
agtgaagctgagtaaactataactgttaaacttaagttccagctttc
tcaagttagttataggatgtacttaagcagtaagcgtatttaggtaaa
agcagttgaattatgttaaatgttgcccttgccacgttaaattgaac
actgttttggatgcatgttgaaagacatgcttttattttttttgtaaa
acaatataggagctgtgtctactattaaaagtgaaacattttggcatg
tttgttaattctagtttcatttaataacctgtaaggcacgtaagttta
agcttttttttttttaagttaatgggaaaaatttgagacgcaatacc
aatacttaggattttggtcttggtgtttgtatgaaattctgaggcctt
gatttaaatcttcattgtattgtgatttccttttaggtatattgcgc
taagtgaaacttgtcaaataaatcctccttttaaaaactgc
(SEQ ID NO: 86)

The coding sequence of the La protein mRNA (Genbank accession No. NM_005520) is shown in Table 6. The ATG start codon and TAA stop codons are highlighted in bold font and site target by siRNA reagents is underscored.

TABLE 6

Nucleotide Sequence of La Protein ccggcggcgctggaggtggagtcgttgctgttgctgtttgtgagcc
tgtggcgcggcttctgtgggccggaaccttaaagatagccgtaatgg
ctgaaaatggtgataatgaaaagatggctgccctggaggccaaaatc
tgtcatcaaattgagtattattttggcgacttcaatttgccacggga
caagtttctaaaggaacag<u>ataaaactggatgaaggctgggtacctt</u>
<u>tggagat</u>aatgataaaattcaacaggttgaaccgtctaacaacagac
tttaatgtaattgtggaagcattgagcaaatccaaggcagaactcat
ggaaatcagtgaagataaaactaaaatcagaaggtctccaagcaaac
ccctacctgaagtgactgatgagtataaaaatgatgtaaaaaacaga
tctgtttatattaaaggcttcccaactgatgcaactcttgatgacat
aaaagaatggttagaagataaaggtcaagtactaaatattcagatga
gaagaacattgcataaagcatttaagggatcaatttttgttgtgttt
gatagcattgaatctgctaagaaatttgtagagaccccctggccagaa
gtacaaagaaacagacctgctaatacttttcaaggacgattactttg
ccaaaaaaatgaagaaagaaaacaaaataaagtggaagctaaatta
agagctaaacaggagcaagaagcaaaacaaaagttagaagaagatgc
tgaaatgaaatctctagaagaaaagattggatgcttgctgaaatttt
cgggtgatttagatgatcagacctgtagagaagatttacacatactt
ttctcaaatcatggtgaaataaaatggatagacttcgtcagaggagc
aaaagaggggataattctatttaaagaaaaagccaaggaagcattgg
gtaaagccaaagatgcaaataatggtaacctacaattaaggaacaaa
gaagtgacttgggaagtactagaaggagaggtggaaaaagaagcact
gaagaaaataatagaagaccaacaagaatccctaaacaaatggaagt
caaaaggtcgtagatttaaaggaaaaggaaagggtaataaagctgcc
cagcctgggtctggtaaaggaaaagtacagtttcagggcaagaaaac
gaaatttgctagtgatgatgaacatgatgaacatgatgaaaatggtg
caactggacctgtgaaaagagcaagagaagaaacagacaaagaagaa
cctgcatccaaacaacagaaaacagaaatggtgctggagaccagta
gtttagtaaaccaattttttattcattttaaataggttttaaacgac
ttttgtttgcgggcttttaaaaggaaaaccgaattaggtccacttc
aatgtccacctgtgagaaaggaaaaattttttttgttgtttaacttgt
cttttgttatgcaaatgagatttctttgaatgtattgttctgtttg
tgttatttcagatgattcaaatatcaaaaggaagattcttccattaa
attgcctttgtaatatgagaatgtattagtacaaactaactaataaa
atatatactatatgaaaagagc
(SEQ ID NO: 87)

RNA duplexes were synthesized and prepared as described in Example 1. RNA duplexes targeting HNRPH1 are summarized in Table 7.

TABLE 7

Summary of Oligonucleotide Reagents

| Sequence | Name | SEQ ID NO: |
|---|---|---|
| 5' GUUGAACUUGAAUCAGAAGAUGAAGUCAAAUUGGC 3' | HNRPH1 Site-1 | SEQ ID No: 88 |
| 5' CUUGAAUCAGAAGAUGAAGUU<br>3' UUGAACUUAGUCUUCUACUUC | HNRPH1-21 + 2 | SEQ ID No: 89<br>SEQ ID No: 90 |
| 5' AACUUGAAUCAGAAGAUGAAGUCAAAU<br>3' UUGAACUUAGUCUUCUACUUCAGUUUA | HNRPH1-27 + 0 | SEQ ID No: 91<br>SEQ ID No: 92 |
| 5' AUAAAACUGGAUGAAGGCUGGGUACCUUUGGAGAU 3' | La Site-1 | SEQ ID NO: 93 |
| 5' CUGGAUGAAGGCUGGGUACUU<br>3' UUGACCUACUUCCGACCCAUG | La-21 + 2 | SEQ ID NO: 94<br>SEQ ID NO: 95 |
| 5' AACUGGAUGAAGGCUGGGUACCUUUUU<br>3' UUGACCUACUUCCGACCCAUGGAAACC | La-21 + 2 | SEQ ID NO: 96<br>SEQ ID NO: 97 |

Results

Figure 5C:
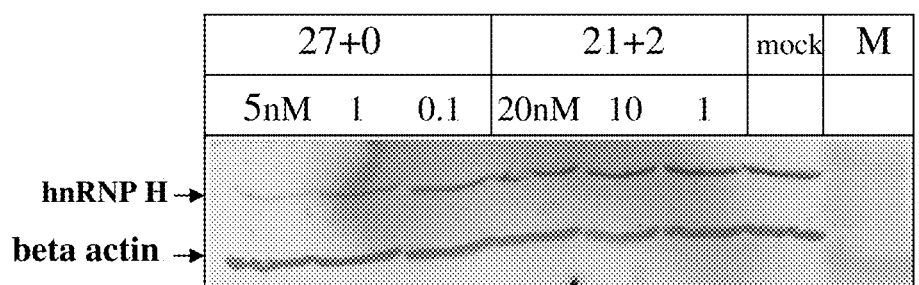
Figure 5D:
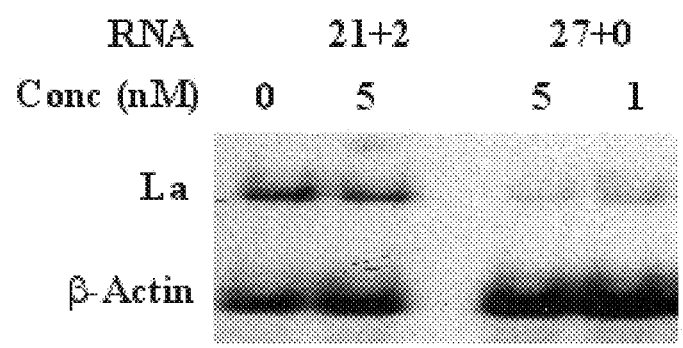

RNA duplexes were synthesized to target randomly chosen sites in the human hnRNP H mRNA (analyzed by western blotting) and the mRNA encoding the La protein (analyzed by northern blotting (FIGS. 5C and 5D). For both targets the 27mer duplex was more potent than the 21mer siRNAs targeting these messages.

Example 11

Sequence Specificity of 27Mer

Figure 6:
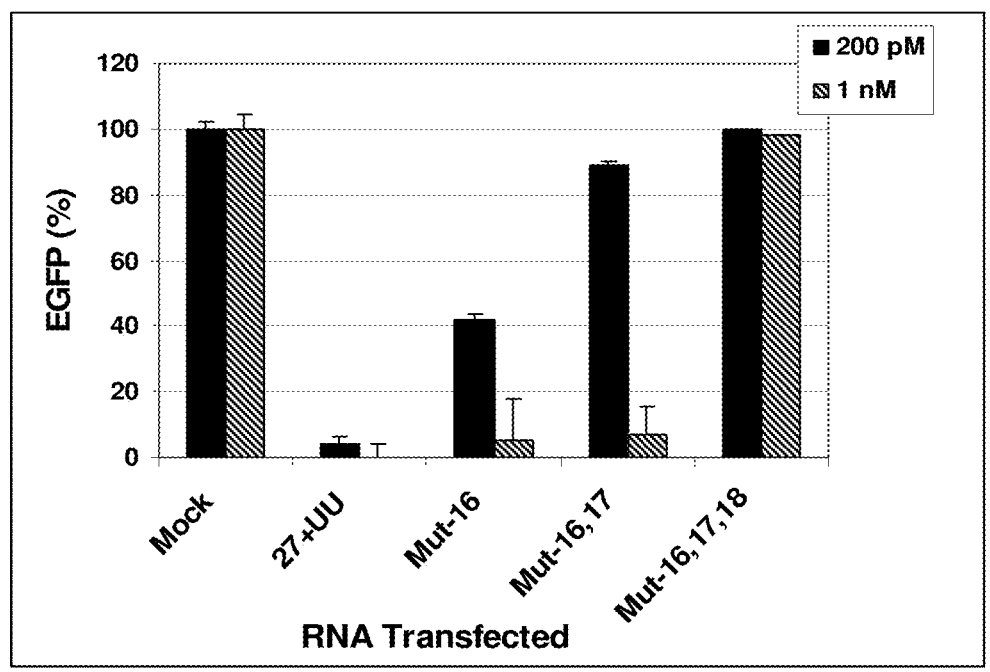
FIG. 6 shows sequence specificity of Dicer substrate 27mer dsRNAs. The various 27mer dsRNAs were co-transfected at the indicated concentrations with the EGFP expression plasmid into HEK93 cells and assayed for EGFP fluorescence.

As a test for the sequence specificity of the 27mer dsRNA, a series of 27+0 dsRNAs with one, two or three mismatches to the EGFP target mRNA were synthesized and tested at concentrations of 0 nM, 1 nM and 200 pM in the cotransfection assay (FIG. 6). The sequences of the mutated 27+0 dsRNAs are shown in Table 2. At 200 pM, each of the mismatched sequences was less potent than the wild-type 27mer dsRNA; the triple mismatch 27mer dsRNA was completely ineffective at triggering RNAi at all concentrations tested. Similar results were obtained using a 27mer dsRNA targeted to site 2' of EGFP.

Example 12

Lack of Interferon Response

This example demonstrates that the dsRNA duplexes of the invention do not activate the interferon response.

Interferon and PKR Assays

After transfection of 293 cells with 20 nM of each RNA as described previously, medium was collected after 24 h and used for ELISA assays of interferon α and β as previously described (Kim et al., 2004). The PKR activation assay was done as previously described (Gunnery and Mathews, 1998). PKR in the lysate was first activated by co-incubation of the indicated RNAs and radiolabeled by its auto-kinase reaction. The radiolabeled PKR was then immunoprecipitated for analysis. To determine the activity of PKR in the cell lysate without prior activation, dsRNA was omitted. The reaction was incubated at 30° C. for 20 min. PKR from the reaction was immunoprecipitated using polyclonal antibody. The polyclonal antibody was added to the reaction, which was then placed on ice for 1 h, followed by addition of 50 µl of 10% protein A-Sepharose in IPP500 (10 mM Tris, pH 8, 500 mM NaCl, 0.1% Nonidet P-40). This mixture was rocked for 30 min at 4° C. The protein A-Sepharose beads were washed with 1 ml IPP100 buffer (10 mM Tris, pH 8, 100 mM NaCl, 0.1% Nonidet P-40) five times. After the last wash, the beads were boiled in protein sample buffer and loaded onto an SDS-polyacrylamide gel followed by autoradiography.

Results

Figure 7A:
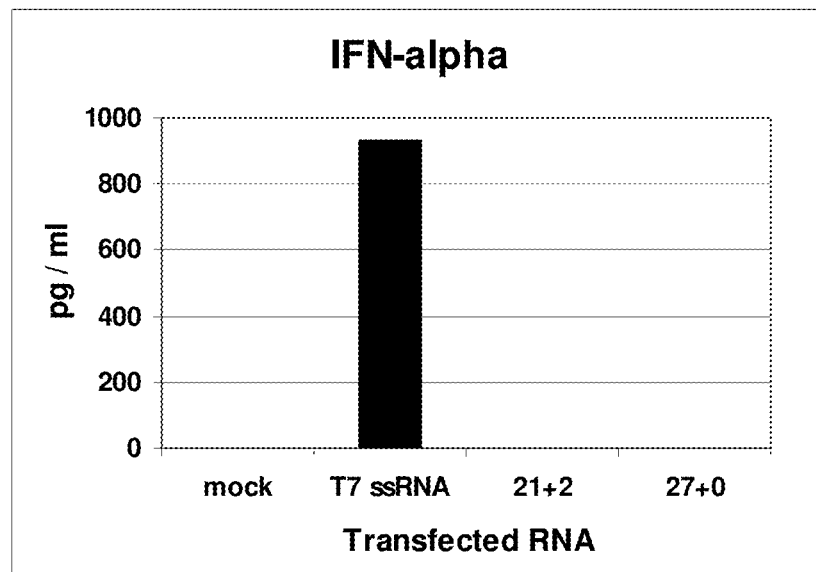
FIGS. 7A-7D show that siRNAs and Dicer substrate dsRNAs do not induce interferons or activate PKR or generate specific "off target effects.
Figure 7B:
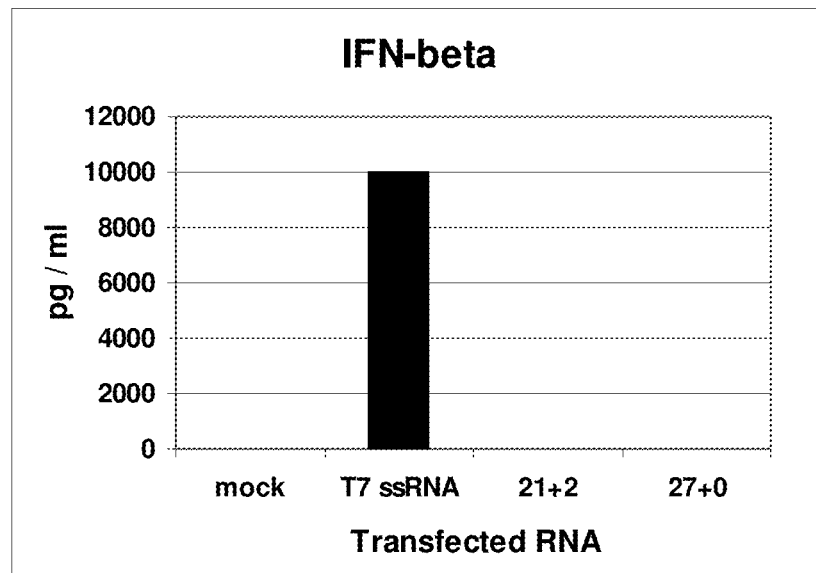
Figures 7C, 7D:
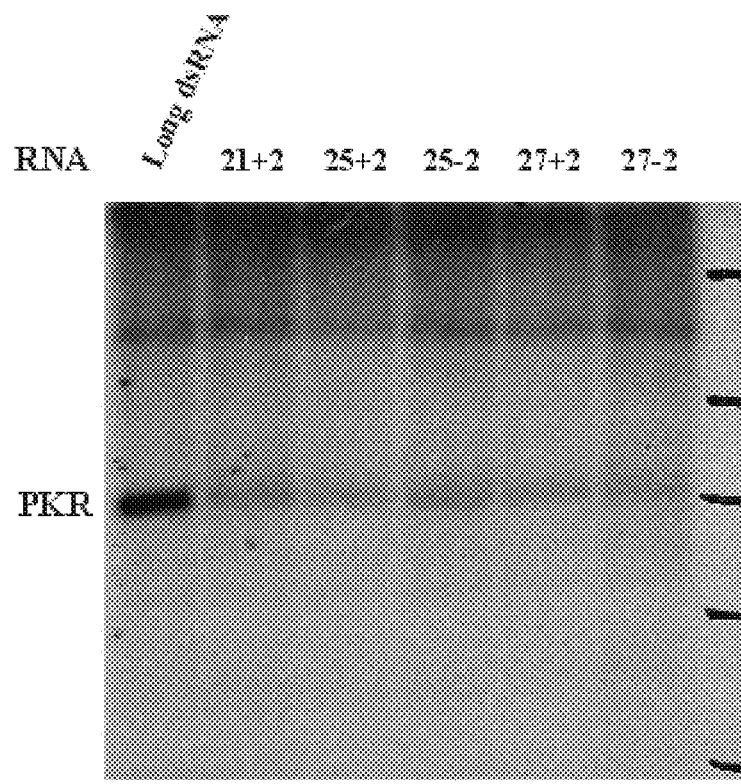

A potential problem in the use of the longer dsRNAs is activation of PKR and induction of interferons (Manche et al., 1992). We therefore assessed whether a transfected 27mer dsRNA activates interferon-α (FIG. 7A) or interferon-β (FIG. 7B). As a positive control for interferon induction, we transfected a triphosphate-containing single-stranded RNA which potently activated interferon-α and -β, as reported previously (Kim et al., 2004). Neither cytokine was detected when either the 21+2 siRNA or 27+0 dsRNA was used. We have extended this observation to two other 27mer sequences specific for the EGFP-S2 and EGFP-S3 sites. PKR activation in cell lysates was also assayed as described previously (Gunnery and Mathews, 1998). The lysate was treated with the indicated RNAs, followed by immunoprecipitation. The positive control long dsRNA elicited PKR activation, but none of the shorter RNAs activated PKR (FIG. 7C).

Example 13

Asymmetric 27Mer Duplex Design and Base Modifications can Influence Dicing Patterns and Allow Intelligent Design of 27Mer This examples demonstrates that multiple species are produced by Dicer action on the 27mer and that design of the 27mer and/or inclusion of base modifications can be employed to direct these degradation patterns, limit heterogeneity, and predict end products.

It was demonstrated in Example 6, FIGS. 3A and 3B that all of the individual 21mers that could be produced by Dicer action on the EGFPS1 27mer duplex are less potent in suppressing EGFP than the 27mer duplex. Nevertheless, which 21mers are produced can influence ultimate potency. An electrospray mass spectrometry assay was used to determine which 21mers are the actual products that result from enzymatic digestion of a 27mer substrate RNA by Dicer.

More than one 21mer can result from Dicer digestion of the 27mer. Dicing patterns can be controlled, permitting intelligent design.

Electrospray Mass Spectrometry Assay of In Vitro Dicing Reactions

RNA duplexes (100 pmoles) were incubated in 20 μl of 20 mM Tris pH 8.0, 200 mM NaCl, 2.5 mM $MgCl_2$ with 1 unit of recombinant human Dicer (Stratagene, La Jolla, Calif.) for 12-24 hours. Electrospray-ionization liquid chromatography mass spectroscopy (ESI-LCMS) of duplex RNAs pre- and post-treatment with Dicer were done using an Oligo HTCS system (Novatia, Princeton, N.J.), which consisted of ThermoFinnigan TSQ7000, Xcalibur data system, ProMass data processing software and Paradigm MS4™ HPLC (Michrom BioResources, Auburn, Calif.). The liquid chromatography step employed before injection into the mass spectrometer (LC-MS) removes most of the cations complexed with the nucleic acids; some sodium ion can remain bound to the RNA and are visualized as minor +22 or +44 species, which is the net mass gain seen with substitution of sodium for hydrogen. Accuracy of this assay is around +/−2 Daltons for oligonucleotides of this size.

Results

Figure 8A:
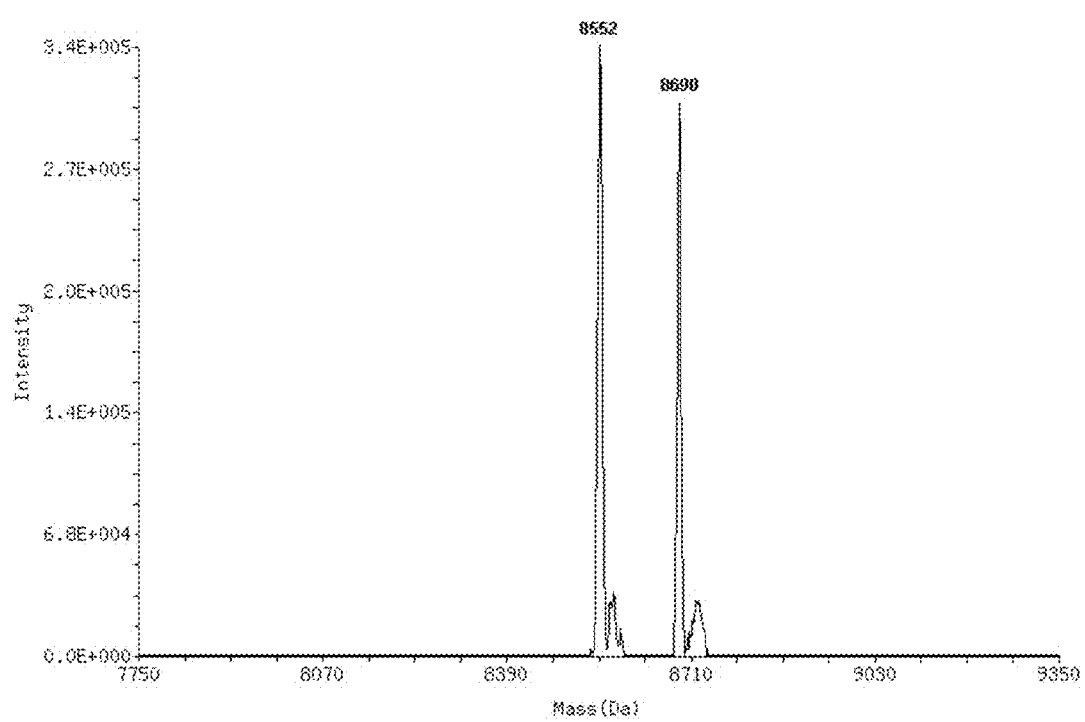
FIGS. 8A-8B show ESI mass spectra of the 27mer duplex EGFPS1 27+0 L before (FIG. 8A) and after (FIG. 8B) incubation with Dicer. Duplexes separate into single strands and the measured mass of each strand is indicated.
Figure 8B:
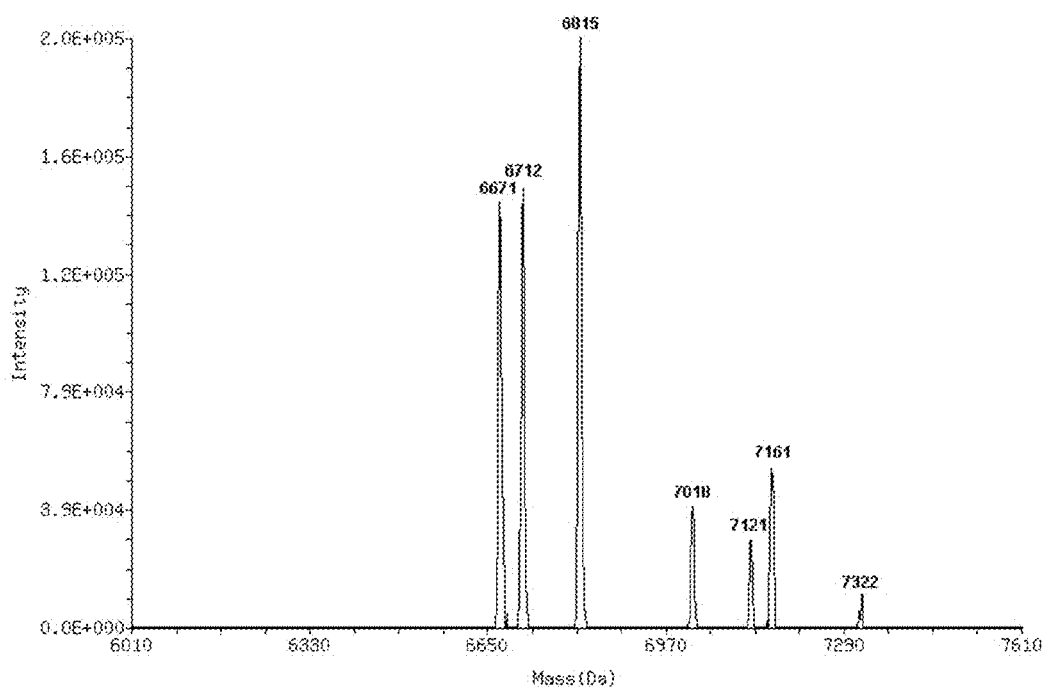

The EGFPS1-27+0 duplex was digested with Dicer and mass spectra were obtained pre-digestion (FIG. 8A) and post-digestion (FIG. 8B). In general, Dicer will cleave a 27mer duplex into 21mer length fragments with a 5'-phosphate. Lesser amounts of 22mers are also usually generated. Small amounts of 20mer and 23mers can also sometimes be observed. By comparing observed masses with the starting sequence, it can be deduced that 4 duplexes with 2-base 3'-overhangs and 5'-phosphate were produced in this dicing reaction. These species represent two major cleavage products, both of which resulted in 21mer and 22mer duplexes. Lower case "p" represents a phosphate group. Calculated masses for each possible digestion product that could result from in vitro Dicer cleavage are shown in Table 8.

TABLE 8

Molecular Weights of Possible
Duplexes Derived from the 27mer Duplex by Dicer Processing

| Sequence (SEQ ID NO:) | Name | Mol Wt |
|---|---|---|
| 5' AAGCUGACCCUGAAGUUCAUCUGCACC (41) | EGFPS1-27 + 0 L | 8552 |
| 3' UUCGACUGGGACUUCAAGUAGACGUGG (42) | | 8689 |
| 5' pACCCUGAAGUUCAUCUGCACC (11) | EGFPS1-21 + 2(3) | 6672 |
| 3' ACUGGGACUUCAAGUAGACGUp (12) | | 6816 |
| 5' pGACCCUGAAGUUCAUCUGCACC (98) | EGFPS1-22 + 2(3) | 7017 |
| 3' GACUGGGACUUCAAGUAGACGUp (99) | | 7161 |
| 5' pUGACCCUGAAGUUCAUCUGCA (15) | EGFPS1-21 + 2(5) | 6713 |
| 3' CGACUGGGACUUCAAGUAGACp (16) | | 6815 |
| 5' pCUGACCCUGAAGUUCAUCUGCA (100) | EGFPS1-22 + 2(5) | 7018 |
| 3' UCGACUGGGACUUCAAGUAGACp (101) | | 7121 |

Figure 1B:
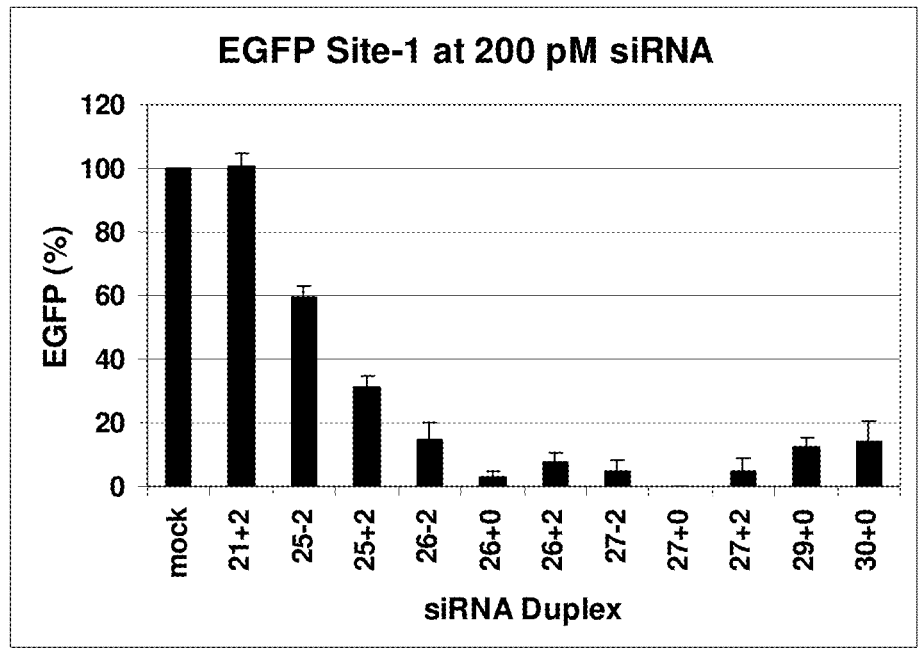
Figure 1C:
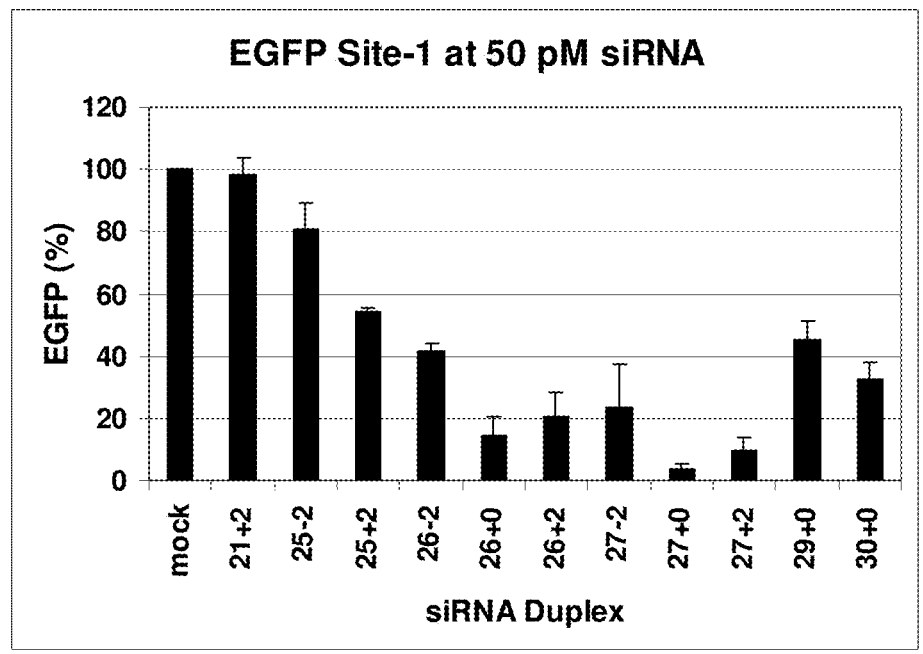
Figure 1D:
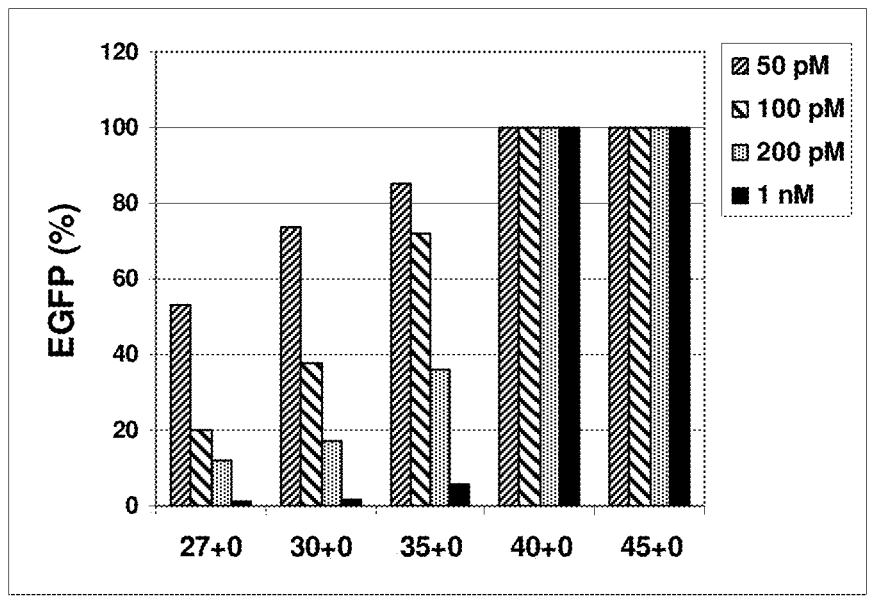
Figure 1E:
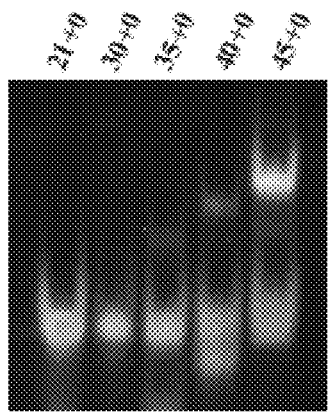
Figure 1F:
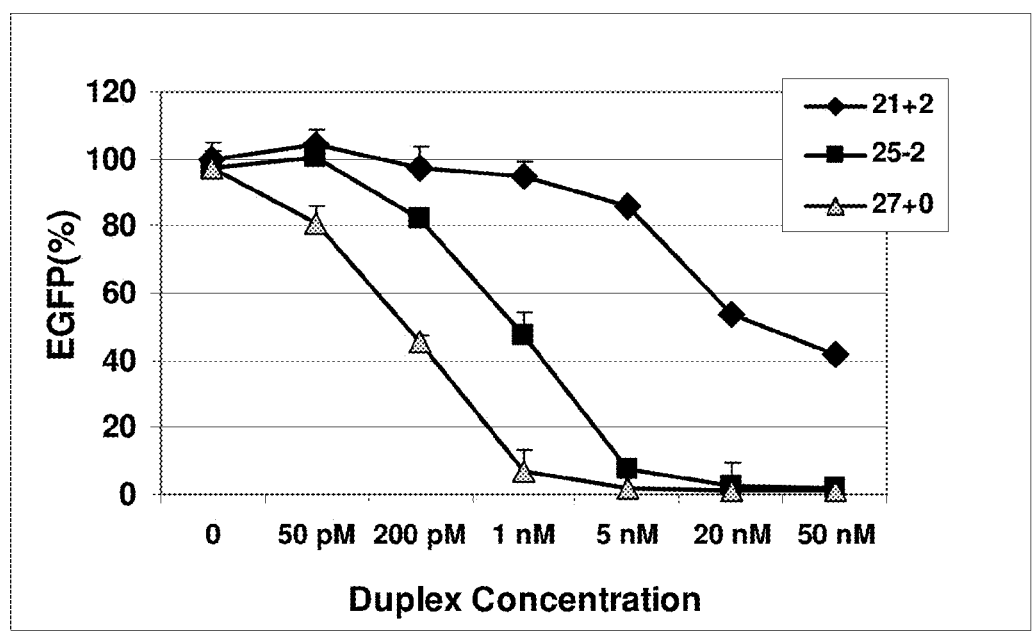

It was demonstrated in Example 2, FIGS. 1A-1C that blunt duplexes or duplexes with 5'-overhangs can show similar or better potency than duplexes with 3'-overhangs. In these studies, both ends of the duplex were symmetric (i.e., both ends were blunt, both ends were 3'-overhang, or both ends were 5'-overhang). In similar studies, it was found that a blunt 27mer duplex with two bases mismatch at one end had higher potency than the symmetric blunt, 3'-overhang, or 5'-overhang species tested. The blunt duplex with 2-base mismatch on one end might mimic the behavior of an asymmetric duplex with a 2-base 3'-overhang on one end and blunt on the other end. Asymmetric 27mer duplexes of this kind were tested and found to have increased potency and fewer diced products (less heterogeneity) and resulted in a more predictable pattern.

The double-stranded RNA binding domains of many enzymes often specifically recognize RNA and not DNA or some modified RNAs. Insertion of DNA residues into the ends of blunt 27mer duplexes was studied. Asymmetric designs with DNA residues in the 3'-end of one strand resulted in fewer diced products (less heterogeneity) and generally produced a predicable pattern which was opposite that of the asymmetric 3'-overhang designs.

The EGFPS1-27+0 duplex was modified to have an asymmetric 3'-overhang on one side and 2 DNA bases at the 3'-end of the other side. A 5-phosphate was placed on the recessed strand at the 3-overhang to mimic dicer processing. The final duplex of this design is show below aligned with the original blunt 27mer. Lower case "t" represents DNA dT base and lower case "p" represents a phosphate group. Calculated masses are shown in Table 9.

TABLE 9

Molecular Weights of Duplexes

| Sequence (SEQ ID NO:) | Name | Mol Wt |
|---|---|---|
| 5' AAGCUGACCCUGAAGUUCAUCUGCACC (41) | EGFPS1- 27 + 0 L | 8552 |
| 3' UUCGACUGGGACUUCAAGUAGACGUGG (42) | | 8689 |
| 5' AAGCUGACCCUGAAGUUCAUCUGCACC (41) | EGFPS1- 27/25 L | 8552 |
| 3' ttCGACUGGGACUUCAAGUAGACGUp (102) | | 8075 |

Figure 8C:
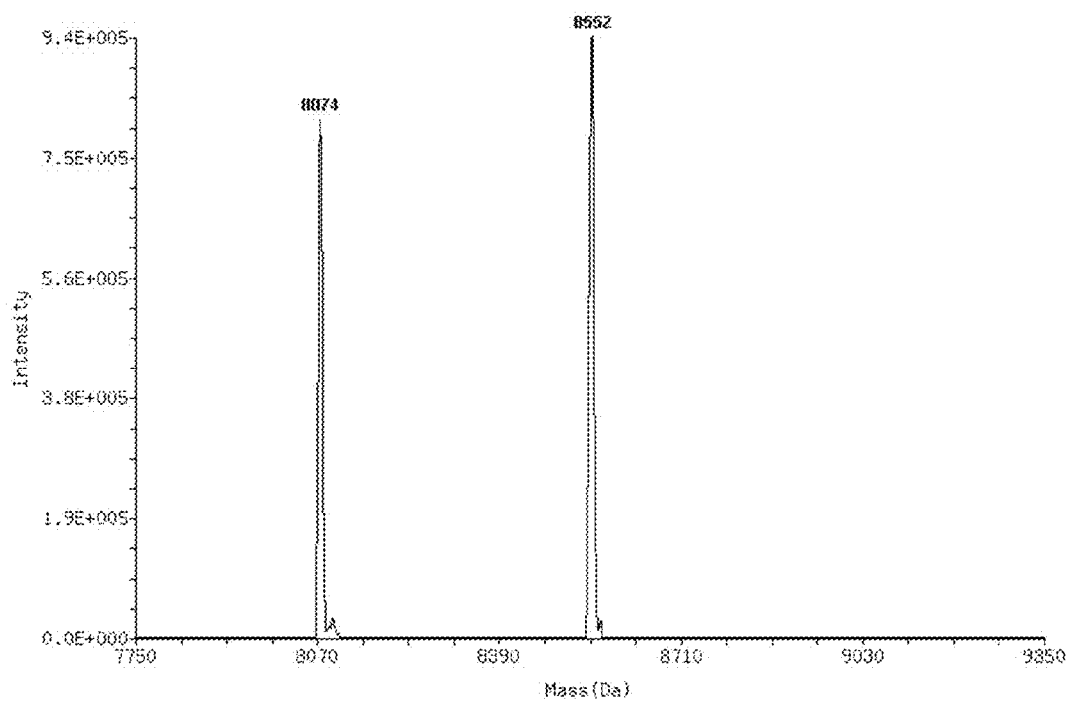
FIGS. 8C-8D show ESI mass spectra of the 27mer duplex EGFPS1 27/25 L before (FIG. 8C) and after (FIG. 8D) incubation with Dicer. Duplexes separate into single strands and the measured mass of each strand is indicated.
Figure 8D:
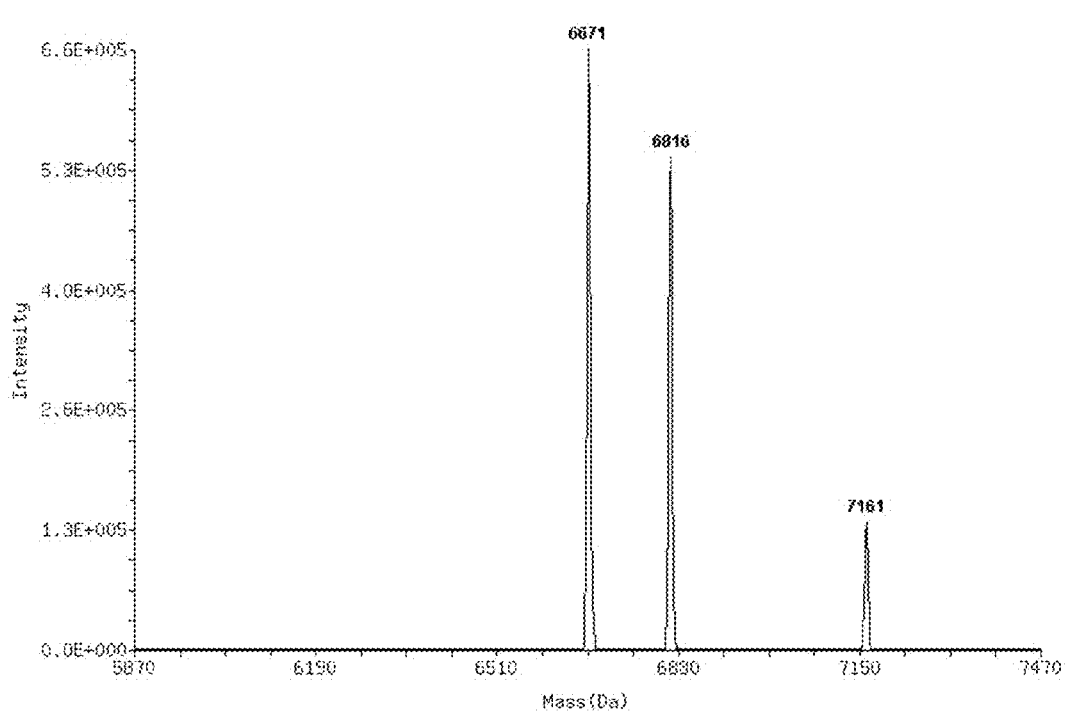

Mass spectra were obtained pre-digestion (FIG. 8C) and post-digestion (FIG. 8D). Analysis of the dicing products made from the modified asymmetric duplex was much simpler than for the symmetric duplex (compare FIGS. 8B with 8D). A single cleavage product was observed which was mostly 21mer duplex with small amounts of 22mer detectable. Lower case "t" represents DNA dT base and lower case "p" represents a phosphate group. Calculated masses are shown in Table 10.

TABLE 10

Molecular Weights of Possible Duplexes Derived from the 27mer/25mer Duplex by Dicer Processing

| Sequence (SEQ ID NO:) | Name | Mol Wt |
|---|---|---|
| 5' AAGCUGACCCUGAAGUUCAUCUGCACC (41) | EGFPS1-27/25 L | 8552 |
| 3' ttCGACUGGGACUUCAAGUAGACGUp (102) | | 8075 |
| 5' pACCCUGAAGUUCAUCUGCACC (11) | EGFPS1-21 + 2(3) | 6672 |
| 3' ACUGGGACUUCAAGUAGACGUp (12) | | 6816 |
| 3' GACUGGGACUUCAAGUAGACGUp (99) | | 7161 |

Use of asymmetric design with a single 2-base 3'-overhang and selective incorporation of DNA residues simplifies the dicing reaction to yield a single major cleavage product. This design additionally permits prediction of the dicing pattern and allows for intelligent design of 27mers such that specific, desired 21mers can be produced from dicing. As demonstration, a second 27mer duplex, EGFPS1-27-R was studied which overlaps the EGFPS1-27-L sequence. Calculated masses are shown in Table 11.

The EGFPS1-27+0-R duplex was converted to a DNA-modified, asymmetric 25/27mer duplex as shown below and this duplex was studied in the in vitro dicing assay. Lower case "cg" represents DNA dCdG base and lower case "p" represents a phosphate group. Calculated masses are shown in Table 13.

TABLE 11

Molecular Weights of Duplexes

| Sequence (SEQ ID NO:) | Name | Mol Wt |
|---|---|---|
| 5' AAGCUGACCCUGAAGUUCAUCUGCACC (41) | EGFPS1-27 + 0 L | 8552 |
| 3' UUCGACUGGGACUUCAAGUAGACGUGG (42) | | 8689 |
| 5' UGACCCUGAAGUUCAUCUGCACCACCG (103) | EGFPS1-27 + 0 R | 8528 |
| 3' ACUGGGACUUCAAGUAGACGUGGUGGC (104) | | 8728 |

Figure 9A:
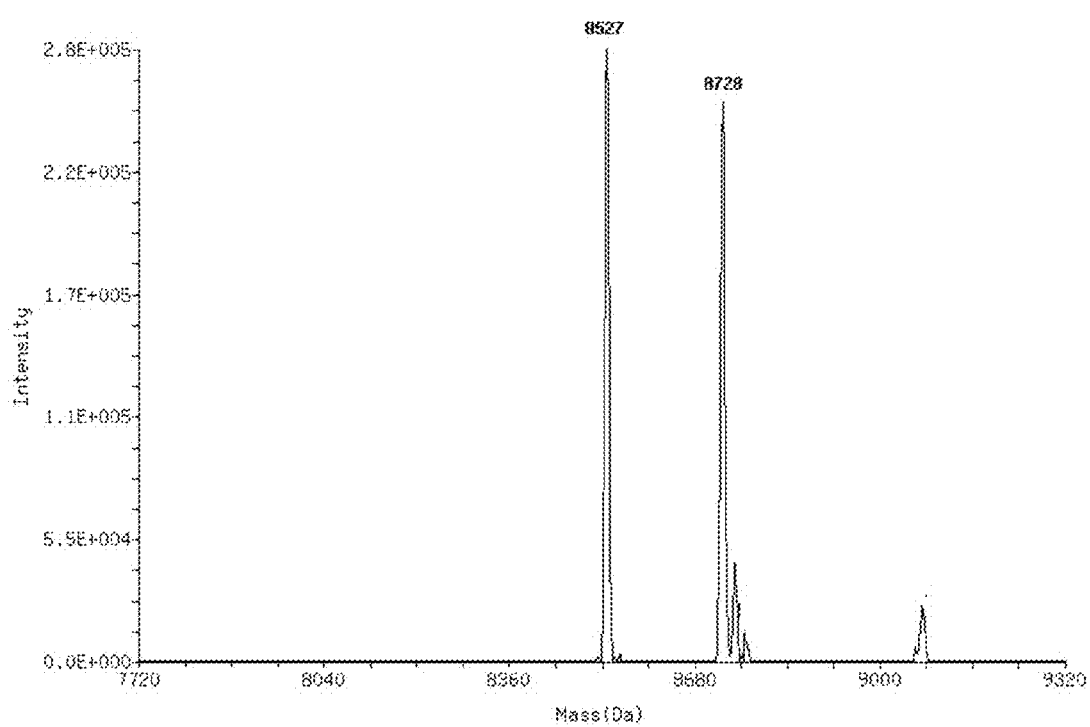
FIGS. 9A-9B show ESI mass spectra of the 27mer duplex EGFPS1 27+0 R before (FIG. 9A) and after (FIG. 9B) incubation with Dicer. Duplexes separate into single strands and the measured mass of each strand is indicated.
Figure 9B:
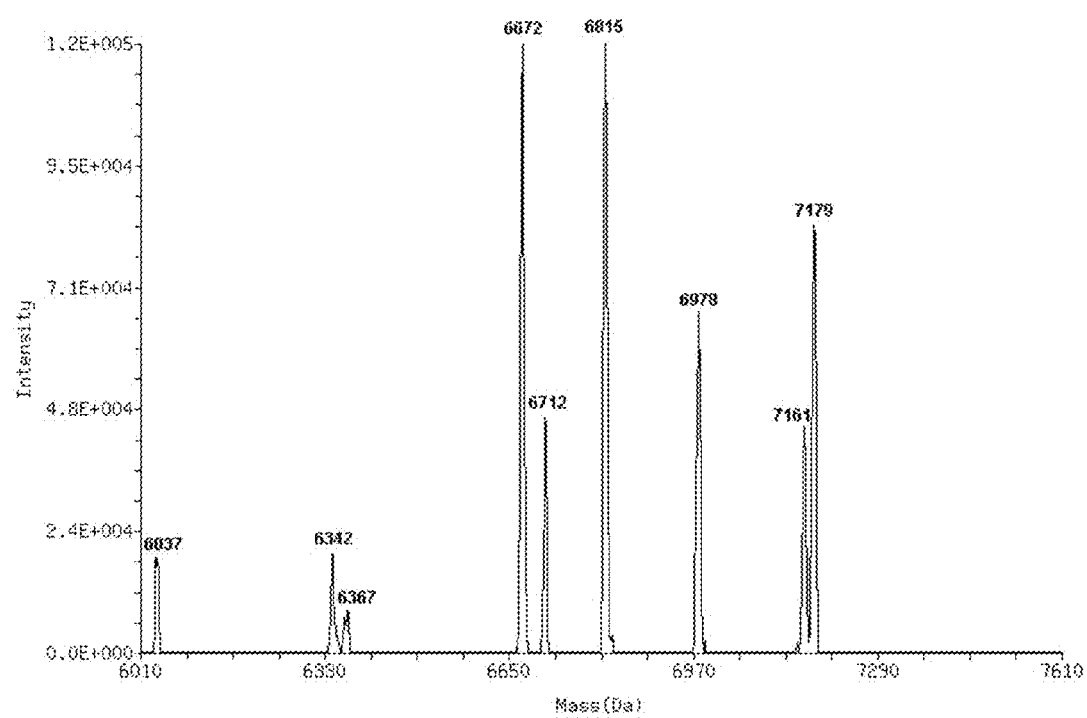

Mass spectra were obtained pre-digestion (FIG. 9A) and post-digestion (FIG. 9B). Analysis of the dicing products made from the EGFPS1-27+0 R duplex showed a complex pattern similar to that seen with the EGFPS1-27+0 L duplex. Two major cleavage products were observed and both 21mer and 22mer species were present. Very minor 20mer species were also seen. Lower case "p" represents a phosphate group. Calculated masses for each possible digestion product that could result from in vitro Dicer cleavage are shown in Table 12.

TABLE 12

Molecular Weights of Possible Duplexes Derived from the 27mer Duplex by Dicer Processing

| Sequence (SEQ ID NO:) | Name | Mol Wt |
|---|---|---|
| 5' UGACCCUGAAGUUCAUCUGCACCACCG (103) | EGFPS1-27 + 0 R | 8528 |
| 3' ACUGGGACUUCAAGUAGACGUGGUGGC (104) | | 8728 |
| 5' pUGAAGUUCAUCUGCACCACCG (105) | EGFPS1-21(1) R | 6712 |
| 5' pCCUGAAGUUCAUCUGCACCACC (106) | EGFPS1-22(3)R | 6977 |
| 3' UGGGACUUCAAGUAGACGUGGUp (107) | | 7178 |
| 5' pACCCUGAAGUUCAUCUGCACCACC (108) | EGFPS1-27 + 0 R | 6672 |
| 3' ACUGGGACUUCAAGUAGACGUGGUp (109) | | 6816 |
| 3' ACUGGGACUUCAAGUAGACGUGp (110) | EGFPS1-22(5)R | 7161 |

TABLE 13

Molecular Weights of Duplexes

| Sequence (SEQ ID NO:) | Name | Mol Wt |
|---|---|---|
| 5' UGACCCUGAAGUUCAUCUGCACCACCG (103) | EGFPS1-27 + 0 R | 8528 |
| 3' ACUGGGACUUCAAGUAGACGUGGUGGC (104) | | 8728 |
| 5' pACCCUGAAGUUCAUCUGCACCACcg (111) | EGFPS1-25/27 R | 7925 |
| 3' ACUGGGACUUCAAGUAGACGUGGUGGC (112) | | 8728 |

Figure 9C:
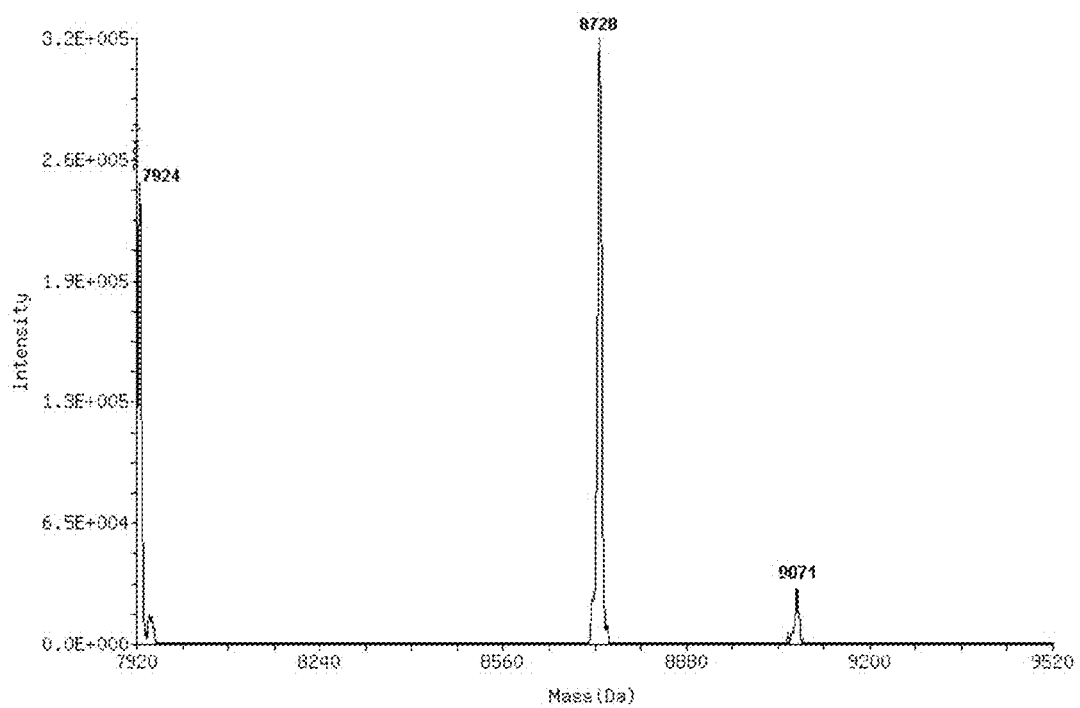
FIGS. 9C-9D show ESI mass spectra of the 27mer duplex EGFPS1 25/27 R before (FIG. 9C) and after (FIG. 9B) incubation with Dicer. Duplexes separate into single strands and the measured mass of each strand is indicated.
Figure 9D:
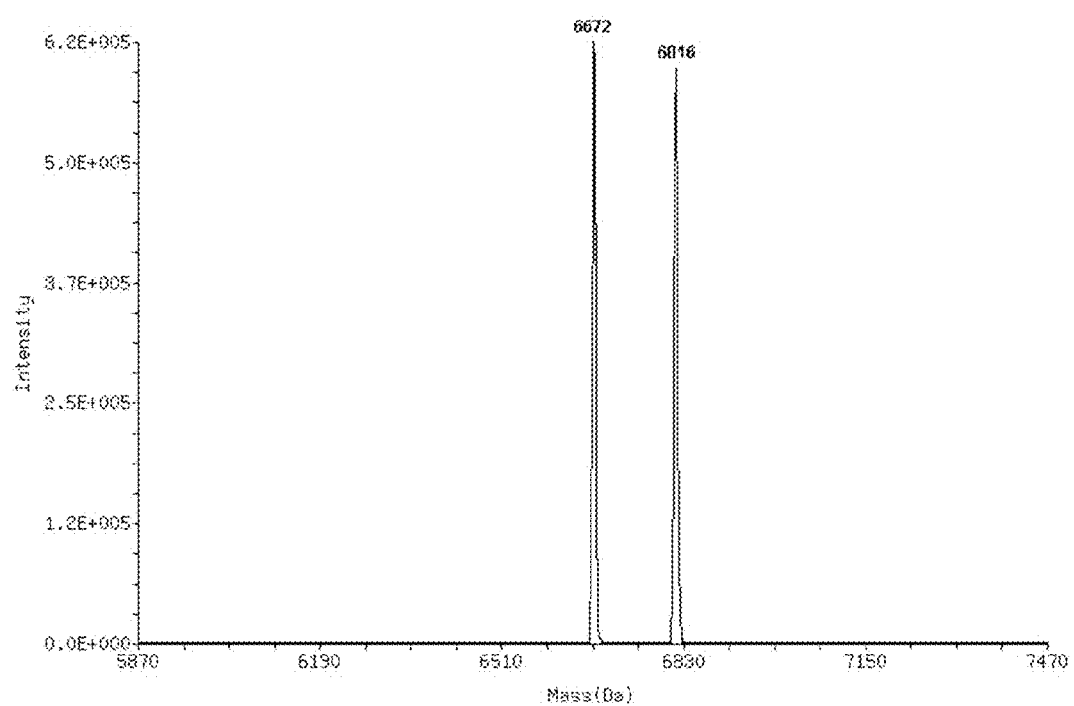

Mass spectra were obtained pre-digestion (FIG. 9C) and post-digestion (FIG. 9D). The DNA-modified asymmetric EGFPS1-25/25 R duplex showed a clean, single diced 21mer species, as summarized in Table 14. Lower case "p" represents a phosphate group.

TABLE 14

Molecular Weight of Possible Duplex Derived from the 25 mer/27mer Duplex by Dicer Processing

| Sequence (SEQ ID NO:) | Name | Mol Wt |
|---|---|---|
| 5' pACCCUGAAGUUCAUCUGCACCACcg (111) | EGFPS1-25/27 R | 7925 |
| 3' ACUGGGACUUCAAGUAGACGUGGUGGC (112) | | 8728 |
| 5' pACCCUGAAGUUCAUCUGCACC (11) | EGFPS1-21 + 2(3) | 6672 |
| 3' ACUGGGACUUCAAGUAGACGUp (12) | | 6816 |

If the results of FIGS. 8D and 9D are compared, it can be seen that digestion of the two different asymmetric duplexes EGFPS1-27/25 L and EGFPS1-25/27R result in formation of the same 21mer species, EGFPS1-21(3). Lower case "t" or "cg" represents DNA bases and lower case "p" represents a phosphate group. Calculated masses are shown in Table 15.

TABLE 15

Molecular Weights of Duplexes

| Sequence (SEQ ID NO:) | Name | Mol Wt |
|---|---|---|
| 5' AAGCUGACCCUGAAGUUCAUCUGCACC (41) | EGFPS1-27/25 L | 8552 |
| 3' ttCGACUGGGACUUCAAGUAGACGUp (102) | | 8075 |
| 5' pACCCUGAAGUUCAUCUGCACCACcg (111) | EGFPS1-25/27 R | 7925 |
| 3' ACUGGGACUUCAAGUAGACGUGGUGGC (112) | | 8728 |
| 5' pACCCUGAAGUUCAUCUGCACC (11) | EGFPS1-21 + 2(3) | 6672 |
| 3' ACUGGGACUUCAAGUAGACGUp (12) | | 6816 |

Therefore use of the DNA-modified asymmetric duplex design as taught by the invention reduces complexity of the dicing reaction for 27mer RNA species and permits intelligent design of 27mers for use in RNAi such that it is possible to specifically target a desired location. Cleavage of the substrate 27mer by Dicer results in a unique, predictable 21mer wherein one end of the 21mer coincides with the 3'-overhang end of the substrate 27mer.

Example 14

Asymmetric 27Mer Duplex Designs with Base Modifications can Improve Potency Over Blunt 27Mers This examples demonstrates that the new asymmetric RNA duplexes as taught by the invention, having a 2-base 3'-overhang on one side and blunt with 3-base 3'-DNA modification on the other side, can improve potency over blunt 27mer duplexes.

It was demonstrated in Example 13, FIGS. 8A-8D and 9A-9D, that use of asymmetric duplexes can direct dicing and result in a single major 21mer cleavage product. Further, the 27/25 L and 25/27 R asymmetric duplexes both result in the same 21mer duplex after dicing. Since the same 21mer duplex is produced from each of the two asymmetric 27mers, it would be anticipated by one skilled in the art that these compounds should functionally have similar potency. It is shown in this example that this is not the case and that the 25/27 R design unexpectedly has increased potency relative to both the 27/25 L duplex and the blunt 27+0 duplex.

RNA duplexes targeting EGFPS2 were co-transfected into HEK293 cells with an EGFP expression plasmid and assayed for EGFP activity after 24 hours incubation according to methods described above. Transfected duplexes are shown in Table 16. Lower case "p" represents a phosphate group and lower case bases "cc" and "gt" represent DNA bases while uppercase bases represent RNA.

Figure 10A:
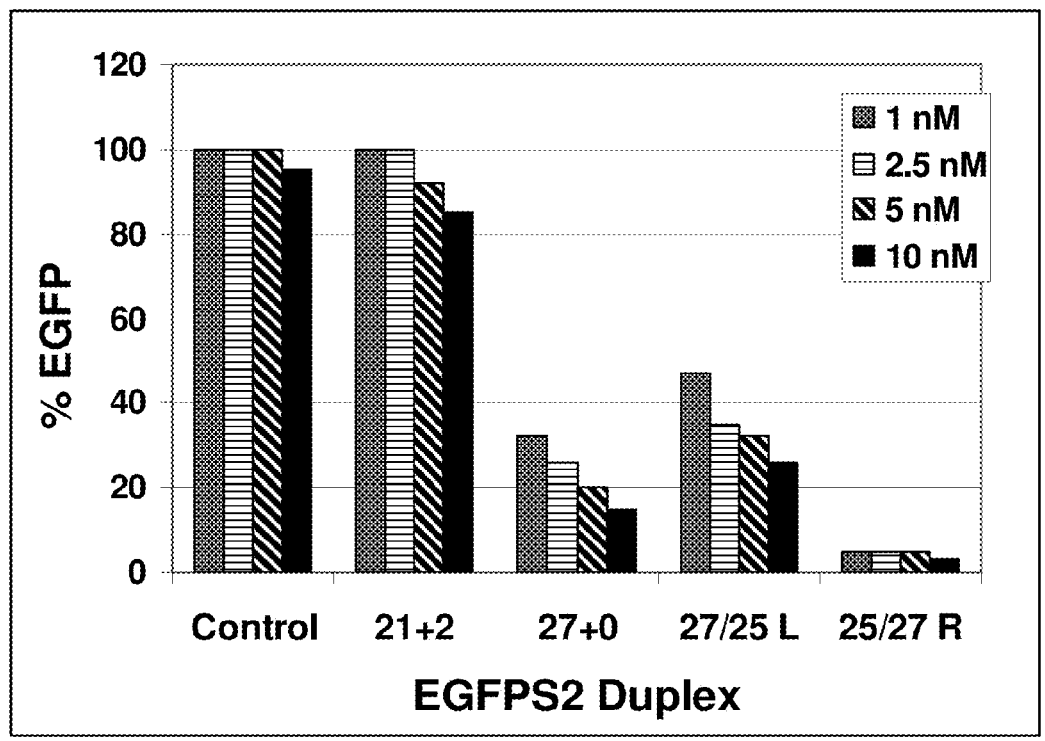
FIGS. 10A-10B show that duplexes designed to enhance Dicer processing are potent effectors of RNAi. EGFP expression levels were determined after cotransfection of HEK293 cells with a fixed amount of EGFP expression plasmid and varying concentrations of dsRNAs.
Figure 10B:
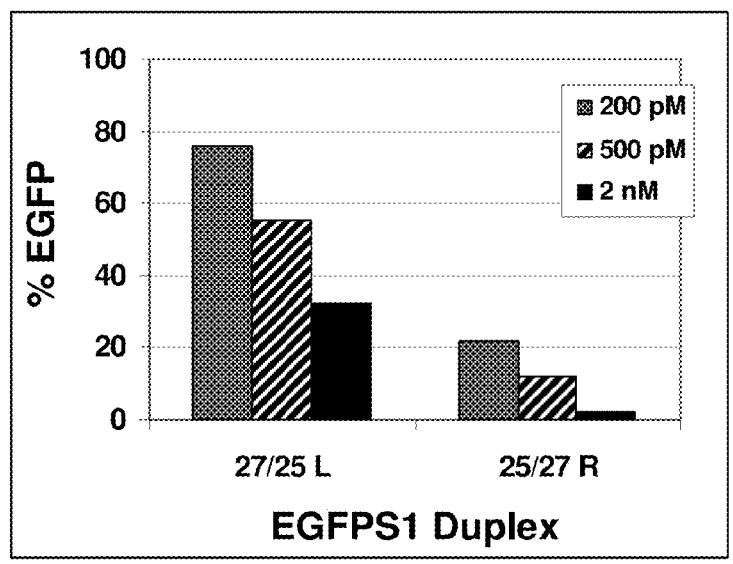

EGFP expression after transfection is shown in FIG. 10B. As before, the 25/27 R duplex was significantly more potent than the 27/25 L duplex in reducing EGFP expression. In a similar experiment in which the blunt ended 27mer was compared with 25/27 R duplex and 27/25 L duplex, it was found that the dsRNAs had the following potencies:

25/27 R duplex>27/25 L duplex>27mer.

27mer duplex RNAs can show significantly higher potency than 21mer duplexes in suppressing targeted gene expression. The blunt 27mers can result in a variety of 21mer species after dicing, so precise performance of a blunt 27mer duplex cannot always be predicted. The novel asym-

TABLE 16

Transfected Duplexes

| Sequence | Name | SEQ ID NO: |
|---|---|---|
| 5' GCAGCACGACUUCUUCAAGUU<br>3' UUCGUCGUGCUGAAGAAGUUC | EGFPS2-21 + 2 | SEQ ID NO: 76<br>SEQ ID NO: 77 |
| 5' AAGCAGCACGACUUCUUCAAGUCCGCC<br>3' UUCGUCGUGCUGAAGAAGUUCAGGCGG | EGFPS2-27 + 0 | SEQ ID NO: 78<br>SEQ ID NO: 79 |
| 5' CAUGAAGCAGCACGACUUCUUCAAGUC<br>3' gtACUUCGUCGUGCUGAAGAAGUUCp | EGFPS2-27/25 L | SEQ ID NO: 113<br>SEQ ID NO: 114 |
| 5' pGCAGCACGACUUCUUCAAGUCCGcc<br>3' UUCGUCGUGCUGAAGAAGUUCAGGCGG | EGFPS2-25/27 R | SEQ ID NO: 115<br>SEQ ID NO: 79 |

The EGFPS2-21+2 and EGFPS2-27+0 RNA duplexes were employed previously in Example 9. The EGFPS2-27/25 L and EGFPS2-25/27 R duplexes are new asymmetric dsRNAs designed according to the present invention and target the same site, site II of EGFP. In the in vitro dicing electrospray mass spectrometry assay as described in Example 13, both the EGFPS2-27/25 L and EGFPS2-25/27 R duplexes yield the same 21mer product after digestion by Dicer, similar to the EGFPS2-21+2 duplex.

Transfection results are shown in FIG. 10A. As previously shown, the EGFPS2-21+2 duplexes had minimal activity in suppressing EGFP expression while the 27+0 duplex showed significant inhibition. The 27/25 L duplex was slightly less potent than the 27+0 duplex and the 25/27 R duplex was most potent. Based upon the teaching of prior art, this finding is unexpected, since both of the asymmetric duplexes produce the same 21mer species following dicing.

Similar transfections were done using the EGFPS1 duplexes 27/25 L and 25/27 R. These duplexes produce the same 21mer product, the EGFPS1-21(3) duplex, after dicing (Example 13). Transfected duplexes are shown in Table 17. Lower case "p" represents a phosphate group and lower case bases "tt" represent DNA bases while uppercase bases represent RNA.

metric duplexes of the present invention wherein one side of the duplex has a 2-base 3'-overhang and the other side is blunt and has base modifications, such as DNA, at the 3'-end, force dicing to occur in a predictable way so that precise 21mers result. These asymmetric duplexes, i.e., 27/25 L and 25/27 R, are each also more potent than the 21mers. The asymmetric 25/27 R design is the most potent embodiment of the present invention.

FIG. 11 is an illustration comparing the embodiments of the present invention. The target gene sequence is illustrated by SEQ ID NO:116. The "typical" parent 21mer used as an siRNA molecule is shown aligned with the target gene sequence. Aligned with the target gene and parent 21mer sequences is the L 27mer v2.1 containing a 3' overhang on the sense strand and two DNA bases at the 3' end of the antisense strand. The diced cleavage product is also shown. This alignment illustrates the left shift in designing these precursor RNAi molecules. Also aligned with the target gene and parent 21mer sequences is the R 27mer v2.1 containing a 3' overhang on the antisense strand and two DNA bases at the 3' end of the sense strand. The diced cleavage product is also shown. This alignment illustrates the right shift in designing these precursor RNAi molecules.

TABLE 17

Transfected Duplexes

| Sequence | Name | SEQ ID NO: |
|---|---|---|
| 5' AAGCUGACCCUGAAGUUCAUCUGCACC<br>3' ttCGACUGGGACUUCAAGUAGACGUp | EGFPS1-27/25 L | SEQ ID NO: 41<br>SEQ ID NO: 102 |
| 5' pACCCUGAAGUUCAUCUGCACCACcg<br>3' ACUGGGACUUCAAGUAGACGUGGUGGC | EGFPS1-25/27 R | SEQ ID NO: 111<br>SEQ ID NO: 112 |

Example 15

Determination of Effective Dose

This example demonstrates a method for determining an effective dose of the dsRNA of the invention in a mammal. A therapeutically effective amount of a composition containing a sequence that encodes a dsRNA, (i.e., an effective dosage), is an amount that inhibits expression of the product of the target gene by at least 10 percent. Higher percentages of inhibition, e.g., 20, 50, 90 95, 99 percent or higher may be desirable in certain circumstances. Exemplary doses include milligram or microgram amounts of the molecule per kilogram of subject or sample weight (e.g., about 1 microgram per kilogram to about 5 milligrams per kilogram, about 100 micrograms per kilogram to about 0.5 milligrams per kilogram, or about 1 microgram per kilogram to about 50 micrograms per kilogram). The compositions can be administered one or more times per week for between about 1 to 10 weeks, e.g., between 2 to 8 weeks, or between about 3 to 7 weeks, or for about 4, 5, or 6 weeks, as deemed necessary by the attending physician. Treatment of a subject with a therapeutically effective amount of a composition can include a single treatment or a series of treatments.

Appropriate doses of a particular dsRNA composition depend upon the potency of the molecule with respect to the expression or activity to be modulated. One or more of these molecules can be administered to an animal, particularly a mammal, and especially humans, to modulate expression or activity of one or more target genes. A physician may, for example, prescribe a relatively low dose at first, subsequently increasing the dose until an appropriate response is obtained. In addition, it is understood that the specific dose level for any particular subject will depend upon a variety of other factors including the severity of the disease, previous treatment regimen, other diseases present, off-target effects of the active agent, age, body weight, general health, gender, and diet of the patient, the time of administration, the route of administration, the rate of excretion, any drug combination, and the degree of expression or activity to be modulated.

The efficacy of treatment can be monitored by measuring the amount of the target gene mRNA (e.g. using real time PCR) or the amount of product encoded by the target gene such as by Western blot analysis. In addition, the attending physician can monitor the symptoms associated with the disease or disorder afflicting the patient and compare with those symptoms recorded prior to the initiation of treatment.

It is clear from recent studies that the effects of RNAi are not entirely specific and that undesired 'off-target' effects can occur of a magnitude dependent on the concentration of siRNA (Persengiev et al., 2004). The new Dicer substrate dsRNA approach may facilitate use of lower concentrations of duplex RNA than are needed with traditional 21mer siRNAs. It is clear from published data that 'off-target' effects can occur in certain cell lines using 21mer siRNAs (Persengiev et al., 2004; Jackson et al., 2003), but these also can be minimized by using reagents that have efficacy in the low to subnanomolar range (Persengiev et al., 2004). To examine the potential for 'off-target' effects using Dicer substrate dsRNAs, we carried out microarray analyses comparing an siRNA 21mer with the 27mer, each targeting EGFP site 1. NIH3T3 cells that stably express EGFP were transfected with concentrations of siRNA that give effective target knockdowns (FIG. 2A, FIG. 7D). Total cellular RNAs were prepared from cells 24 and 48 h after transfection and analyzed by hybridization to an oligonucleotide microarray as described in FIG. 7D. Among the 16,282 mouse genes analyzed, only a small fraction showed upregulation or downregulation more than twofold above or below control values (FIG. 7D). The 27mer and 21mer gave comparable results at their effective RNAi concentrations. There was an increase in the number of transcripts upregulated when the 27mer was used at the higher 25 nM concentration, but comparisons of the targets affected at 24 versus 48 h and at 5 nM versus 25 nM showed no overlap. Rather than specific 'off-target' effects, these changes are more consistent with statistical scatter among the 16,282 genes examined. The same assay was repeated using the EGFP-S2 27+0 duplex RNA with comparable results.

Given the increase in potency of the 27mer dsRNAs relative to 21+2 siRNAs, it is of interest that this observation has not been previously reported. Although others have used dsRNAs of up to 27 bp for RNAi studies in mammalian cells (Bohula et al., 2003; Caplen et al., 2001), no differences in efficacy were reported as compared with traditional 21+2 duplexes. This discrepancy between previous studies and our own may simply be due to differences in the concentration of dsRNAs tested. "Good" sites for 21mer siRNAs can have potencies in the nanomolar range (Reynolds et al., 2004). When 'good' sites are tested at high concentrations of transfected RNA, differences between 21mer siRNAs and 27mer dsRNAs will most likely be small and easily overlooked. Marked differences in potency are best shown by testing at low nanomolar or picomolar concentrations, something that is not routinely done in most laboratories.

Thus far, the 27mer dsRNA design has shown increased RNAi potency relative to 21+2 siRNAs at every site examined. Within the set of 27mers studied here, however, a range of potencies is nevertheless seen between different target sites within the same gene (FIG. 3B). We have shown that, even in the absence of fully optimized design rules, use of Dicer substrate dsRNA approach can increase RNAi potency relative to traditional 21+2 siRNAs. Additionally, the use of 27mer dsRNAs allows targeting of some sites within a given sequence that are refractory to suppression with traditional 21mer siRNAs. Use of Dicer substrate dsRNAs to trigger RNAi should result in enhanced efficacy and longer duration of RNAi at lower concentrations of RNA than are required for 21+2 applications. Consistent with our results linking Dicer cleavage to enhanced RNAi efficacy, it has recently been shown that chemically synthesized hairpin RNAs that are substrates for Dicer are more potent inducers of RNAi than conventional siRNAs and, moreover, that a two-base 3' overhang directs Dicer cleavage (Siolas et al., 2005).

Example 16

Survey of Modification Patterns

A site known to be potent for RNAi mediated suppression of the STAT1 gene was chosen to survey a wide variety of modification patterns in both 21mer siRNAs and 27mer DsiRNAs to test for relative potency and any toxic effects in tissue culture.

The 19-21mer RNAs that were tested are listed in Table 18.

TABLE 18

19-21mer Duplexes with Various Modification Patterns

Figure 12:
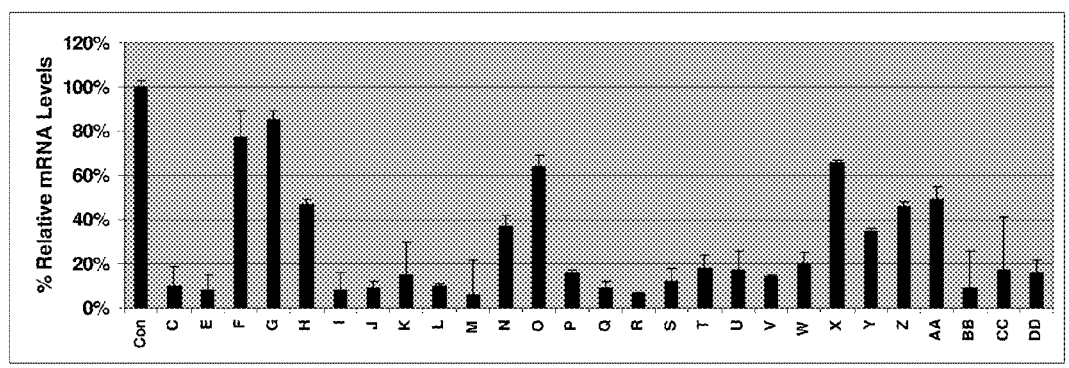
FIG. 12 shows the effect that various modifications incorporated into a 21mer duplex can have to the potency of that duplex as a trigger of RNAi. The figure lists the % mRNA levels relative to an unmodified control duplex as assessed by qRT-PCR 24 hours after transfection into HeLa cells a 1 nM concentration.

| Sequence | (SEQ ID NO:) | FIG. 12 Name |
|---|---|---|
| 5' pGCACCAGAGCCAAUGGAACUU<br>3' UUCGUGGUCUCGGUUACCUUGp | 117<br>118 | C |
| 5' pGCACCAGAGCCAAUGGAAC<br>3' CGUGGUCUCGGUUACCUUGp | 119<br>120 | E |
| 5' pGCACCAGAGCCAAUGGAAC<br>3' CGUGGUCUCGGUUACCUUGp | 121<br>122 | F |
| 5' pGCACCAGAGCCAAUGGAAC<br>3' CGUGGUCUCGGUUACCUUGp | 123<br>124 | G |
| 5' pGCACCAGAGCCAAUGGAAC<br>3' CGUGGUCUCGGUUACCUUGp | 125<br>126 | H |
| 5' pGCACCAGAGCCAAUGGAAC<br>3' UUCGUGGUCUCGGUUACCUUGp | 127<br>128 | I |
| 5' pGCACCAGAGCCAAUGGAAC<br>3' CGUGGUCUCGGUUACCUUGp | 129<br>130 | J |
| 5' pGCACCAGAGCCAAUGGAAC<br>3' CGUGGUCUCGGUUACCUUGp | 131<br>132 | K |
| 5' pGCACCAGAGCCAAUGGAAC<br>3' CGUGGUCUCGGUUACCUUGp | 133<br>134 | L |
| 5' pGCACCAGAGCCAAUGGAAC<br>3' UUCGUGGUCUCGGUUACCUUGp | 135<br>136 | M |
| 5' pGCACCAGAGCCAAUGGAAC<br>3' CGUGGUCUCGGUUACCUUGp | 137<br>138 | N |
| 5' pGCACCAGAGCCAAUGGAAC<br>3' CGUGGUCUCGGUUACCUUGp | 139<br>140 | O |
| 5' pGCACCAGAGCCAAUGGAACUU<br>3' UUCGUGGUCUCGGUUACCUUGp | 141<br>142 | P |
| 5' pGCACCAGAGCCAAUGGAACUU<br>3' UUCGUGGUCUCGGUUACCUUGp | 143<br>144 | Q |
| 5' pGCACCAGAGCCAAUGGAACUU<br>3' UUCGUGGUCUCGGUUACCUUGp | 145<br>146 | R |
| 5' pGcAccAGAGccAAuGGAAcuU<br>3' UucGuGGucucGGuuAccuuGp | 147<br>148 | S |
| 5' pGcAccAGAGccAAuGGAAcuU<br>3' UUCGUGGUCUCGGUUACCUUGp | 149<br>150 | T |
| 5' pGcAccAGAGccAAuGGAAcuU<br>3' UUCGUGGUCUCGGUUACCUUGp | 151<br>152 | U |
| 5' pGCACCAGAGCCAAUGGAACUU<br>3' UucGuGucucGGuuAccuuGp | 153<br>154 | V |
| 5' pGCACCAGAGCCAAUGGAACUU<br>3' UucGuGGucucGGuuAccuuGp | 155<br>156 | W |
| 5' pGcAccAGAGccAAuGGAAcuU<br>3' UucGuGGucucGGuuAccuuGp | 157<br>158 | X |
| 5' pGcAccAGAGccAAuGGAAcuU<br>3' UUCGUGGUCUCGGUUACCUUGp | 159<br>160 | Y |
| 5' pGcAccAGAGccAAuGGAAcuU<br>3' UUCGUGGUCUCGGUUACCUUGp | 161<br>162 | Z |
| 5' pGcAccAGAGccAAuGGAAcuU<br>3' UucGuGGucucGGuuAccuuGp | 163<br>164 | AA |

TABLE 18-continued 19-21mer Duplexes with Various Modification Patterns

| Sequence | (SEQ ID NO:) | FIG. 12 Name |
|---|---|---|
| 5' pGCACCAGAGCCAAUGGAACUU<br>3' UucGuGGucucGGuuAccuuGp | 165<br>166 | BB |
| 5' pGCACCAGAGCCAAUGGAACUU<br>3' UucGuGGucucGGuuAccuuGp | 167<br>168 | CC |
| 5' pGcAccAGAGccAAuGGAAcuU<br>3' UucGuGGucucGGuuAccuuGp | 169<br>170 | DD |

RNA = AGCU   2'OMe RNA = AGCU   2'F = <u>cu</u>   p = 5'-phos

The RNA duplexes were transfected into HeLa cells in 24 well plate format using Oligofectamine RNAs were transfected at 10 nM and 1 nM concentrations in triplicate. At 24 hours post transfection, RNA was prepared from cultures and cDNA was made; qRT-PCR assays were performed in triplicate and data were normalized to RPLP0 (acidic ribosomal protein P0) mRNA levels, using a negative control siRNA as 100%. The results are listed in FIG. 12.

Some modification patterns worked well while others did not. In particular, there was a concordance with the results and the findings of Czauderna et al. (NAR 31:2703 2003) relating to alternating 2'-O-Me RNA patterns. For this sequence/site, the fully modified duplex was inactive, or at least had a very significant loss of potency. Transfections done at 10 nM did not show appreciable improvement in potency for the highly modified species. None of the species showed obvious toxicity in cell culture within the 24 hours window studied.

Figure 13:
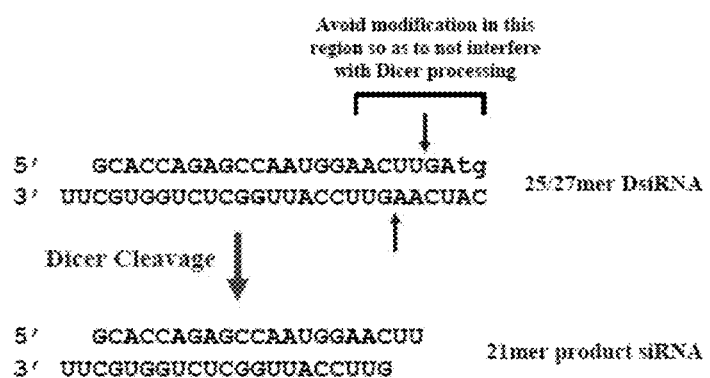
FIG. 13 shows the precise site of cleavage within a 25/27mer dsRNA substrate where Dicer processing is expected to occur. The Figure shows that modifications to the right of the expected cleavage site will not be present in the final product after cleavage.

The modification survey was next extended to the asymmetric 25/27mer DsiRNA duplex designs. Modified oligonucleotides were synthesized and annealed to make DsiRNA duplexes. The "dicing domain" was not modified so as to not block the ability of the endonuclease Dicer to cleave the substrate into the desired 21mer final product as outlined in the schematic shown in FIG. 13. The modified 25-27mer RNAs are listed in Table 19.

TABLE 19

25-27mer Duplexes with Various Modification Patterns

Figure 14:
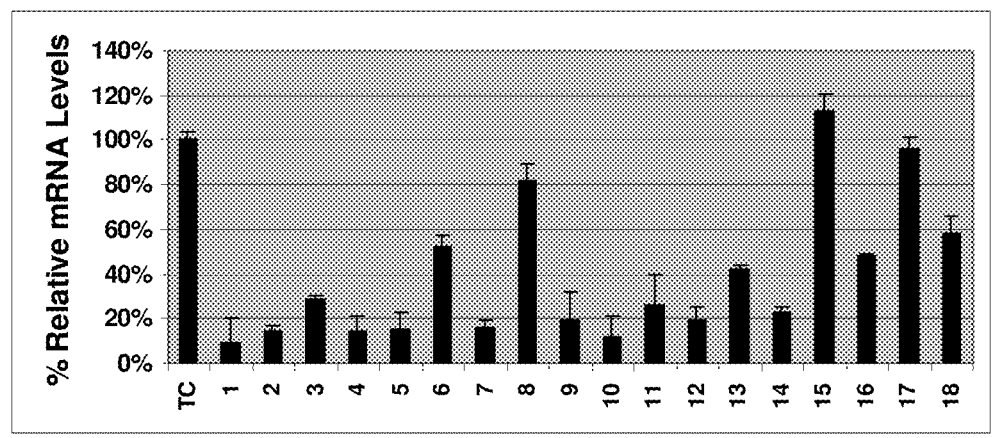
FIG. 14 shows the effect that various modifications incorporated into a 25/27mer DsiRNA duplex can have to the potency of that duplex as a trigger of RNAi. The figure lists the % mRNA levels relative to an control duplex modified only with 2 DNA bases on the 3' end of the sense strand as assessed by qRT-PCR 24 hours after transfection into HeLa cells a 1 nM concentration.

| Sequence | (SEQ ID NO:) | FIG. 14 Name |
|---|---|---|
| 5' pGCACCAGAGCCAAUGGAACUUGAtg<br>3' UUCGUGGUCUCGGUUACCUUGAACUAC | 171<br>172 | 1 |
| 5' pGCACCAGAGCCAAUGGAACUUGAtg<br>3' UUCGUGGUCUCGGUUACCUUGAACUAC | 173<br>174 | 2 |
| 5' pGCACCAGAGCCAAUGGAACUUGAtg<br>3' UUCGUGGUCUCGGUUACCUUGAACUAC | 175<br>176 | 3 |
| 5' pGCACCAGAGCCAAUGGAACUUGAtg<br>3' UUCGUGGUCUCGGUUACCUUGAACUAC | 177<br>178 | 4 |
| 5' pGCACCAGAGCCAAUGGAACUUGAtg<br>3' UUCGUGGUCUCGGUUACCUUGAACUAC | 179<br>180 | 5 |
| 5' pGCACCAGAGCCAAUGGAACUUGAtg<br>3' UUCGUGGUCUCGGUUACCUUGAACUAC | 181<br>182 | 6 |
| 5' pGCACCAGAGCCAAUGGAACUUGAtg<br>3' UUCGUGGUCUCGGUUACCUUGAACUAC | 183<br>184 | 7 |

TABLE 19-continued 25-27mer Duplexes with Various Modification Patterns

| Sequence | (SEQ ID NO:) | FIG. 14 Name |
|---|---|---|
| 5' pGCACCAGAGCCAAUGGAACUUGAtg<br>3' UUCGUGGUCUCGGUUACCUUGAACUAC | 185<br>186 | 8 |
| 5' pGCACCAGAGCCAAUGGAACUUGAtg<br>3' UUCGUGGUCUCGGUUACCUUGAACUAC | 187<br>188 | 9 |
| 5' pGCACCAGAGCCAAUGGAACUUGAtg<br>3' UUCGUGGUCUCGGUUACCUUGAACUAC | 189<br>190 | 10 |
| 5' pG_c_A_cc_AGAG_cc_AAuGGAA_cu_UGAtg<br>3' U_uc_G_uGG_u_cuc_GG_uu_A_ccuu_GAACUAC | 191<br>192 | 11 |
| 5' pG_c_A_cc_AGAG_cc_AAuGGAA_cu_UGAtg<br>3' UUCGUGGUCUCGGUUACCUUGAACUAC | 193<br>194 | 12 |
| 5' pG_c_A_cc_AGAG_cc_AAuGGAA_cu_UGAtg<br>3' UUCGUGGUCUCGGUUACCUUGAACUAC | 195<br>196 | 13 |
| 5' pGCACCAGAGCCAAUGGAACUUGAtg<br>3' U_uc_G_uG_G_u_cuc_GG_uu_A_ccuu_GAACUAC | 197<br>198 | 14 |
| 5' pGCACCAGAGCCAAUGGAACUUGAtg<br>3' U_uc_G_u_GG_u_cuc_GG_uu_A_ccuu_GAACUAC | 199<br>200 | 15 |
| 5' pGCACCAGAGCCAAUGGAACUUGAtg<br>3' U_uc_GuGG_u_cuc_GGuu_A_ccuu_GAACUAC | 201<br>202 | 16 |
| 5' pGCACCAGAGCCAAUGGAACUUGAtg<br>3' U_uc_GuGG_u_cuc_GGuu_A_ccuu_GAACUAC | 203<br>204 | 17 |
| 5' pG_c_A_cc_AGAG_cc_AAuGGAA_cu_UGAtg<br>3' U_uc_GuGG_u_cuc_GGuu_A_ccuu_GAACUAC | 205<br>206 | 18 |

RNA = AGCU   2'OMe RNA = AGCU   2'F = _cu_   p = 5'-phos   DNA = tg

As with the 19-21mer duplexes, the 25-27mer RNA duplexes were transfected into HeLa cells in 24 well plate format using Oligofectamine RNAs were transfected at 10 nM and 1 nM concentrations in triplicate. At 24 hours post transfection, RNA was prepared from cultures and cDNA was made; qRT-PCR assays were performed in triplicate and data were normalized to RPLP0 (acidic ribosomal protein P0) mRNA levels, using the negative control siRNA as 100%. The results are listed in FIG. 14.

Results. In general, the more heavily modified duplexes showed reduced potency, particularly those that were extensively modified with both 2'-O-methyl and 2'-F bases. The less fully modified duplexes showed similar potency to the unmodified duplex. Patterns employing limited 2'-O-methyl modification routinely were favorable.

Based upon the results outlined in Example 16, patterns were selected that demonstrated high initial potency to study in greater detail. The following DsiRNA, termed "ASm" in the following examples, was chosen for further testing:

(SEQ ID NO: 179)
5' pGCACCAGAGCCAAUGGAACUUGAtg (SEQ ID NO: 207)
3' UUCGUGGUCUCGGUUACCUUGAACUAC

The DsiRNA is identical to the duplex formed by SEQ ID NO: 179 and 180 except the bases comprising the 3' overhang on the antisense strand are now modified with 2'-O-methyl. The ASm pattern has an antisense strand that is comprised of 27 monomers, contains 2'-O-methyl modified overhang bases as well as 2'-O-methyl modified alternating bases and optionally contains a 5' phosphate, and a sense strand that is comprised of 25 monomers wherein the two monomers on the 3' end are DNA and contains a 5' phosphate.

Example 17

Study of 2'-O-Methyl RNA Modification Patterns in EGFP

The next series of experiments were done using a dual-Luc Luciferase/EGFP fusion reporter. DsiRNAs were designed which targeted an enhanced green fluorescent protein (EGFP) sequence which was embedded in the 3'-UTR of the FLuc gene.

10 nM of each DsiRNA was co-transfected into HCT116 cells along with a single plasmid encoding both the target (Renilla) and Normalizer (Firefly) luciferase coding regions. (psiCheck-GFP with the blocked 27mers targeting the GFP sequence in Renilla. The dual luciferase assay (Promega) was performed 24 hr post-transfection and Renilla activity (target) was normalized to Firefly luciferase. The DsiRNAs tested are listed below in Table 20.

TABLE 20

DsiRNA modification patterns

Figure 15:
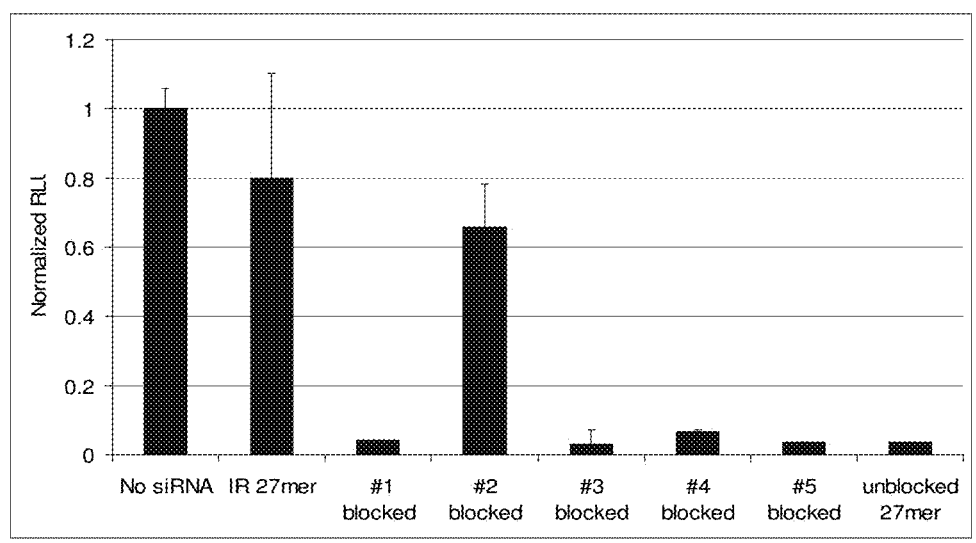
FIG. 15 demonstrates the relative performance of several modification patterns on DsiRNAs targeting the EGFP gene sequence. The results indicate that all single-strand modified variants worked well in reducing EGFP expression.

| Sequence | Duplex FIG. 15 Name | SEQ ID NO: |
|---|---|---|
| 5' pACCCUGAAGUUCAUCUGCACCACcg<br>3' ACUGGGACUUCAAGUAGACGUGGUGGC | #1 blocked | SEQ ID NO: 208<br>SEQ ID NO: 209 |
| 5' pACCCUGAAGUUCAUCUGCACCACcg<br>3' ACUGGGACUUCAAGUAGACGUGGUGGC | #2 blocked | SEQ ID NO: 210<br>SEQ ID NO: 211 |
| 5' pACCCUGAAGUUCAUCUGCACCACcg<br>3' ACUGGGACUUCAAGUAGACGUGGUGGC | #3 blocked | SEQ ID NO: 208<br>SEQ ID NO: 211 |
| 5' pACCCUGAAGUUCAUCUGCACCACcg<br>3' ACUGGGACUUCAAGUAGACGUGGUGGC | #4 blocked | SEQ ID NO: 208<br>SEQ ID NO: 212 |
| 5' pACCCUGAAGUUCAUCUGCACCACcg<br>3' ACUGGGACUUCAAGUAGACGUGGUGGC | #5 blocked | SEQ ID NO: 210<br>SEQ ID NO: 213 |
| 5' pACCCUGAAGUUCAUCUGCACCACcg<br>3' ACUGGGACUUCAAGUAGACGUGGUGGC | unblocked 27mer | SEQ ID NO: 208<br>SEQ ID NO: 213 |

RNA = AGCU   2'OMe RNA = AGCU   p = 5'-phos   DNA = cg

As shown in FIG. 15, all single-strand modified variants worked well, while the double-stranded modified variant did not. The ASm pattern (#3 blocked) performed well.

Example 18

Performance of ASm Designs in the Human HPRT1 Gene

ASm and related alternating 2'-O-methyl modification patterns of DsiRNAs were designed targeting the human HPRT gene (NM_000194) at a known potent site. The DsiRNAs are listed in Table 21.

TABLE 21

DsiRNAs tested with the human HPRT gene

Figure 16:
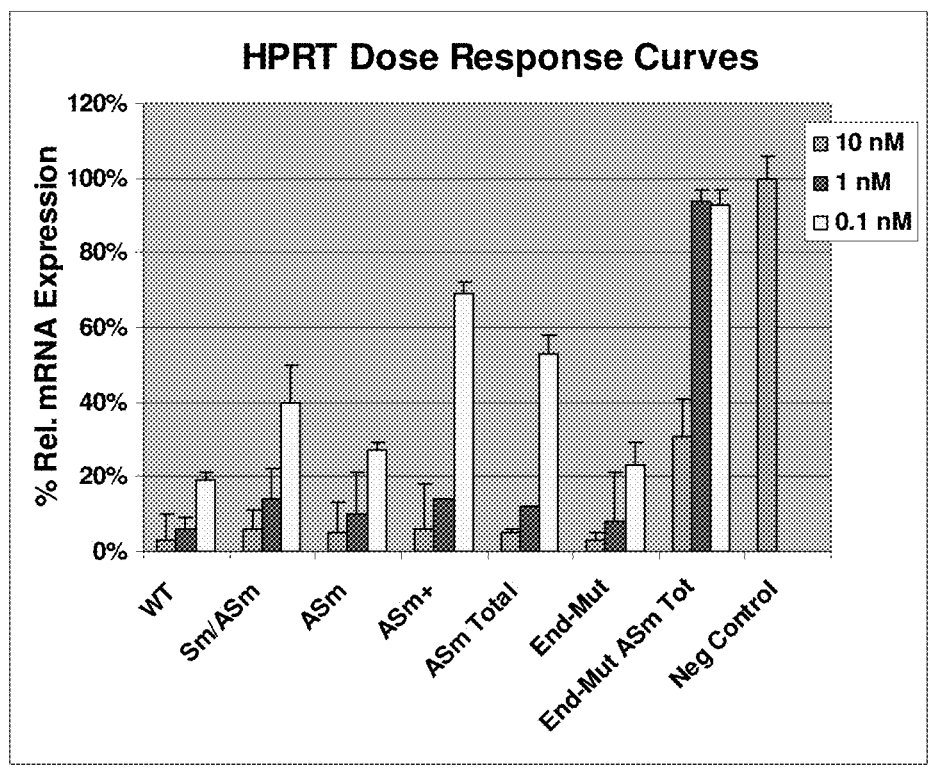
FIG. 16 shows the relative potency of several DsiRNA modification patterns against the human HPRT gene. Three doses were tested (10 nM, 1 nM, and 0.1 nM). The figure demonstrates not only that modified DsiRNAs work as well or nearly as well to unmodified DsiRNAs, but also that 25/27mers can potentially be loaded into RISC without Dicer cleavage.

| Sequence | Duplex FIG. 16 Name | SEQ ID NO: |
|---|---|---|
| 5' pGCCAGACUUUGUUGGAUUUGAAAtt<br>3'  UUCGGUCUGAAACAACCUAAACUUUAA | WT | SEQ ID NO: 214<br>SEQ ID NO: 215 |
| 5' pGCCAGACUUUGUUGGAUUUGAAAtt<br>3'  UUCGGUCUGAAACAACCUAAACUUUAA | Sm/ASm | SEQ ID NO: 216<br>SEQ ID NO: 217 |
| 5' pGCCAGACUUUGUUGGAUUUGAAAtt<br>3'  UUCGGUCUGAAACAACCUAAACUUUAA | ASm | SEQ ID NO: 214<br>SEQ ID NO: 217 |
| 5' pGCCAGACUUUGUUGGAUUUGAAAtt<br>3'  UUCGGUCUGAAACAACCUAAACUUUAA | ASm+ | SEQ ID NO: 214<br>SEQ ID NO: 218 |
| 5' pGCCAGACUUUGUUGGAUUUGAAAtt<br>3'  UUCGGUCUGAAACAACCUAAACUUUAA | ASm Total | SEQ ID NO: 214<br>SEQ ID NO: 219 |
| 5' pGCCAGACUUUGUUGGAUUUGAGCcg<br>3'  UUCGGUCUGAAACAACCUAAACUCGGC | End-Mut | SEQ ID NO: 220<br>SEQ ID NO: 221 |
| 5' pGCCAGACUUUGUUGGAUUUGAGCcg<br>3'  UUCGGUCUGAAACAACCUAAACUCGGC | End-Mut<br>ASm Tot | SEQ ID NO: 220<br>SEQ ID NO: 222 |
| 5' pCUUCCUCUCUUUCUCUCCCUUGUga<br>3'  AGGAAGGAGAGAAAGAGAGGGAACACU | Neg<br>Control | SEQ ID NO: 223<br>SEQ ID NO: 224 |

RNA = AGCU  2'OMe RNA = AGCU  p = 5'-phos  DNA = agct

Duplexes were transfected into HeLa cells using Oligofectamine at 10 nM, 1 nM, and 0.1 nM concentration. HeLa cells were split in 24 well plates at 35% confluency and were transfected the next day with Oligofectamine (Invitrogen, Carlsbad, Calif.) using 1 μL per 65 μL OptiMEM I with RNA duplexes at the indicated concentrations. All transfections were performed in triplicate. RNA was harvested at 24 hours post transfection using SV96 Total RNA Isolation Kit (Promega, Madison, Wis.). RNA was checked for quality using a Bioanalyzer 2100 (Agilent, Palo Alto, Calif.) and cDNA was prepared using 500 ng total RNA with SuperScript-II Reverse Transcriptase (Invitrogen, Carlsbad, Calif.) per manufacturer's instructions using both oligo-dT and random hexamer priming. Quantitative qRT-PCR was performed to assess relative knockdown of HPRT mRNA, using the RPLP0 gene as internal reference standard and negative control DsiRNA as 100% reference levels.

As illustrated in FIG. 16, the ASm modification pattern was most similar in potency to the unmodified DsiRNA duplex at the same site. The "ASm Total" duplex, which has alternating 2'OMe modifications throughout the entire AS strand, was also effective at reducing HPRT mRNA levels, albeit with lower potency than the WT or ASm versions at low dose (0.1 nM). Data from in vitro dicing assays indicates that the 2'-O-methyl modification pattern employed in the "ASm Total" duplex prevents normal processing by Dicer (see Example 20). The most straightforward interpretation of these data are that the intact 27 nt AS strand of this DsiRNA can directly load into RISC and trigger RNAi in the absence of Dicer cleavage into a 21mer siRNA.

To test this hypothesis, the "end-mut" mutant version of the HPRT DsiRNA was designed, wherein the terminal 4 bases of the sequence (5'-end of the AS strand) were mutated (see Table 21 sequence listing). This will block hybridization of the "seed region" if the 27mer loads intact, and should thus block or significantly reduce activity of this duplex to trigger RNAi-mediated suppression of HPRT mRNA. If Dicer cleavage occurs prior to RISC loading, the 4-base mutated domain will be cleaved off and the resulting 21mer product will be identical to the normal WT sequence.

The unmodified end-mut sequence showed potency similar to the WT HPRT DsiRNA, which is the expected result if Dicer cleavage occurred. The "ASm-total" version of the end-mut sequence, however, showed markedly reduced potency, which is the expected result if the mutant sequence were loaded into RISC without Dicer cleavage. It therefore appears that Dicer processing proceeds if the substrate dsRNA is cleavable (i.e., does not have nuclease resistant modifications spanning the cleavage site). If the DsiRNA is modified within the dicing site and cannot be processed by Dicer, the dsRNA can still function as a trigger for RNAi, presumably by RISC loading as an intact 27mer, but functions with reduced potency. It is therefore desirable, but not required, that modification patterns employed for DsiRNA employ cleavable bases and internucleoside linkages at the expected site of Dicer processing.

Example 19

Dicer Processing of ASm Modified HPRT DsiRNAs

In vitro dicing assays were performed on unmodified and modified duplexes. Duplexes were incubated with recombinant human Dicer and reaction products were subjected to ESI-MS (electrospray mass spectrometry). RNA duplexes (100 pmol) were incubated in 20 μL of 20 mM Tris pH 8.0, 200 mM NaCl, 2.5 mM MgCl$_2$ with or without 1 unit of recombinant human Dicer (Stratagene, La Jolla, Calif.) at 37° C. for 24 h. Samples were desalted using a Performa SR 96 well plate (Edge Biosystems, Gaithersburg, Md.). Electrospray-ionization liquid chromatography mass spectroscopy (ESI-LCMS) of duplex RNAs pre- and post-treatment with Dicer were done using an Oligo HTCS system (Novatia, Princeton, N.J.), which consisted of ThermoFinnigan TSQ7000, Xcalibur data system, ProMass data processing software and Paradigm MS4™ HPLC (Michrom BioResources, Auburn, Calif.). The liquid chromatography step employed before injection into the mass spectrometer (LC-MS) removes most of the cations complexed with the nucleic acids; some sodium ion can remain bound to the RNA and are visualized as minor +22 or +44 species, which is the net mass gain seen with substitution of sodium for hydrogen. All dicing experiments were performed at least twice. Mass data are summarized in Table 22.

TABLE 22

Resulting DsiRNAs post-Dicer processing

| Sequence | Sample | Mass(Da) | SEQ ID NO: |
|---|---|---|---|
| 5' pGCCAGACUUUGUUGGAUUUGAAAtt | WT | 8037 | 214 |
| 3' UUCGGUCUGAAACAACCUAAACUUUAA | | 8546 | 215 |
| 5' pGCCAGACUUUGUUGGAUUUGA | WT | 6771 | 225 |
| 3' UUCGGUCUGAAACAACCUAAAp | Diced | 6744 | 226 |
| 5' pGCCAGACUUUGUUGGAUUUGAAAtt | ASm | 8037 | 214 |
| 3' UUCGGUCUGAAACAACCUAAACUUUAA | | 8700 | 217 |
| 5' pGCCAGACUUUGUUGGAUUUGA | ASm (21) | 6771 | 227 |
| 3' UUCGGUCUGAAACAACCUAAAp | Diced | 6884 | 228 |
| 5' pGCCAGACUUUGUUGGAUUUGAA | ASm (22) | 7100 | 229 |
| 3' UUCGGUCUGAAACAACCUAAACp | Diced | 7189 | 230 |
| 5' pGCCAGACUUUGUUGGAUUUGAAAtt | ASm Total | 8037 | 214 |
| 3' UUCGGUCUGAAACAACCUAAACUUUAA | | 8756 | 219 |
| 5' pGCCAGACUUUGUUGGAUUUGAA | ASm Total | 7100 | 231 |
| 3' UUCGGUCUGAAACAACCUAAACUUUAA | Diced | 8756 | 219 |

RNA = AGCU 2'OMe RNA = AGCU p = 5'-phos DNA = agct

TABLE 23

Genes tested for IFN activation

| GENE ASSAY | GENE PROPERTIES |
|---|---|
| RPLP0 | ribosomal protein, housekeeping gene |
| HPRT | DsiRNA target, housekeeping gene |
| STAT1 | IRG |
| OAS1 | Receptor, cytoplasmic, detects long dsRNAs |
| IFITM1 | IRG |
| IFIT1 (p56) | IRG |
| RIG-I | Receptor, cytoplasmic, detects triphosphate and blunt RNAs |
| MDA5 | Receptor, cytoplasmic, detects short dsRNAs |
| TLR3 | Receptor, endocytic, detects dsRNAs |
| TLR4 | Receptor, cell surface, detects LPS |
| TLR7 | Receptor, endocytic, detects ssRNAs |
| TLR8 | Receptor, endocytic, detects ssRNAs |
| TLR9 | Receptor, endocytic, detects unmethylated CpG motif DNAs |

The unmodified HPRT DsiRNA diced into the expected 21mer species. The ASm modified HPRT DsiRNA diced into an equal mix of 21mer and 22mer products with cleavage occurring at the expected position. The ASm-total modified HPRT DsiRNA did not undergo normal Dicer processing. The unmodified S-strand was cleaved into a 22mer, however the 2'-O-Me modified AS strand remained uncut. The alternating 2'-O-methyl RNA pattern is therefore resistant to Dicer endonuclease cleavage.

Example 20

Measuring Interferon Responses Through qRT-PCR Assays

A panel of qRT-PCR assays were developed that are specific to human and mouse genes that involve recognition of nucleic acids by the innate immune system. Monitoring the relative levels of these genes is one approach to examine activation of immune pathways. The immune receptors, signaling molecules, interferon response genes (IRGs), and controls that were tested are listed in Table 23.

T98G cells were studied as these cells are known to strongly respond to dsRNAs in tissue culture. In particular, these cells have been shown to possess receptor/signaling pathways that can recognize longer RNAs of the type of the invention (Marques, et al. 2006). Two versions of an anti-HPRT DsiRNA, unmodified and ASm 2'-O-methyl modified (see Table 21 of Example 18), were transfected at high dose (100 nM) using siLentFect cationic lipid (Bio-Rad Laboratories). IFN pathway genes were assayed in cell culture at T=24 h post transfection using lipid alone as zero baseline. Two versions of an anti-HPRT DsiRNA, unmodified and ASm 2'-O-methyl modified (see Table 21 of Example 18), were transfected at high dose (100 nM) using siLentFect cationic lipid (Bio-Rad Laboratories). IFN pathway genes were assayed in cell culture at T=24 h post transfection using lipid alone as zero baseline.

Real-time PCR reactions were done using an estimated 33 ng cDNA per 25 μL reaction using Immolase DNA Polymerase (Bioline, Randolph, Mass.) and 200 nM primers and probe. Cycling conditions employed were: 50° C. for 2 minutes and 95° C. for 10 minutes followed by 40 cycles of 2-step PCR with 95° C. for 15 seconds and 60° C. for 1 minute. PCR and fluorescence measurements were done using an ABI Prism™ 7000 Sequence Detector or an ABI Prism™ 7900 Sequence Detector (Applied Biosystems Inc., Foster City, Calif.). All data points were performed in triplicate. Expression data was normalized to internal control human acidic ribosomal phosphoprotein P0 (RPLP0) (NM_001002) levels which were measured in separate wells in parallel.

The results are illustrated in FIG. 17A. Treatment of T98G cells with the unmodified DsiRNA resulted in potent stimulation of a number of IFN response genes and receptors within the innate immune system. Use of ASm 2'-O-methyl modified RNA resulted in minimal pathway activation. FIGS. 17B and 17C more clearly illustrate the control sequences. Both the RPLP0 (control) and HPRT (target) mRNAs are reduced to very low levels in cells treated with the unmodified DsiRNA, which is evidence that gross degradation of mRNA has taken place (typical of a Type-I IFN response), whereas in the ASm treated cells the control mRNA RPLP0 levels are normal while the target HPRT levels is reduced (indicative of successful RNAi suppression).

Figure 18:
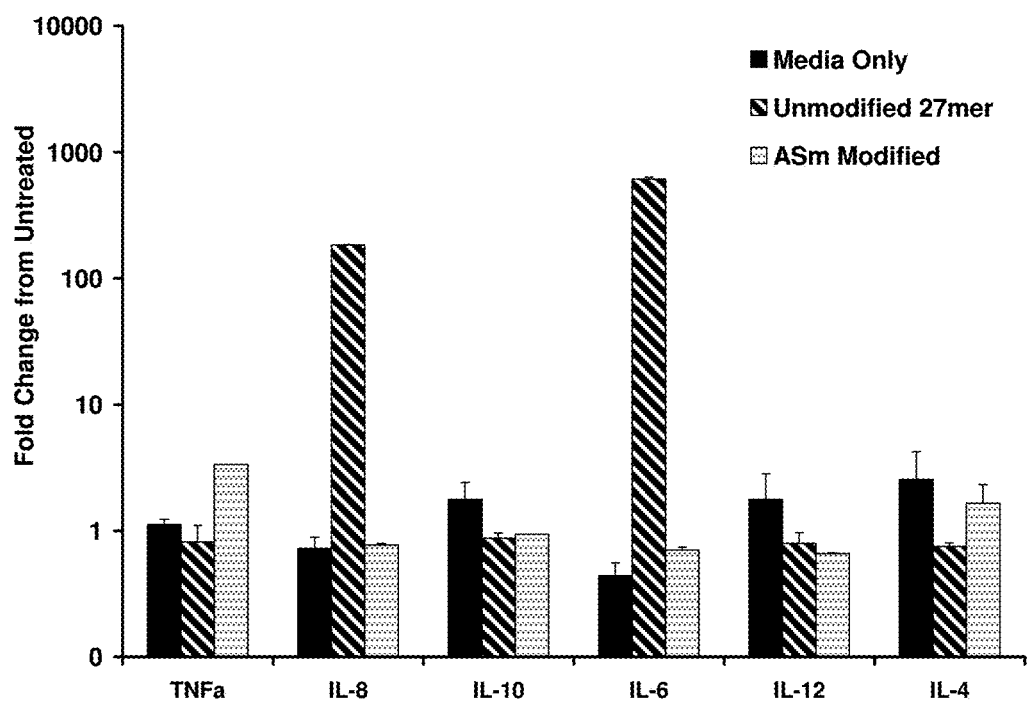
FIG. 18 demonstrates the change in secreted cytokine levels when 25/27mer DsiRNAs are introduced into T98G cells in tissue culture. Supernatants from the same cell cultures reported in Example 20, FIG. 17 for gene expression levels were assayed for the levels of various cytokines. Transfection of an unmodified HPRT DsiRNA resulted in significant elevations of IL-8 and IL-6 cytokine levels, indicative of strong stimulation of an immune signaling pathway. Transfection of the same sequence modified with 2'-O-methyl RNA in the ASm pattern did not show significant elevation of any cytokines.

FIG. 18 demonstrates that when using unmodified RNA, high release levels of the inflammatory cytokines IL-8 and IL-6 were observed. When the same sequence was transfected modified with 2'-O-methyl RNA in the ASm pattern, no significant elevation of cytokine levels was observed.

Example 22

Serum Stability for DsiRNAs

The following example demonstrates the relative level of protection from nuclease degradation that is conferred on DsiRNAs with and without modifications.

RNAs were incubated in 50% fetal bovine serum for various periods of time (up to 24 h) at 37° C. Serum was extracted and the nucleic acids were separated on a 20% nondenaturing PAGE and visualized with Gelstar stain. Markers are blunt, duplex RNAs of the indicated lengths. Sequences studied are listed in Table 24.

TABLE 24

DsiRNA tested for stability in serum

Figure 19:
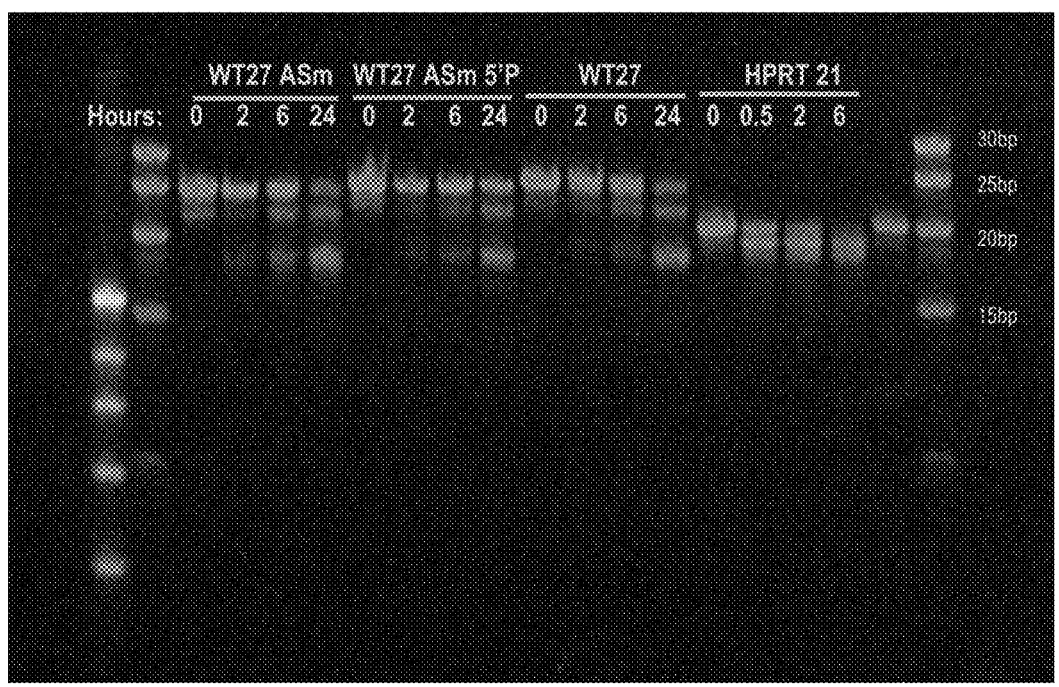
FIG. 19 demonstrates the improved stability of modified 27mer DsiRNA designs compared to unmodified DsiRNA and 21mer siRNA duplexes. RNA duplexes were incubated at 37° C. for the indicated length of time in 50% fetal bovine serum, extracted, and separated on polyacrylamide gel electrophoresis. Unmodified 27mer DsiRNA duplexes showed improved stability compared with unmodified 21mer duplexes and best stability was seen with the 2'-O-methyl ASm+5'P modification pattern.

| Sequence | Duplex FIG. 19 Name | SEQ ID NO: |
|---|---|---|
| 5' pGCCAGACUUUGUUGGAUUUGAAAtt | WT27 | SEQ ID NO: 214 |
| 3' UUCGGUCUGAAACAACCUAAACUUUAA | | SEQ ID NO: 215 |
| 5' pGCCAGACUUUGUUGGAUUUGAAAtt | WT27 ASm | SEQ ID NO: 214 |
| 3' UUCGGUCUGAAACAACCUAAACUUUAA | | SEQ ID NO: 217 |
| 5'   GCCAGACUUUGUUGGAUUUGA | HPRT 21 | SEQ ID NO: 232 |
| 3' UUCGGUCUGAAACAACCUAAA | | SEQ ID NO: 233 |
| 5' pGCCAGACUUUGUUGGAUUUGAAAtt | WT27 ASm | SEQ ID NO: 214 |
| 3' UUCGGUCUGAAACAACCUAAACUUUAAp | 5'P | SEQ ID NO: 234 |

RNA = AGCU   2'OMe RNA = AGCU   p = 5'-phos   DNA = tt

Example 21

Measuring Immune Response to DsiRNAs Using Cytokine Assays

It is well known in the art that dsRNAs (including 21mer siRNAs) are at risk of triggering an innate immune response (classically a Type-I IFN response) when administered in vivo, particularly when given complexed with lipid-based delivery reagents that maximize exposure to the endosomal compartments where Toll-Like Receptors (TLRs) 3, 7, and 8 reside. Modification with 2'-O-methyl RNA in 21mers has been shown to generally prevent IFN activation (Judge et al., Molecular Therapy 2006).

Cytokine assays were performed using reagents from Upstate (Millipore). These are antibody-based assays which run in multiplex using the Luminex fluorescent microbead platform. Standard curves were established to permit absolute quantification. Assays were performed according to the manufacturer's recommendation.

T98G cells were studied for cytokine release following transfection with modified and unmodified HPRT DsiRNAs. Supernatants from the same cultures that were studied for gene expression in Example 20 were employed, so cytokine secretion and gene expression can be directly contrasted within the same experiment. RNAs were transfected at high dose (100 nM) using siLentFect (cationic lipid). Cytokine assays were performed on culture supernatants at T=24 h post transfection using lipid alone as zero baseline.

As illustrated in FIG. 19, the 27mer DsiRNAs showed improved stability in serum even without chemical modification. Addition of 2'-O-methyl RNA in the ASm pattern did not appear to improve stability by this assay. The ASm+5'P modification pattern did improve stability. The 21mer siRNAs showed rapid degradation to species that likely represents a blunt 19mer (first step of degradation is removal of the ssRNA 3'-overhangs). Degradation of the duplex dsRNA domain is slower.

RNAs that have been subjected to serum degradation were separated by HPLC and the peaks purified; actual degradation products were identified by LC-MS using the Novatia ESI-MS platform (methods as described previously for in vitro dicing assays). Interestingly, the band that appears to be intact by PAGE methods (FIG. 21) actually is a mixed population including intact and partially degraded RNAs. Mass analysis revealed the presence of a 5'-exonuclease activity that is blocked by 5'-phosphate, so that the duplex bearing 5'-phosphate groups on both strands (ASm+5'P) was more intact than the unmodified or ASm modified duplexes. The relative amount of intact DsiRNA present after 24 h incubation in serum was ASm+5'P>ASm>WT unmodified. 5'-phosphate is present on naturally occurring miRNAs and siRNAs that result from Dicer processing. Addition of 5'-phosphate to all strands in synthetic RNA duplexes may be an inexpensive and physiological method to confer some limited degree of nuclease stability.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Allerson, C. R. et al. (2005). Fully 2'-modified oligonucleotide duplexes with improved in vitro potency and stability compared to unmodified small interfering RNA. *J Med Chem*, 48, 901-904.

Amarzguioui, M. and Prydz (2004). An algorithm for selection of functional siRNA sequences. *Biochem Biophys Res Commun* 316:1050-1058.

Amarzguioui, M. et al. (2003). Tolerance for Mutation and Chemical Modifications in a siRNA. *Nucleic Acids Research* 31:589-595.

Bartlett, D. W. and Davis, M. E. (2006) Effect of siRNA nuclease stability on the in vitro and in vivo kinetics of siRNA-mediated gene silencing. *Biotechnol Bioeng*.

Beale, S. E. et al. (2005). siRNA target site secondary structure predictions using local stable substructures. *Nucl Acids Res* 33:e30 (pp 1-10).

Beck, W. T. (1989). Unknotting the complexities of multidrug resistance: the involvement of DNA topoisomerases in drug action and resistance. *J Natl Cancer Inst* 81:1683-1685.

Bernstein, E. et al. (2001) Role for a bidentate ribonuclease in the initiation step of RNA interference. *Nature* 409: 363-366.

Boese, Q. et al. (2005). Mechanistic insights aid computational short intervening RNA design. *Methods Enzymol* 392:73-96.

Bondensgaard, K. et al. (2000). Structural studies of LNA: RNA duplexes by NMR: conformations and implications for RNase H activity. *Chemistry* 6:2687-2695.

Braasch, D. A. and Corey, D. R. (2001). Locked nucleic acid (LNA): fine-tuning the recognition of DNA and RNA. *Chem Biol* 8:1-7.

Braasch et al. (2003). RNA Interference in Mammalian Cells by Chemically-Modified RNA. *Biochemistry* 42:7967-7975.

Bohula, E. A. et al. (2003). The efficacy of small interfering RNAs targeted to the type 1 insulin-like growth factor receptor (IGF1R) is influenced by secondary structure in the IGF1R transcript. *J Biol Chem* 278:15991-15997.

Bridge et al. (2003). Induction of an Interferon Response by RNAi Vectors in Mammalian Cells. *Nature Genetics* 34:263-264.

Caplen, N.J. et al. (2001). Specific inhibition of gene expression by small double-stranded RNAs in invertebrate and vertebrate systems. *Proc Natl Acad Sci USA* 98:9742-9747.

Chang et al. (1985). Gene Expression from Both Intronless and Intron-Containing Rous Sarcoma Virus Clones is Specifically Inhibited by Anti-Sense RNA. *Molecular and Cellular Biology* 5:2341-2348.

Check (2003). RNA to the Rescue? *Nature* 425:10-12.

Childs, S. and V. Ling (1994). The MDR superfamily of genes and its biological implications. *Important Adv Oncol*, pp. 21-36.

Chiu et al. (2003). siRNA Function in RNAi: A Chemical Modification Analysis. *RNA* 9:1034-1048.

Chiu, Y. L., and Rana, T. R. (2002). RNAi in human cells: basic structural and functional features of small interfering RNA. *Mol Cell* 10:549-561.

Choung, S. et al. (2006). Chemical modification of siRNAs to improve serum stability without loss of efficacy. *Biochem Biophys Res Commun*, 342, 919-927.

Cole, S. P. et al. (1992). Overexpression of a transporter gene in a multidrug-resistant human lung cancer cell line. *Science* 258:1650-1654.

Crinelli, R. et al. (2002). Design and characterization of decoy oligonucleotides containing locked nucleic acids. *Nucleic Acids Res* 30:2435-2443.

Czauderna et al. (2003). Structural Variations and Stabilising Modifications of Synthetic siRNAs in Mammalian Cells. *Nucleic Acids Research* 31:2705-2716.

Damha, M. J., and Ogilvie, K. K. (1993). Oligoribonucleotide synthesis. The silyl-phosphoramidite method. *Methods Mol Biol* 20:81-114.

Eckstein, F. (2000). Phosphorothioate oligodeoxynucleotides: what is their origin and what is unique about them? *Antisense Nucleic Acid Drug Dev* 10:117-21.

Eder, P. S. et al. (1991). Substrate specificity and kinetics of degradation of antisense oligonucleotides by a 3' exonuclease in plasma. *Antisense Res Dev*, 1, 141-151.

Elbashir, S. M. et al. (2001a). Duplexes of 21-nucleotide RNAs mediate RNA interference in cultured mammalian cells. *Nature* 411:494-498.

Elbashir, S. M. et al. (2001b). RNA interference is mediated by 21- and 22-nucleotide RNAs. *Genes & Dev* 15:188-200.

Elbashir, S. M. et al. (2001c). Functional Anatomy of siRNAs for Mediating Efficient RNAi in *Drosophila melanogaster* Embryo Lysate. *EMBO J* 20:6877-6888.

Elman, J. et al. (2005). Locked nucleic acid (LNA) mediated improvements in siRNA stability and functionality. *Nucleic Acids Res* 33:439-447.

Fan., D. et al., (1994). Reversal of multidrug resistance In *Reversal of Multidrug Resistance in Cancer*, Kellen, J. A., ed., CRC Press, Boca Raton, Fla., pp. 93-125.

Fire, A. et al. (1998). Potent and specific genetic interference by double-stranded RNA in *Caenorhabditis elegans*. *Nature* 391:806-811.

Graessmann, M. et al. (1991) Inhibition of SV40 gene expression by microinjected small antisense RNA and DNA molecules. *Nucleic Acids Res* 19:53-59.

Grunweller, A. et al. (2003). Comparison of different antisense strategies in mammalian cells using locked nucleic acids, 2'-O-methyl RNA, phosphorothioates and small interfering RNA. *Nucleic Acids Res,* 31, 3185-3193.

Gunnery, S., and Mathews, M. B. (1998) RNA binding and modulation of PKR activity. *Methods* 15:189-98.

Hall, A. H. et al. (2004). RNA interference using boranophosphate siRNAs: structure-activity relationships. *Nucleic Acids Res,* 32, 5991-6000.

Hall, A. H. et al. (2006). High potency silencing by single-stranded boranophosphate siRNA. *Nucleic Acids Res,* 34, 2773-2781.

Hamada et al. (2002). Effects on RNA Interference in Gene Expression (RNAi) in Cultured Mammalian Cells of Mismatches and the Introduction of Chemical Modifications at the 3'-Ends of siRNAs. *Antisense and Nucleic Acid Drug Development* 12:301-309.

Hannon (2002). RNA Interference. *Nature* 418:244-251.

Harborth, J. et al. (2003). Sequence, chemical, and structural variation of small interfering RNAs and short hairpin RNAs and the effect on mammalian gene silencing. *Antisense Nucleic Acid Drug Dev* 13:83-105.

Haupenthal, J. et al. (2006) Inhibition of RNAse A family enzymes prevents degradation and loss of silencing activity of siRNAs in serum. *Biochem Pharmacol,* 71, 702-710.

Haupenthal, J. et al. (2007). RNAse A-like enzymes in serum inhibit the anti-neoplastic activity of siRNA targeting polo-like kinase 1. *Int J Cancer.*

Heidel, J. D. et al. (2004). Lack of interferon response in animals to naked siRNAs. *Nat Biotechnol,* 22, 1579-1582.

Herdewijn, P. (2000). Heterocyclic modifications of oligonucleotides and antisense technology. *Antisense Nucleic Acid Drug Dev* 10:297-310.

Hohjoh, J. (2002) RNA interference (RNAi) induction with various types of synthetic oligonucleotide duplexes in cultured human cells. *FEBS Lett* 521:195-199.

Holen, T. (2002). Positional effects of short interfering RNAs targeting the human coagulation trigger tissue factor. *Nucleic Acids Res* 30:1757-1766.

Hong, J. et al. (2005). High doses of siRNAs induce eri-1 and adar-1 gene expression and reduce the efficiency of RNA interference in the mouse. *Biochem J,* 390, 675-679.

Jackson, A. L. et al. (2003). Expression profiling reveals off-target gene regulation by RNAi. *Nat Biotechno.* 21:635-637.

Jackson, A. L. et al. (2006). Position-specific chemical modification of siRNAs reduces "off-target" transcript silencing. *Rna,* 12, 1197-1205.

Ji, J. et al. (2003). Enhanced gene silencing by the application of multiple specific small interfering RNAs. *FEBS Lett* 552:247-252.

Judge, A. D. et al. (2006). Design of noninflammatory synthetic siRNA mediating potent gene silencing in vivo. *Mol Ther,* 13, 494-505.

Kariko, K. et al. (2005). Suppression of RNA recognition by Toll-like receptors: the impact of nucleoside modification and the evolutionary origin of RNA. *Immunity,* 23, 165-175.

Kennedy, S. et al. (2004). A conserved siRNA-degrading RNase negatively regulates RNA interference in *C. elegans*. *Nature,* 427, 645-649.

Khvorova, A. et al. (2003). Functional siRNAs and miRNAs exhibit strand bias. *Cell* 115:209-216.

Kim, D. H., and J. J. Rossi (2003). Coupling of RNAi-mediated target downregulation with gene replacement. *Antisense* Nucleic Acid Drug Dev 13:151-155.

Kim, D. H. et al. (2004). Interferon induction by siRNAs and ssRNAs synthesized by phage polymerase. *Nat Biotechnol* 22:321-325.

Kraynack, B. A. and Baker, B. F. (2006) Small interfering RNAs containing full 2'-O-methylribonucleotide-modified sense strands display Argonaute2/eIF2C2-dependent activity. *Rna,* 12, 163-176.

Kretshmer-Kazemi Far et al. (2003). The Activity of siRNA in Mammalian Cells is Related to Structural Target Accessibility: A Comparison with Antisense Oligonucleotides. *Nucleic Acids Research* 31: 4417-4424.

Krol, J. et al. (2004). Structural features of microRNA (miRNA) precursors and their relevance to miRNA biogenesis and small interfering RNA/short hairpin RNA design. *J Biol Chem* 279:42230-42239.

Kreuter, J. (1991) Nanoparticles-preparation and applications. In: *Microcapsules and nanoparticles in medicine and pharmacy*, Donbrow M., ed, CRC Press, Boca Raton, Fla., pp. 125-14.

Kurreck, J. et al. (2002). Design of antisense oligonucleotides stabilized by locked nucleic acids. *Nucleic Acids Res* 30:1911-1918.

Kurreck, J. (2003) Antisense technologies Improvement through novel chemical modifications. *Eur J Biochem,* 270, 1628-1644.

Levin, A. A. (1999) A review of the issues in the pharmacokinetics and toxicology of phosphorothioate antisense oligonucleotides. *Biochim Biophys Acta,* 1489, 69-84.

Liu, et al. (2003). R2D2, a Bridge Between the Initiator and Effector Steps of the *Drosophila* RNAi Pathway. *Science* 301:1921-1925.

Ma, Z. et al. (2005). Cationic lipids enhance siRNA-mediated interferon response in mice. *Biochem Biophys Res Commun,* 330, 755-759.

Manche, L. et al. (1992). Interactions between double-stranded RNA regulators and the protein kinase DAI. *Mol Cell Biol* 12:5238-5248.

Manoharan, M. (2002) Oligonucleotide conjugates as potential antisense drugs with improved uptake, biodistribution, targeted delivery, and mechanism of action. *Antisense Nucleic Acid Drug Dev,* 12, 103-128.

Markovtsov, V. et al. (2000). Cooperative assembly of an hnRNP complex induced by a tissue specific homolog of polypyrimidine tract binding protein. *Mol Cell Biol* 20:7463-79.

Marques, J. T. and Williams, B. R. (2005) Activation of the mammalian immune system by siRNAs. *Nat Biotechnol,* 23, 1399-1405.

Marques, J. T., et al. (2006). A structural basis of discriminating between self and nonself double-stranded RNAs in mammalian cells. *Nature Biotechnology,* 24:559-565.

Martinez, J. et al. (2002). Single-stranded antisense siRNAs guide target RNA cleavage in RNAi. *Cell* 110:563-574.

Matteucci, M. (1997) Oligonucleotide analogues: an overview. *Ciba Found Symp,* 209, 5-14; discussion 14-18.

McManus et al. (2002). Gene Silencing in Mammals by Small Interfering RNAs. *Nature Reviews Genetics* 3:737-747.

Melton, D. A. (1985). Injected anti-sense RNAs specifically block messenger RNA translation in vivo. *Proc Natl Acad Sci USA* 82:144-148.

Minks, M. A. et al. (1979). Structural requirements of double-stranded RNA for the activation of the 2'-5'-oligo (A) polymerase and protein kinase of interferon-treated HeLa cells. *J Biol Chem* 254:10180-10183.

Mook, O. R. et al. (2007). Evaluation of locked nucleic acid-modified small interfering RNA in vitro and in vivo. *Mol Cancer Ther,* 6, 833-843.

Morrissey, D. V. et al. (2005a). Activity of stabilized short interfering RNA in a mouse model of hepatitis B virus replication. *Hepatology,* 41, 1349-1356.

Morrissey, D. V. et al. (2005b). Potent and persistent in vivo anti-HBV activity of chemically modified siRNAs. *Nat Biotechnol,* 23, 1002-1007.

Napoli, C. et al. (1990). Introduction of a chimeric chalcone synthase gene into *petunia* results in reversible co-suppression of homologous genes in trans. *Plant Cell* 2:279-289.

Nawrot, B. and Sipa, K. (2006) Chemical and structural diversity of siRNA molecules. *Curr Top Med Chem,* 6, 913-925.

Ngo et al. (1998). Double-Stranded RNA Induces mRNA Degradation in *Trypanosoma brucei. Proc Natl Acad Sci USA* 95:14687-14692.

Parrish, S. et al. (2000). Functional anatomy of a dsRNA trigger: differential requirements for the two trigger strands in RNA interference. *Mol Cell* 6:1077-1087.

Pellino et al. (2003). R2D2 Leads the Silencing Trigger to mRNA's Death Star. *Cell* 115:132-133.

Persengiev, S. P. et al. (2004). Nonspecific, concentration-dependent stimulation and repression of mammalian gene expression by small interfering RNAs (siRNAs). *RNA* 10:12-18.

Prakash, T. P. et al. (2005). Positional effect of chemical modifications on short interference RNA activity in mammalian cells. *J Med Chem,* 48, 4247-4253.

Raemdonck, K. et al. (2006). In situ analysis of single-stranded and duplex siRNA integrity in living cells. *Biochemistry,* 45, 10614-10623.

Rana, T. M. (2007) Illuminating the silence: understanding the structure and function of small RNAs. *Nat Rev Mol Cell Biol,* 8, 23-36.

Rehwinkel, J. et al. (2005). A crucial role for GW182 and the DCP1:DCP2 decapping complex in miRNA-mediated gene silencing. *Rna,* 11, 1640-1647.

Reynolds, A. et al. (2004). Rational siRNA design for RNA interference. *Nat Biotechnol* 22:326-330.

Robbins, M. A. et al. (2006). Stable expression of shRNAs in human CD34(+) progenitor cells can avoid induction of interferon responses to siRNAs in vitro. *Nat Biotechnol,* 24, 566-571.

Romano, N. and G. Macino (1992). Quelling: transient inactivation of gene expression in *Neurospora crassa* by transformation with homologous sequences. *Mol Microbiol* 6:3343-53.

Rusckowski, M. et al. (2000). Biodistribution and metabolism of a mixed backbone oligonucleotide (GEM 231) following single and multiple dose administration in mice. *Antisense Nucleic Acid Drug Dev* 10:333-345.

Scheffer, G. L. et al. (1995). The drug resistance-related protein LRP is the human major vault protein. *Nat Med* 1:578-582.

Scherer, L. and J. J. Rossi (2004). RNAi applications in mammalian cells. *Biotechniques* 36:557-561.

Scherer et al. (2003). Approaches for the Sequence-Specific Knockdown of mRNA, *Nature Biotechnology* 21:1457-1465.

Schlee, M. et al. (2006). siRNA and isRNA: two edges of one sword. *Mol Ther,* 14, 463-470.

Schwarz, D. S. et al. (2003). Asymmetry in the assembly of the RNAi enzyme complex. *Cell* 115:199-208.

Shen, L. et al. (2003). Evaluation of C-5 propynyl pyrimidine-containing oligonucleotides in vitro and in vivo. *Antisense Nucleic Acid Drug Dev,* 13, 129-142.

Siolas, D. et al. (2005). Synthetic shRNAs as potent RNAi triggers. *Nat Biotechnol* 23:227-231.

Sioud, M. and Sorensen, D. R. (2003) Cationic liposome-mediated delivery of siRNAs in adult mice. *Biochem Biophys Res Commun,* 312, 1220-1225.

Sioud, M. (2005) Induction of inflammatory cytokines and interferon responses by double-stranded and single-stranded siRNAs is sequence-dependent and requires endosomal localization. *J Mol Biol,* 348, 1079-1090.

Skipper, (2003). Elegant Tour de Force. *Nature Reviews Genetics* 4: 79-80.

Sledz et al. (2003). Activation of the Interferon System by Short-Interfering RNAs. *Nature Cell Biology* 5:834-839.

Soutschek, J. et al. (2004). Therapeutic silencing of an endogenous gene by systemic administration of modified siRNAs. *Nature,* 432, 173-178.

Stark, G. R. et al. (1998). How cells respond to interferons. *Annu Rev Biochem* 67:227-264.

Stein, D. A. et al. (2001) Inhibition of Vesivirus infections in mammalian tissue culture with antisense morpholino oligomers. *Antisense Nucleic Acid Drug Dev* 11:317-25.

Swayze, E. E. et al. (2007). Antisense oligonucleotides containing locked nucleic acid improve potency but cause significant hepatotoxicity in animals. *Nucleic Acids Res,* 35, 687-700.

Turner, J. J. et al. (2007). MALDI-TOF mass spectral analysis of siRNA degradation in serum confirms an RNAse A-like activity. *Mol Biosyst,* 3, 43-50.

Tuschl, T. et al. (1999). Targeted mRNA degradation by double-stranded RNA in vitro. *Genes & Dev* 13:3191-3197.

Ui-Tei, K. et al. (2004). Guidelines for the selection of highly effective siRNA sequences for mammalian and chick RNA interference. *Nucleic Acids Res* 32:936-948.

Verma, S. and F. Eckstein (1998). Modified oligonucleotides: synthesis and strategy for users. *Annu Rev Biochem* 67:99-134.

Vorobjev, P. E. et al. (2001). Nuclease resistance and RNase H sensitivity of oligonucleotides bridged by oligomethylenediol and oligoethylene glycol linkers. *Antisense Nucleic Acid Drug Dev* 11:77-85.

Wahlestedt, C. et al. (2000). Potent and nontoxic antisense oligonucleotides containing locked nucleic acids. *Proc Natl Acad Sci USA* 97:5633-5638.

Waterhouse et al. (2003). Exploring Plant Genomes by RNA-Induced Gene Silencing. *Nature Reviews Genetics* 4: 29-38.

Wincott, F. et al. (1995). Synthesis, deprotection, analysis and purification of RNA and ribozymes. *Nucleic Acids Res* 23:2677-84.

Wolin, S. L. and T. Cedervall (2002). The La protein. *Annu Rev Biochem* 71:375-403.

Xu et al. (2003). Effective Small Interfering RNAs and Phosphorothioate Antisense DNAs Have Different Preferences for Target Sites in the Luciferase mRNAs. *Biochemical and Biophysical Research Communications* 306:712-717.

Yang, X. C. et al. (2006). Characterization of 3'hExo, a 3' exonuclease specifically interacting with the 3' end of histone mRNA. *J Biol Chem,* 281, 30447-30454.

Yuan, B. et al. (2004). siRNA Selection Server: an automated siRNA oligonucleotide prediction server. *Nucl Acids Res* 32(Webserver issue):W130-134.

Zamore, P. D. et al. (2000). RNAi: double-stranded RNA directs the ATP-dependent cleavage of mRNA at 21 to 23 nucleotide intervals. *Cell* 101:25-33.

Zhang, H. Y. et al. (2006). RNA Interference with chemically modified siRNA. *Curr Top Med Chem,* 6, 893-900.

What is claimed is:

1. A formulation comprising a nucleic acid molecule capable of reducing the expression of a target gene, the nucleic acid molecule comprising:
   a first oligonucleotide strand that is 25-30 nucleotides in length and contains 1-3 DNA bases on the 3' end of the first oligonucleotide strand; and
   a second oligonucleotide strand that is 25-30 nucleotides in length comprising an overhang of unmodified and/or modified nucleotides and a domain that hybridizes to the first oligonucleotide strand comprising unmodified and modified nucleotides,
   wherein said second oligonucleotide strand is sufficiently complementary to a target mRNA encoded by said target gene to reduce target gene expression when said nucleic acid molecule is introduced into a subject or a cell derived from said subject.

* * * * *

SEQUENCE LISTING

```
<160> NUMBER OF SEQ ID NOS: 234

<210> SEQ ID NO 1
<211> LENGTH: 720
<212> TYPE: DNA
<213> ORGANISM: Artificial
<220> FEATURE:
<223> OTHER INFORMATION: EGFP from cloning vector pEGFP-C1

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 2
<211> LENGTH: 39
<212> TYPE: RNA
<213> ORGANISM: Artificial
<220> FEATURE:
<223> OTHER INFORMATION: mRNA from EGFP from cloning vector pEGFP-C1

<400> SEQUENCE: 2
gcaagcugac ccugaaguuc aucugcacca ccggcaagc                             39

<210> SEQ ID NO 3
<211> LENGTH: 21
<212> TYPE: RNA
<213> ORGANISM: Artificial
<220> FEATURE:
<223> OTHER INFORMATION: siRNA

<400> SEQUENCE: 3
gcaagcugac ccugaaguuc a                                                21

<210> SEQ ID NO 4
<211> LENGTH: 21
<212> TYPE: RNA
<213> ORGANISM: Artificial
<220> FEATURE:
<223> OTHER INFORMATION: siRNA

<400> SEQUENCE: 4
gaugaacuuc agggucagcu u                                                21
```

```
<210> SEQ ID NO 5
<211> LENGTH: 21
<212> TYPE: RNA
<213> ORGANISM: Artificial
<220> FEATURE:
<223> OTHER INFORMATION: siRNA

<400> SEQUENCE: 5
aagcugaccc ugaaguucau c                                              21

<210> SEQ ID NO 6
<211> LENGTH: 21
<212> TYPE: RNA
<213> ORGANISM: Artificial
<220> FEATURE:
<223> OTHER INFORMATION: siRNA

<400> SEQUENCE: 6
gaugaacuuc agggucagcu u                                              21

<210> SEQ ID NO 7
<211> LENGTH: 21
<212> TYPE: RNA
<213> ORGANISM: Artificial
<220> FEATURE:
<223> OTHER INFORMATION: siRNA

<400> SEQUENCE: 7
ccugaaguuc aucugcacca c                                              21

<210> SEQ ID NO 8
<211> LENGTH: 21
<212> TYPE: RNA
<213> ORGANISM: Artificial
<220> FEATURE:
<223> OTHER INFORMATION: siRNA

<400> SEQUENCE: 8
ggugcagaug aacuucaggg u                                              21

<210> SEQ ID NO 9
<211> LENGTH: 21
<212> TYPE: RNA
<213> ORGANISM: Artificial
<220> FEATURE:
<223> OTHER INFORMATION: siRNA

<400> SEQUENCE: 9
cccugaaguu caucugcacc a                                              21

<210> SEQ ID NO 10
<211> LENGTH: 21
<212> TYPE: RNA
<213> ORGANISM: Artificial
<220> FEATURE:
<223> OTHER INFORMATION: siRNA

<400> SEQUENCE: 10
gugcagauga acuucagggu c                                              21

<210> SEQ ID NO 11
<211> LENGTH: 21
<212> TYPE: RNA
<213> ORGANISM: Artificial
<220> FEATURE:
```

```
<223> OTHER INFORMATION: siRNA

<400> SEQUENCE: 11
acccugaagu ucaucugcac c                                              21

<210> SEQ ID NO 12
<211> LENGTH: 21
<212> TYPE: RNA
<213> ORGANISM: Artificial
<220> FEATURE:
<223> OTHER INFORMATION: siRNA

<400> SEQUENCE: 12
ugcagaugaa cuucagqguc a                                              21

<210> SEQ ID NO 13
<211> LENGTH: 21
<212> TYPE: RNA
<213> ORGANISM: Artificial
<220> FEATURE:
<223> OTHER INFORMATION: siRNA

<400> SEQUENCE: 13
gacccugaag uucaucugca c                                              21

<210> SEQ ID NO 14
<211> LENGTH: 21
<212> TYPE: RNA
<213> ORGANISM: Artificial
<220> FEATURE:
<223> OTHER INFORMATION: siRNA

<400> SEQUENCE: 14
gcagaugaac uucaggguca g                                              21

<210> SEQ ID NO 15
<211> LENGTH: 21
<212> TYPE: RNA
<213> ORGANISM: Artificial
<220> FEATURE:
<223> OTHER INFORMATION: siRNA

<400> SEQUENCE: 15
ugacccugaa guucaucugc a                                              21

<210> SEQ ID NO 16
<211> LENGTH: 21
<212> TYPE: RNA
<213> ORGANISM: Artificial
<220> FEATURE:
<223> OTHER INFORMATION: siRNA

<400> SEQUENCE: 16
cagaugaacu ucaggqucag c                                              21

<210> SEQ ID NO 17
<211> LENGTH: 21
<212> TYPE: RNA
<213> ORGANISM: Artificial
<220> FEATURE:
<223> OTHER INFORMATION: siRNA

<400> SEQUENCE: 17
cugacccuga aguucaucug c                                              21
```

```
<210> SEQ ID NO 18
<211> LENGTH: 21
<212> TYPE: RNA
<213> ORGANISM: Artificial
<220> FEATURE:
<223> OTHER INFORMATION: siRNA

<400> SEQUENCE: 18
agaugaacuu cagggucagc u                                              21

<210> SEQ ID NO 19
<211> LENGTH: 21
<212> TYPE: RNA
<213> ORGANISM: Artificial
<220> FEATURE:
<223> OTHER INFORMATION: siRNA

<400> SEQUENCE: 19
gcugacccug aaguucaucu g                                              21

<210> SEQ ID NO 20
<211> LENGTH: 21
<212> TYPE: RNA
<213> ORGANISM: Artificial
<220> FEATURE:
<223> OTHER INFORMATION: siRNA

<400> SEQUENCE: 20
gaugaacuuc agggucagcu u                                              21

<210> SEQ ID NO 21
<211> LENGTH: 23
<212> TYPE: RNA
<213> ORGANISM: Artificial
<220> FEATURE:
<223> OTHER INFORMATION: siRNA

<400> SEQUENCE: 21
gcaagcugac ccugaaguuc auu                                            23

<210> SEQ ID NO 22
<211> LENGTH: 23
<212> TYPE: RNA
<213> ORGANISM: Artificial
<220> FEATURE:
<223> OTHER INFORMATION: siRNA

<400> SEQUENCE: 22
cagaugaacu ucagggucag cuu                                            23

<210> SEQ ID NO 23
<211> LENGTH: 23
<212> TYPE: RNA
<213> ORGANISM: Artificial
<220> FEATURE:
<223> OTHER INFORMATION: siRNA

<400> SEQUENCE: 23
gcugacccug aaguucaucu guu                                            23

<210> SEQ ID NO 24
<211> LENGTH: 22
<212> TYPE: RNA
<213> ORGANISM: Artificial
<220> FEATURE:
<223> OTHER INFORMATION: siRNA
```

```
<400> SEQUENCE: 24
cagugaacuu cagggucagc uu                                       22

<210> SEQ ID NO 25
<211> LENGTH: 24
<212> TYPE: RNA
<213> ORGANISM: Artificial
<220> FEATURE:
<223> OTHER INFORMATION: siRNA

<400> SEQUENCE: 25
gcaagcugac ccugaaguuc auuu                                     24

<210> SEQ ID NO 26
<211> LENGTH: 24
<212> TYPE: RNA
<213> ORGANISM: Artificial
<220> FEATURE:
<223> OTHER INFORMATION: siRNA

<400> SEQUENCE: 26
gcagaugaac uucaggguca gcuu                                     24

<210> SEQ ID NO 27
<211> LENGTH: 24
<212> TYPE: RNA
<213> ORGANISM: Artificial
<220> FEATURE:
<223> OTHER INFORMATION: siRNA

<400> SEQUENCE: 27
gcugacccug aaguucaucu gcuu                                     24

<210> SEQ ID NO 28
<211> LENGTH: 24
<212> TYPE: RNA
<213> ORGANISM: Artificial
<220> FEATURE:
<223> OTHER INFORMATION: siRNA

<400> SEQUENCE: 28
gcagaugaac uucaggguca gcuu                                     24

<210> SEQ ID NO 29
<211> LENGTH: 25
<212> TYPE: RNA
<213> ORGANISM: Artificial
<220> FEATURE:
<223> OTHER INFORMATION: siRNA

<400> SEQUENCE: 29
gcaagcugac ccugaaguuc aucuu                                    25

<210> SEQ ID NO 30
<211> LENGTH: 25
<212> TYPE: RNA
<213> ORGANISM: Artificial
<220> FEATURE:
<223> OTHER INFORMATION: siRNA

<400> SEQUENCE: 30
ugcagaugaa cuucaggguc agcuu                                    25

<210> SEQ ID NO 31
<211> LENGTH: 25
```

```
<212> TYPE: RNA
<213> ORGANISM: Artificial
<220> FEATURE:
<223> OTHER INFORMATION: siRNA

<400> SEQUENCE: 31
gcugacccug aaguucaucu gcauu                                   25

<210> SEQ ID NO 32
<211> LENGTH: 25
<212> TYPE: RNA
<213> ORGANISM: Artificial
<220> FEATURE:
<223> OTHER INFORMATION: siRNA

<400> SEQUENCE: 32
ugcagaugaa cuucaggguc agcuu                                   25

<210> SEQ ID NO 33
<211> LENGTH: 26
<212> TYPE: RNA
<213> ORGANISM: Artificial
<220> FEATURE:
<223> OTHER INFORMATION: siRNA

<400> SEQUENCE: 33
aagcugaccc ugaaguucau cugcac                                  26

<210> SEQ ID NO 34
<211> LENGTH: 26
<212> TYPE: RNA
<213> ORGANISM: Artificial
<220> FEATURE:
<223> OTHER INFORMATION: siRNA

<400> SEQUENCE: 34
gugcagauga acuucagggu cagcuu                                  26

<210> SEQ ID NO 35
<211> LENGTH: 26
<212> TYPE: RNA
<213> ORGANISM: Artificial
<220> FEATURE:
<223> OTHER INFORMATION: siRNA

<400> SEQUENCE: 35
aagcugaccc ugaaguucau cugcuu                                  26

<210> SEQ ID NO 36
<211> LENGTH: 26
<212> TYPE: RNA
<213> ORGANISM: Artificial
<220> FEATURE:
<223> OTHER INFORMATION: siRNA

<400> SEQUENCE: 36
gugcagauga acuucagggu cagcuu                                  26

<210> SEQ ID NO 37
<211> LENGTH: 26
<212> TYPE: RNA
<213> ORGANISM: Artificial
<220> FEATURE:
<223> OTHER INFORMATION: siRNA

<400> SEQUENCE: 37
```
gcaagcugac ccugaaguuc aucuuu                      26

<210> SEQ ID NO 38
<211> LENGTH: 26
<212> TYPE: RNA
<213> ORGANISM: Artificial
<220> FEATURE:
<223> OTHER INFORMATION: siRNA

<400> SEQUENCE: 38
gugcagauga acuucagggu cagcuu                      26

<210> SEQ ID NO 39
<211> LENGTH: 26
<212> TYPE: RNA
<213> ORGANISM: Artificial
<220> FEATURE:
<223> OTHER INFORMATION: siRNA

<400> SEQUENCE: 39
gcugacccug aaguucaucu gcacuu                      26

<210> SEQ ID NO 40
<211> LENGTH: 26
<212> TYPE: RNA
<213> ORGANISM: Artificial
<220> FEATURE:
<223> OTHER INFORMATION: siRNA

<400> SEQUENCE: 40
gugcagauga acuucagggu cagcuu                      26

<210> SEQ ID NO 41
<211> LENGTH: 27
<212> TYPE: RNA
<213> ORGANISM: Artificial
<220> FEATURE:
<223> OTHER INFORMATION: siRNA

<400> SEQUENCE: 41
aagcugaccc ugaaguucau cugcacc                     27

<210> SEQ ID NO 42
<211> LENGTH: 27
<212> TYPE: RNA
<213> ORGANISM: Artificial
<220> FEATURE:
<223> OTHER INFORMATION: siRNA

<400> SEQUENCE: 42
ggugcagaug aacuucaggg ucagcuu                     27

<210> SEQ ID NO 43
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_feature
<222> LOCATION: (1)..(1)
<223> OTHER INFORMATION: conjugated to 6-FAM

<400> SEQUENCE: 43
aagcugaccc ugaaguucau cugcacc                     27

```
<210> SEQ ID NO 44
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_feature
<222> LOCATION: (1)..(1)
<223> OTHER INFORMATION: conjugated to 6-FAM

<400> SEQUENCE: 44
ggugcagaug aacuucaggg ucagcuu                                          27

<210> SEQ ID NO 45
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_feature
<222> LOCATION: (27)..(27)
<223> OTHER INFORMATION: conjugated to 6-FAM

<400> SEQUENCE: 45
aagcugaccc ugaaguucau cugcacc                                          27

<210> SEQ ID NO 46
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_feature
<222> LOCATION: (27)..(27)
<223> OTHER INFORMATION: conjugated to 6-FAM

<400> SEQUENCE: 46
ggugcagaug aacuucaggg ucagcuu                                          27

<210> SEQ ID NO 47
<211> LENGTH: 27
<212> TYPE: RNA
<213> ORGANISM: Artificial
<220> FEATURE:
<223> OTHER INFORMATION: siRNA

<400> SEQUENCE: 47
aagcugaccc ugaaguucau cugcauu                                          27

<210> SEQ ID NO 48
<211> LENGTH: 27
<212> TYPE: RNA
<213> ORGANISM: Artificial
<220> FEATURE:
<223> OTHER INFORMATION: siRNA

<400> SEQUENCE: 48
ggugcagaug aacuucaggg ucagcuu                                          27

<210> SEQ ID NO 49
<211> LENGTH: 27
<212> TYPE: RNA
<213> ORGANISM: Artificial
<220> FEATURE:
<223> OTHER INFORMATION: siRNA
```

```
<400> SEQUENCE: 49
gcaagcugac ccugaaguuc aucuguu                                            27

<210> SEQ ID NO 50
<211> LENGTH: 27
<212> TYPE: RNA
<213> ORGANISM: Artificial
<220> FEATURE:
<223> OTHER INFORMATION: siRNA

<400> SEQUENCE: 50
ggugcagaug aacuucaggg ucagcuu                                            27

<210> SEQ ID NO 51
<211> LENGTH: 27
<212> TYPE: RNA
<213> ORGANISM: Artificial
<220> FEATURE:
<223> OTHER INFORMATION: siRNA

<400> SEQUENCE: 51
gcugacccug aaguucaucu gcacauu                                            27

<210> SEQ ID NO 52
<211> LENGTH: 27
<212> TYPE: RNA
<213> ORGANISM: Artificial
<220> FEATURE:
<223> OTHER INFORMATION: siRNA

<400> SEQUENCE: 52
ggugcagaug aacuucaggg ucagcuu                                            27

<210> SEQ ID NO 53
<211> LENGTH: 27
<212> TYPE: RNA
<213> ORGANISM: Artificial
<220> FEATURE:
<223> OTHER INFORMATION: siRNA

<400> SEQUENCE: 53
aagcugaccc ugaagaucau cugcauu                                            27

<210> SEQ ID NO 54
<211> LENGTH: 27
<212> TYPE: RNA
<213> ORGANISM: Artificial
<220> FEATURE:
<223> OTHER INFORMATION: siRNA

<400> SEQUENCE: 54
ggugcagaug aucuucaggg ucagcuu                                            27

<210> SEQ ID NO 55
<211> LENGTH: 27
<212> TYPE: RNA
<213> ORGANISM: Artificial
<220> FEATURE:
<223> OTHER INFORMATION: siRNA

<400> SEQUENCE: 55
aagcugaccc ugaagaacau cugcauu                                            27

<210> SEQ ID NO 56
<211> LENGTH: 27
```

```
<212> TYPE: RNA
<213> ORGANISM: Artificial
<220> FEATURE:
<223> OTHER INFORMATION: siRNA

<400> SEQUENCE: 56
ggugcagaug uucuucaggg ucagcuu                                            27

<210> SEQ ID NO 57
<211> LENGTH: 27
<212> TYPE: RNA
<213> ORGANISM: Artificial
<220> FEATURE:
<223> OTHER INFORMATION: siRNA

<400> SEQUENCE: 57
aagcugaccc ugaacaacau cugcauu                                            27

<210> SEQ ID NO 58
<211> LENGTH: 27
<212> TYPE: RNA
<213> ORGANISM: Artificial
<220> FEATURE:
<223> OTHER INFORMATION: siRNA

<400> SEQUENCE: 58
ggugcagaug uuguucaggg ucagcuu                                            27

<210> SEQ ID NO 59
<211> LENGTH: 27
<212> TYPE: RNA
<213> ORGANISM: Artificial
<220> FEATURE:
<223> OTHER INFORMATION: siRNA

<400> SEQUENCE: 59
aagcugaccc uguucaucau cugcacc                                            27

<210> SEQ ID NO 60
<211> LENGTH: 27
<212> TYPE: RNA
<213> ORGANISM: Artificial
<220> FEATURE:
<223> OTHER INFORMATION: siRNA

<400> SEQUENCE: 60
ggugcagaug augaacaggg ucagcuu                                            27

<210> SEQ ID NO 61
<211> LENGTH: 28
<212> TYPE: RNA
<213> ORGANISM: Artificial
<220> FEATURE:
<223> OTHER INFORMATION: siRNA

<400> SEQUENCE: 61
aagcugaccc ugaaguucau cugcacca                                           28

<210> SEQ ID NO 62
<211> LENGTH: 28
<212> TYPE: RNA
<213> ORGANISM: Artificial
<220> FEATURE:
<223> OTHER INFORMATION: siRNA

<400> SEQUENCE: 62
```
uggugcagau gaacuucagg gucagcuu                                28

<210> SEQ ID NO 63
<211> LENGTH: 29
<212> TYPE: RNA
<213> ORGANISM: Artificial
<220> FEATURE:
<223> OTHER INFORMATION: siRNA

<400> SEQUENCE: 63
aagcugaccc ugaaguucau cugcaccac                               29

<210> SEQ ID NO 64
<211> LENGTH: 29
<212> TYPE: RNA
<213> ORGANISM: Artificial
<220> FEATURE:
<223> OTHER INFORMATION: siRNA

<400> SEQUENCE: 64
guggugcaga ugaacuucag ggucagcuu                               29

<210> SEQ ID NO 65
<211> LENGTH: 30
<212> TYPE: RNA
<213> ORGANISM: Artificial
<220> FEATURE:
<223> OTHER INFORMATION: siRNA

<400> SEQUENCE: 65
aagcugaccc ugaaguucau cugcaccacc                              30

<210> SEQ ID NO 66
<211> LENGTH: 30
<212> TYPE: RNA
<213> ORGANISM: Artificial
<220> FEATURE:
<223> OTHER INFORMATION: siRNA

<400> SEQUENCE: 66
gguggugcag augaacuuca gggucagcuu                              30

<210> SEQ ID NO 67
<211> LENGTH: 35
<212> TYPE: RNA
<213> ORGANISM: Artificial
<220> FEATURE:
<223> OTHER INFORMATION: siRNA

<400> SEQUENCE: 67
aagcugaccc ugaaguucau cugcaccacc ggcaa                        35

<210> SEQ ID NO 68
<211> LENGTH: 35
<212> TYPE: RNA
<213> ORGANISM: Artificial
<220> FEATURE:
<223> OTHER INFORMATION: siRNA

<400> SEQUENCE: 68
uugccggugg ugcagaugaa cuucaggguc agcuu                        35

<210> SEQ ID NO 69
<211> LENGTH: 40
<212> TYPE: RNA
<213> ORGANISM: Artificial

```
<220> FEATURE:
<223> OTHER INFORMATION: siRNA

<400> SEQUENCE: 69
aagcugaccc ugaaguucau cugcaccacc ggcaagcugc                          40

<210> SEQ ID NO 70
<211> LENGTH: 40
<212> TYPE: RNA
<213> ORGANISM: Artificial
<220> FEATURE:
<223> OTHER INFORMATION: siRNA

<400> SEQUENCE: 70
gcagcuugcc gguggugcag augaacuuca gggucagcuu                          40

<210> SEQ ID NO 71
<211> LENGTH: 45
<212> TYPE: RNA
<213> ORGANISM: Artificial
<220> FEATURE:
<223> OTHER INFORMATION: siRNA

<400> SEQUENCE: 71
aagcugaccc ugaaguucau cugcaccacc ggcaagcugc ccgug                    45

<210> SEQ ID NO 72
<211> LENGTH: 44
<212> TYPE: RNA
<213> ORGANISM: Artificial
<220> FEATURE:
<223> OTHER INFORMATION: siRNA

<400> SEQUENCE: 72
cacgggcagc uugccguggu gcagaugaac uucaggguca gcuu                     44

<210> SEQ ID NO 73
<211> LENGTH: 21
<212> TYPE: DNA
<213> ORGANISM: Artificial
<220> FEATURE:
<223> OTHER INFORMATION: probe

<400> SEQUENCE: 73
accctgaagt tcatctgcac c                                              21

<210> SEQ ID NO 74
<211> LENGTH: 32
<212> TYPE: RNA
<213> ORGANISM: Artificial
<220> FEATURE:
<223> OTHER INFORMATION: mRNA from EGFP from cloning vector pEGFP-C1

<400> SEQUENCE: 74
ugaagcagca cgacuucuuc aaguccgcca ug                                  32

<210> SEQ ID NO 75
<211> LENGTH: 34
<212> TYPE: RNA
<213> ORGANISM: Artificial
<220> FEATURE:
<223> OTHER INFORMATION: mRNA from EGFP from cloning vector pEGFP-C1

<400> SEQUENCE: 75
ugaaguucga gggcgacacc cuggugaacc gcau                                34
```

```
<210> SEQ ID NO 76
<211> LENGTH: 21
<212> TYPE: RNA
<213> ORGANISM: Artificial
<220> FEATURE:
<223> OTHER INFORMATION: siRNA

<400> SEQUENCE: 76
gcagcacgac uucuucaagu u                                              21

<210> SEQ ID NO 77
<211> LENGTH: 21
<212> TYPE: RNA
<213> ORGANISM: Artificial
<220> FEATURE:
<223> OTHER INFORMATION: siRNA

<400> SEQUENCE: 77
cuugaagaag ucgugcugcu u                                              21

<210> SEQ ID NO 78
<211> LENGTH: 27
<212> TYPE: RNA
<213> ORGANISM: Artificial
<220> FEATURE:
<223> OTHER INFORMATION: siRNA

<400> SEQUENCE: 78
aagcagcacg acuucuucaa guccgcc                                        27

<210> SEQ ID NO 79
<211> LENGTH: 27
<212> TYPE: RNA
<213> ORGANISM: Artificial
<220> FEATURE:
<223> OTHER INFORMATION: siRNA

<400> SEQUENCE: 79
ggcggacuug aagaagucgu gcugcuu                                        27

<210> SEQ ID NO 80
<211> LENGTH: 21
<212> TYPE: RNA
<213> ORGANISM: Artificial
<220> FEATURE:
<223> OTHER INFORMATION: siRNA

<400> SEQUENCE: 80
guucgagggc gacacccugu u                                              21

<210> SEQ ID NO 81
<211> LENGTH: 21
<212> TYPE: RNA
<213> ORGANISM: Artificial
<220> FEATURE:
<223> OTHER INFORMATION: siRNA

<400> SEQUENCE: 81
cagggucucg cccucgaacu u                                              21

<210> SEQ ID NO 82
<211> LENGTH: 27
<212> TYPE: RNA
<213> ORGANISM: Artificial
<220> FEATURE:
<223> OTHER INFORMATION: siRNA
```

<400> SEQUENCE: 82
guucgagggc gacacccugg ugaacuu                                              27

<210> SEQ ID NO 83
<211> LENGTH: 29
<212> TYPE: RNA
<213> ORGANISM: Artificial
<220> FEATURE:
<223> OTHER INFORMATION: siRNA

<400> SEQUENCE: 83
cgguucacca gggucucgcc cucgaacuu                                            29

<210> SEQ ID NO 84
<211> LENGTH: 27
<212> TYPE: DNA
<213> ORGANISM: Artificial
<220> FEATURE:
<223> OTHER INFORMATION: probe

<400> SEQUENCE: 84
ccaaaggtac ccagccttca tccagtt                                              27

<210> SEQ ID NO 85
<211> LENGTH: 30
<212> TYPE: DNA
<213> ORGANISM: Artificial
<220> FEATURE:
<223> OTHER INFORMATION: probe

<400> SEQUENCE: 85
gtgaggatgc ctctcttgct ctgggcctcg                                           30

<210> SEQ ID NO 86
<211> LENGTH: 2201
<212> TYPE: DNA
<213> ORGANISM: Homo sapiens

<400> SEQUENCE: 86
tttttttttt cgtcttagcc acgcagaagt cgcgtgtcta gtttgtttcg acgccggacc          60
gcgtaagaga cgatgatgtt gggcacggaa ggtggagagg gattcgtggt gaaggtccgg         120
ggcttgccct ggtcttgctc ggccgatgaa gtgcagaggt ttttttctga ctgcaaaatt         180
caaaatgggg ctcaaggtat tcgtttcatc tacaccagag aaggcagacc aagtggcgag         240
gcttttgttg aacttgaatc agaagatgaa gtcaaattgg ccctgaaaaa agacagagaa         300
actatgggac acagatatgt tgaagtattc aagtcaaaca cgttgaaat ggattgggtg          360 ttgaagcata ctggtccaaa tagtcctgac acggccaatg atggctttgt acggcttaga         420
ggacttccct ttggatgtag caaggaagaa attgttcagt tcttctcagg gttggaaatc         480
gtgccaaatg gataacatt gccggtggac ttccaggga ggagtacggg ggaggccttc           540
gtgcagtttg cttcacagga aatagctgaa aaggctctaa agaaacacaa ggaaagaata         600
gggcacaggt atattgaaat ctttaagagc agtagagctg aagttagaac tcattatgat         660
ccaccacgaa agcttatggc catgcagcgg ccaggtcctt atgacagacc tggggctggt         720
agagggtata acagcattgg cagaggagct ggctttgaga ggatgaggcg tggtgcttat         780
ggtggaggct atgaggccta tgatgattac aatggctata atgatggcta tggatttggg         840
tcagatagat ttggaagaga cctcaattac tgttttttcag gaatgtctga tcacagatac         900

| | | | |
|---|---|---|---|
| ggggatggtg gctctacttt ccagagcaca acaggacact gtgtacacat gcggggatta | 960 |
| ccttacagag ctactgagaa tgacatttat aattttttt caccgctcaa ccctgtgaga | 1020 |
| gtacacattg aaattggtcc tgatggcaga gtaactggtg aagcagatgt cgagttcgca | 1080 |
| actcatgaag atgctgtggc agctatgtca aagacaaag caaatatgca acacagatat | 1140 |
| gtagaactct tcttgaattc tacagcagga gcaagcggtg gtgcttacga acacagatat | 1200 |
| gtagaactct tcttgaattc tacagcagga gcaagcggtg gtgcttatgg tagccaaatg | 1260 |
| atgggaggca tgggcttgtc aaaccagtcc agctacgggg gcccagccag ccagcagctg | 1320 |
| agtgggggtt acgaggcgg ctacggtggc cagagcagca tgagtggata cgaccaagtt | 1380 |
| ttacaggaaa actccagtga ttttcaatca acattgcat aggtaaccaa ggagcagtga | 1440 |
| acagcagcta ctacagtagt ggaagccgtg catctatggg cgtgaacgga atgggagggt | 1500 |
| tgtctagcat gtccagtatg agtggtggat ggggaatgta attgatcgat cctgatcact | 1560 |
| gactcttggt caacctttt tttttttttt ttttctttaa gaaaacttca gtttaacagt | 1620 |
| ttctgcaata caagcttgtg atttatgctt actctaagtg gaaatcagga ttgttatgaa | 1680 |
| gacttaaggc ccagtatttt tgaatacaat actcatctag gatgtaacag tgaagctgag | 1740 |
| taaactataa ctgttaaact taagttccag cttttctcaa gttagttata ggatgtactt | 1800 |
| aagcagtaag cgtatttagg taaaagcagt tgaattatgt taaatgttgc cctttgccac | 1860 |
| gttaaattga acactgtttt ggatgcatgt tgaaagacat gcttttattt tttttgtaaa | 1920 |
| acaatatagg agctgtgtct actattaaaa gtgaaacatt ttggcatgtt tgttaattct | 1980 |
| agtttcattt aataacctgt aaggcacgta agtttaagct tttttttttt ttaagttaat | 2040 |
| gggaaaaatt tgagacgcaa taccaatact taggattttg gtcttggtgt ttgtatgaaa | 2100 |
| ttctgaggcc ttgatttaaa tctttcattg tattgtgatt tccttttagg tatattgcgc | 2160 |
| taagtgaaac ttgtcaaata aatcctcctt ttaaaaactg c | 2201 |

<210> SEQ ID NO 87
<211> LENGTH: 1620
<212> TYPE: DNA
<213> ORGANISM: Homo sapiens

<400> SEQUENCE: 87

| | | |
|---|---|---|
| ccggcggcgc tgggaggtgg agtcgttgct gttgctgttt gtgagcctgt ggcgcggctt | 60 |
| ctgtgggccg gaaccttaaa gatagccgta atggctgaaa atggtgataa tgaaaagatg | 120 |
| gctgccctgg aggccaaaat ctgtcatcaa attgagtatt attttggcga cttcaatttg | 180 |
| ccacgggaca gtttctaaa ggaacagata aaactggatg aaggctgggt acctttggag | 240 |
| ataatgataa aattcaacag gttgaaccgt ctaacaacag actttaatgt aattgtggaa | 300 |
| gcattgagca atccaaggc agaactcatg gaaatcagtg aagataaaac taaaatcaga | 360 |
| aggtctccaa gcaaaccct acctgaagtg actgatgagt ataaaaatga tgtaaaaaac | 420 |
| agatctgttt atattaaagg cttcccaact gatgcaactc ttgatgacat aaaagaatgg | 480 |
| ttagaagata aggtcaagt actaaatatt cagatgagaa gaacattgca taaagcattt | 540 |
| aagggatcaa tttttgttgt gtttgatagc attgaatctg ctaagaaatt tgtagagacc | 600 |
| cctggccaga agtacaaaga aacagacctg ctaatacttt tcaaggacga ttactttgcc | 660 |
| aaaaaaatg aagaagaaa acaaataaa gtggaagcta aattaagagc taaacaggag | 720 |
| caagaagcaa aacaaaagtt agaagaagat gctgaaatga aatctctaga agaaaagatt | 780 |
| ggatgcttgc tgaaattttc gggtgattta gatgatcaga cctgtagaga agatttacac | 840 |

```
atactttct caaatcatgg tgaaataaaa tggatagact tcgtcagagg agcaaaagag    900
gggataattc tatttaaaga aaaagccaag gaagcattgg gtaaagccaa agatgcaaat    960
aatggtaacc tacaattaag gaacaaagaa gtgacttggg aagtactaga aggagaggtg   1020 gaaaagaag cactgaagaa aataatagaa gaccaacaag aatccctaaa caaatggaag   1080
tcaaaaggtc gtagatttaa aggaaaagga aagggtaata aagctgccca gcctgggtct   1140
ggtaaaggaa aagtacagtt tcagggcaag aaaacgaaat ttgctagtga tgatgaacat   1200
gatgaacatg atgaaaatgg tgcaactgga cctgtgaaaa gagcaagaga agaaacagac   1260
aaagaagaac ctgcatccaa acaacagaaa acagaaaatg gtgctggaga ccagtagttt   1320
agtaaaccaa ttttttattc attttaaata ggttttaaac gacttttgtt tgcgggctt   1380 ttaaaaggaa aaccgaatta ggtccacttc aatgtccacc tgtgagaaag gaaaaatttt   1440
tttgttgttt aacttgtctt tttgttatgc aaatgagatt tctttgaatg tattgttctg   1500
tttgtgttat ttcagatgat tcaaatatca aaaggaagat tcttccatta aattgccttt   1560
gtaatatgag aatgtattag tacaaactaa ctaataaaat atatactata tgaaaagagc   1620
```

<210> SEQ ID NO 88  
<211> LENGTH: 35  
<212> TYPE: RNA  
<213> ORGANISM: Homo sapiens
<400> SEQUENCE: 88
guugaacuug aaucagaaga ugaagucaaa uuggc                                 35

<210> SEQ ID NO 89  
<211> LENGTH: 21  
<212> TYPE: RNA  
<213> ORGANISM: Artificial  
<220> FEATURE:  
<223> OTHER INFORMATION: siRNA
<400> SEQUENCE: 89
cuugaaucag aagaugaagu u                                                21

<210> SEQ ID NO 90  
<211> LENGTH: 21  
<212> TYPE: RNA  
<213> ORGANISM: Artificial  
<220> FEATURE:  
<223> OTHER INFORMATION: siRNA
<400> SEQUENCE: 90
cuucaucuuc ugauucaagu u                                                21

<210> SEQ ID NO 91  
<211> LENGTH: 27  
<212> TYPE: RNA  
<213> ORGANISM: Artificial  
<220> FEATURE:  
<223> OTHER INFORMATION: siRNA
<400> SEQUENCE: 91
aacuugaauc agaagaugaa gucaaau                                          27

<210> SEQ ID NO 92  
<211> LENGTH: 27  
<212> TYPE: RNA  
<213> ORGANISM: Artificial  
<220> FEATURE:

```
<223> OTHER INFORMATION: siRNA

<400> SEQUENCE: 92
auuugacuuc aucuucugau ucaaguu                                        27

<210> SEQ ID NO 93
<211> LENGTH: 35
<212> TYPE: RNA
<213> ORGANISM: Homo sapiens

<400> SEQUENCE: 93
auaaaacugg augaaggcug gguaccuuug gagau                               35

<210> SEQ ID NO 94
<211> LENGTH: 21
<212> TYPE: RNA
<213> ORGANISM: Artificial
<220> FEATURE:
<223> OTHER INFORMATION: siRNA

<400> SEQUENCE: 94
cuggaugaag gcugggacu u                                               21

<210> SEQ ID NO 95
<211> LENGTH: 21
<212> TYPE: RNA
<213> ORGANISM: Artificial
<220> FEATURE:
<223> OTHER INFORMATION: siRNA

<400> SEQUENCE: 95
guacccagcc uucauccagu u                                              21

<210> SEQ ID NO 96
<211> LENGTH: 27
<212> TYPE: RNA
<213> ORGANISM: Artificial
<220> FEATURE:
<223> OTHER INFORMATION: siRNA

<400> SEQUENCE: 96
aacuggauga aggcugggua ccuuuuu                                        27

<210> SEQ ID NO 97
<211> LENGTH: 27
<212> TYPE: RNA
<213> ORGANISM: Artificial
<220> FEATURE:
<223> OTHER INFORMATION: siRNA

<400> SEQUENCE: 97
ccaaagguac ccagccuuca uccaguu                                        27

<210> SEQ ID NO 98
<211> LENGTH: 22
<212> TYPE: RNA
<213> ORGANISM: Artificial
<220> FEATURE:
<223> OTHER INFORMATION: siRNA

<400> SEQUENCE: 98
gacccugaag uucaucugca cc                                             22

<210> SEQ ID NO 99
<211> LENGTH: 22
```

```
<212> TYPE: RNA
<213> ORGANISM: Artificial
<220> FEATURE:
<223> OTHER INFORMATION: siRNA

<400> SEQUENCE: 99
ugcagaugaa cuucaggguc ag                                              22

<210> SEQ ID NO 100
<211> LENGTH: 22
<212> TYPE: RNA
<213> ORGANISM: Artificial
<220> FEATURE:
<223> OTHER INFORMATION: siRNA

<400> SEQUENCE: 100
cugacccuga aguucaucug ca                                              22

<210> SEQ ID NO 101
<211> LENGTH: 22
<212> TYPE: RNA
<213> ORGANISM: Artificial
<220> FEATURE:
<223> OTHER INFORMATION: siRNA

<400> SEQUENCE: 101
cagaugaacu ucaggucag cu                                               22

<210> SEQ ID NO 102
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: DNA bases (remainder RNA bases)

<400> SEQUENCE: 102
ugcagaugaa cuucaggguc agctt                                           25

<210> SEQ ID NO 103
<211> LENGTH: 27
<212> TYPE: RNA
<213> ORGANISM: Artificial
<220> FEATURE:
<223> OTHER INFORMATION: siRNA

<400> SEQUENCE: 103
ugacccugaa guucaucugc accaccg                                         27

<210> SEQ ID NO 104
<211> LENGTH: 27
<212> TYPE: RNA
<213> ORGANISM: Artificial
<220> FEATURE:
<223> OTHER INFORMATION: siRNA

<400> SEQUENCE: 104
cgguggugca gaugaacuuc aggguca                                         27

<210> SEQ ID NO 105
<211> LENGTH: 21
<212> TYPE: RNA
<213> ORGANISM: Artificial
<220> FEATURE:
```

<223> OTHER INFORMATION: siRNA

<400> SEQUENCE: 105
ugaaguucau cugcaccacc g          21

<210> SEQ ID NO 106
<211> LENGTH: 22
<212> TYPE: RNA
<213> ORGANISM: Artificial
<220> FEATURE:
<223> OTHER INFORMATION: siRNA

<400> SEQUENCE: 106
ccugaaguuc aucugcacca cc          22

<210> SEQ ID NO 107
<211> LENGTH: 22
<212> TYPE: RNA
<213> ORGANISM: Artificial
<220> FEATURE:
<223> OTHER INFORMATION: siRNA

<400> SEQUENCE: 107
uggugcagau gaacuucagg gu          22

<210> SEQ ID NO 108
<211> LENGTH: 24
<212> TYPE: RNA
<213> ORGANISM: Artificial
<220> FEATURE:
<223> OTHER INFORMATION: siRNA

<400> SEQUENCE: 108
acccugaagu ucaucugcac cacc          24

<210> SEQ ID NO 109
<211> LENGTH: 24
<212> TYPE: RNA
<213> ORGANISM: Artificial
<220> FEATURE:
<223> OTHER INFORMATION: siRNA

<400> SEQUENCE: 109
uggugcagau gaacuucagg guca          24

<210> SEQ ID NO 110
<211> LENGTH: 22
<212> TYPE: RNA
<213> ORGANISM: Artificial
<220> FEATURE:
<223> OTHER INFORMATION: siRNA

<400> SEQUENCE: 110
gugcagauga acuucagggu ca          22

<210> SEQ ID NO 111
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: DNA bases (remainder are RNA bases)

<400> SEQUENCE: 111

-continued

```
acccugaagu ucaucugcac caccg                                            25

<210> SEQ ID NO 112
<211> LENGTH: 27
<212> TYPE: RNA
<213> ORGANISM: Artificial
<220> FEATURE:
<223> OTHER INFORMATION: siRNA

<400> SEQUENCE: 112
cgguggugca gaugaacuuc aggguca                                          27

<210> SEQ ID NO 113
<211> LENGTH: 27
<212> TYPE: RNA
<213> ORGANISM: Artificial
<220> FEATURE:
<223> OTHER INFORMATION: siRNA

<400> SEQUENCE: 113
caugaagcag cacgacuucu ucaaguc                                          27

<210> SEQ ID NO 114
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: DNA bases (remainder are RNA bases)

<400> SEQUENCE: 114
cuugaagaag ucgugcugcu ucatg                                            25

<210> SEQ ID NO 115
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: DNA bases (remainder are RNA bases)

<400> SEQUENCE: 115
gcagcacgac uucuucaagu ccgcc                                            25

<210> SEQ ID NO 116
<211> LENGTH: 48
<212> TYPE: DNA
<213> ORGANISM: Artificial
<220> FEATURE:
<223> OTHER INFORMATION: EGFP from cloning vector pEGFP-C1

<400> SEQUENCE: 116
acggcaagct gaccctgaag ttcatctgca ccaccggcaa gctgcccg                   48

<210> SEQ ID NO 117
<211> LENGTH: 21
<212> TYPE: RNA
<213> ORGANISM: Artificial
<220> FEATURE:
<223> OTHER INFORMATION: siRNA
```

```
<400> SEQUENCE: 117
gcaccagagc caauggaacu u                                              21

<210> SEQ ID NO 118
<211> LENGTH: 21
<212> TYPE: RNA
<213> ORGANISM: Artificial
<220> FEATURE:
<223> OTHER INFORMATION: siRNA

<400> SEQUENCE: 118
guuccauugg cucuggugcu u                                              21

<210> SEQ ID NO 119
<211> LENGTH: 19
<212> TYPE: RNA
<213> ORGANISM: Artificial
<220> FEATURE:
<223> OTHER INFORMATION: siRNA

<400> SEQUENCE: 119
gcaccagagc caauggaac                                                 19

<210> SEQ ID NO 120
<211> LENGTH: 19
<212> TYPE: RNA
<213> ORGANISM: Artificial
<220> FEATURE:
<223> OTHER INFORMATION: siRNA

<400> SEQUENCE: 120
guuccauugg cucuggugc                                                 19

<210> SEQ ID NO 121
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 1, 3, 5, 7, 9, 11, 13, 17, 19 are 2' OMe
      derivatives

<400> SEQUENCE: 121
gcaccagagc caauggaac                                                 19

<210> SEQ ID NO 122
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 2, 4, 6, 8, 10, 12, 14, 16 and 18 are 2'
      OMe derivatives

<400> SEQUENCE: 122
guuccauugg cucuggugc                                                 19

<210> SEQ ID NO 123
<211> LENGTH: 19
<212> TYPE: RNA
<213> ORGANISM: Artificial
```

```
<220> FEATURE:
<223> OTHER INFORMATION: siRNA

<400> SEQUENCE: 123
gcaccagagc caauggaac                                                    19

<210> SEQ ID NO 124
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 2, 4, 6, 8, 10, 12, 14, 16 and 18 are 2'
      OMe derivatives

<400> SEQUENCE: 124
guuccauugg cucggugc                                                     19

<210> SEQ ID NO 125
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 1, 3, 5, 7, 9, 11, 13, 17, 19 are 2' OMe
      derivatives

<400> SEQUENCE: 125
gcaccagagc caauggaac                                                    19

<210> SEQ ID NO 126
<211> LENGTH: 19
<212> TYPE: RNA
<213> ORGANISM: Artificial
<220> FEATURE:
<223> OTHER INFORMATION: siRNA

<400> SEQUENCE: 126
guuccauugg cucggugc                                                     19

<210> SEQ ID NO 127
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 1, 3, 5, 7, 9, 11, 13, 17, 19 are 2' OMe
      derivatives

<400> SEQUENCE: 127
gcaccagagc caauggaac                                                    19

<210> SEQ ID NO 128
<211> LENGTH: 21
<212> TYPE: RNA
<213> ORGANISM: Artificial
<220> FEATURE:
<223> OTHER INFORMATION: siRNA

<400> SEQUENCE: 128
```

-continued

```
guuccauugg cucuggugcu u                                              21

<210> SEQ ID NO 129
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 2, 4, 6, 8, 10, 12, 14, 16 and 18 are 2'
      OMe derivatives

<400> SEQUENCE: 129
gcaccagagc caauggaac                                                 19

<210> SEQ ID NO 130
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 1, 3, 5, 7, 9, 11, 13, 17, 19 are 2' OMe
      derivatives

<400> SEQUENCE: 130
guuccauugg cucuggugc                                                 19

<210> SEQ ID NO 131
<211> LENGTH: 19
<212> TYPE: RNA
<213> ORGANISM: Artificial
<220> FEATURE:
<223> OTHER INFORMATION: siRNA

<400> SEQUENCE: 131
gcaccagagc caauggaac                                                 19

<210> SEQ ID NO 132
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 1, 3, 5, 7, 9, 11, 13, 17, 19 are 2' OMe
      derivatives

<400> SEQUENCE: 132
guuccauugg cucuggugc                                                 19

<210> SEQ ID NO 133
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 2, 4, 6, 8, 10, 12, 14, 16 and 18 are 2'
      OMe derivatives
```

```
<400> SEQUENCE: 133
gcaccagagc caauggaac                                                        19

<210> SEQ ID NO 134
<211> LENGTH: 19
<212> TYPE: RNA
<213> ORGANISM: Artificial
<220> FEATURE:
<223> OTHER INFORMATION: siRNA

<400> SEQUENCE: 134
guuccauugg cucuggugc                                                        19

<210> SEQ ID NO 135
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 2, 4, 6, 8, 10, 12, 14, 16 and 18 are 2'
      OMe derivatives

<400> SEQUENCE: 135
gcaccagagc caauggaac                                                        19

<210> SEQ ID NO 136
<211> LENGTH: 21
<212> TYPE: RNA
<213> ORGANISM: Artificial
<220> FEATURE:
<223> OTHER INFORMATION: siRNA

<400> SEQUENCE: 136
guuccauugg cucuggugcu u                                                     21

<210> SEQ ID NO 137
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 1, 3, 5, 7, 9, 11, 13, 17, 19 are 2' OMe
      derivatives

<400> SEQUENCE: 137
gcaccagagc caauggaac                                                        19

<210> SEQ ID NO 138
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 1, 3, 5, 7, 9, 11, 13, 17, 19 are 2' OMe
      derivatives

<400> SEQUENCE: 138
guuccauugg cucuggugc                                                        19
```

```
<210> SEQ ID NO 139
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 2, 4, 6, 8, 10, 12, 14, 16 and 18 are 2'
      OMe derivatives

<400> SEQUENCE: 139
gcaccagagc caauggaac                                                    19

<210> SEQ ID NO 140
<211> LENGTH: 19
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(19)
<223> OTHER INFORMATION: bases 2, 4, 6, 8, 10, 12, 14, 16 and 18 are 2'
      OMe derivatives

<400> SEQUENCE: 140
guuccauugg cucuggugc                                                    19

<210> SEQ ID NO 141
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 3, 6-9, 12, 13 and 15-18 are 2' OMe
      derivatives

<400> SEQUENCE: 141
gcaccagagc caauggaacu u                                                 21

<210> SEQ ID NO 142
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives

<400> SEQUENCE: 142
guuccauugg cucuggugcu u                                                 21

<210> SEQ ID NO 143
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 3, 6-9, 12, 13 and 15-18 are 2' OMe
``` derivatives

<400> SEQUENCE: 143
gcaccagagc caauggaacu u                                              21

<210> SEQ ID NO 144
<211> LENGTH: 21
<212> TYPE: RNA
<213> ORGANISM: Artificial
<220> FEATURE:
<223> OTHER INFORMATION: siRNA

<400> SEQUENCE: 144
guuccauugg cucuggugcu u                                              21

<210> SEQ ID NO 145
<211> LENGTH: 21
<212> TYPE: RNA
<213> ORGANISM: Artificial
<220> FEATURE:
<223> OTHER INFORMATION: siRNA

<400> SEQUENCE: 145
gcaccagagc caauggaacu u                                              21

<210> SEQ ID NO 146
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives

<400> SEQUENCE: 146
guuccauugg cucuggugcu u                                              21

<210> SEQ ID NO 147
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2, 4, 5, 10, 11, 14, 19 and 20 are 2' F
      derivatives

<400> SEQUENCE: 147
gcaccagagc caauggaacu u                                              21

<210> SEQ ID NO 148
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2-5, 7, 8, 11-14, 17, 19 and 20 are 2' F
      derivatives

<400> SEQUENCE: 148

```
guuccauugg cucuggugcu u                                              21

<210> SEQ ID NO 149
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2, 4, 5, 10, 11, 14, 19 and 20 are 2' F
      derivatives

<400> SEQUENCE: 149
gcaccagagc caauggaacu u                                              21

<210> SEQ ID NO 150
<211> LENGTH: 21
<212> TYPE: RNA
<213> ORGANISM: Artificial
<220> FEATURE:
<223> OTHER INFORMATION: siRNA

<400> SEQUENCE: 150
guuccauugg cucuggugcu u                                              21

<210> SEQ ID NO 151
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2, 4, 5, 10, 11, 14, 19 and 20 are 2' F
      derivatives

<400> SEQUENCE: 151
gcaccagagc caauggaacu u                                              21

<210> SEQ ID NO 152
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives

<400> SEQUENCE: 152
guuccauugg cucuggugcu u                                              21

<210> SEQ ID NO 153
<211> LENGTH: 21
<212> TYPE: RNA
<213> ORGANISM: Artificial
<220> FEATURE:
<223> OTHER INFORMATION: siRNA

<400> SEQUENCE: 153
gcaccagagc caauggaacu u                                              21

<210> SEQ ID NO 154
```

```
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2-5, 7, 8, 11-14, 17, 19 and 20 are 2' F
      derivatives

<400> SEQUENCE: 154
guuccauugg cucuggugcu u                                              21

<210> SEQ ID NO 155
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 3, 6-9, 12, 13 and 15-18 are 2' OMe
      derivatives

<400> SEQUENCE: 155
gcaccagagc caauggaacu u                                              21

<210> SEQ ID NO 156
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2-5, 7, 8, 11-14, 17, 19 and 20 are 2' F
      derivatives

<400> SEQUENCE: 156
guuccauugg cucuggugcu u                                              21

<210> SEQ ID NO 157
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 3, 6-9 and 15-18 are 2' OMe
      derivatives and bases 2, 4, 5, 10, 11, 14, 19 and 20 are 2' F
      derivatives

<400> SEQUENCE: 157
gcaccagagc caauggaacu u                                              21

<210> SEQ ID NO 158
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives and bases 2-5, 7, 8, 11-14, 17, 19 and 20 are 2' F
``` derivatives

<400> SEQUENCE: 158
guuccauugg cucuggugcu u                                            21

<210> SEQ ID NO 159
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 3, 6-9 and 15-18 are 2' OMe
      derivatives and bases 2, 4, 5, 10, 11, 14, 19 and 20 are 2' F
      derivatives

<400> SEQUENCE: 159
gcaccagagc caauggaacu u                                            21

<210> SEQ ID NO 160
<211> LENGTH: 21
<212> TYPE: RNA
<213> ORGANISM: Artificial
<220> FEATURE:
<223> OTHER INFORMATION: siRNA

<400> SEQUENCE: 160
guuccauugg cucuggugcu u                                            21

<210> SEQ ID NO 161
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 3, 6-9 and 15-18 are 2' OMe
      derivatives and bases 2, 4, 5, 10, 11, 14, 19 and 20 are 2' F
      derivatives

<400> SEQUENCE: 161
gcaccagagc caauggaacu u                                            21

<210> SEQ ID NO 162
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives

<400> SEQUENCE: 162
guuccauugg cucuggugcu u                                            21

<210> SEQ ID NO 163
<211> LENGTH: 21
<212> TYPE: RNA
<213> ORGANISM: Artificial
<220> FEATURE:
<223> OTHER INFORMATION: siRNA
<220> FEATURE:

-continued

```
<221> NAME/KEY: misc_RNA
<222> LOCATION: (1)..(21)
<223> OTHER INFORMATION: bases 1, 3, 6-9 and 15-18 are 2' OMe
      derivatives and bases 2, 4, 5, 10, 11, 14, 19 and 20 are 2' F
      derivatives

<400> SEQUENCE: 163
gcaccagagc caauggaacu u                                            21

<210> SEQ ID NO 164
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2-5, 7, 8, 11-14, 17, 19 and 20 are 2' F
      derivatives

<400> SEQUENCE: 164
guuccauugg cucuggugcu u                                            21

<210> SEQ ID NO 165
<211> LENGTH: 21
<212> TYPE: RNA
<213> ORGANISM: Artificial
<220> FEATURE:
<223> OTHER INFORMATION: siRNA

<400> SEQUENCE: 165
gcaccagagc caauggaacu u                                            21

<210> SEQ ID NO 166
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives and bases 2-5, 7, 8, 11-14, 17, 19 and 20 are 2' F
      derivatives

<400> SEQUENCE: 166
guuccauugg cucuggugcu u                                            21

<210> SEQ ID NO 167
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 3, 6-9, 12, 13 and 15-18 are 2' OMe
      derivatives

<400> SEQUENCE: 167
gcaccagagc caauggaacu u                                            21

<210> SEQ ID NO 168
<211> LENGTH: 21
<212> TYPE: RNA
<213> ORGANISM: Artificial
```

```
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives and bases 2-5, 7, 8, 11-14, 17, 19 and 20 are 2' F
      derivatives

<400> SEQUENCE: 168
guuccauugg cucuggugcu u                                             21

<210> SEQ ID NO 169
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 2, 4, 5, 10, 11, 14, 19 and 20 are 2' F
      derivatives

<400> SEQUENCE: 169
gcaccagagc caauggaacu u                                             21

<210> SEQ ID NO 170
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 1, 6, 9, 10, 15, 16 and 18 are 2' OMe
      derivatives and bases
      2-5, 7, 8, 11-14, 17, 19 and 20 are 2' F derivatives

<400> SEQUENCE: 170
guuccauugg cucuggugcu u                                             21

<210> SEQ ID NO 171
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 171
gcaccagagc caauggaacu ugatg                                         25

<210> SEQ ID NO 172
<211> LENGTH: 27
<212> TYPE: RNA
<213> ORGANISM: Artificial
<220> FEATURE:
<223> OTHER INFORMATION: siRNa

<400> SEQUENCE: 172
caucaaguuc cauuggcucu ggugcuu                                       27

<210> SEQ ID NO 173
<211> LENGTH: 25
```

```
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 173
gcaccagagc caauggaacu ugatg                                              25

<210> SEQ ID NO 174
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (26)..(27)
<223> OTHER INFORMATION: bases 26 and 27 are 2' OMe derivatives

<400> SEQUENCE: 174
caucaaguuc cauuggcucu ggugcuu                                            27

<210> SEQ ID NO 175
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 6, 8, 10, 12, 14, 16 and 18 are 2'
      OMe derivatives
<220> FEATURE:
<221> NAME/KEY: misc_feature
<222> LOCATION: (24)..(25)
<223> OTHER INFORMATION: bases 24 and 25 are DNA

<400> SEQUENCE: 175
gcaccagagc caauggaacu ugatg                                              25

<210> SEQ ID NO 176
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 7, 9, 11, 13, 15, 17, 19, 21, 23 and 25
      are 2' OMe derivatives

<400> SEQUENCE: 176
caucaaguuc cauuggcucu ggugcuu                                            27

<210> SEQ ID NO 177
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 6, 8, 10, 12, 14, 16 and 18 are 2'
      OMe derivatives
```

```
<220> FEATURE:
<221> NAME/KEY: misc_feature
<222> LOCATION: (24)..(25)
<223> OTHER INFORMATION: bases 24 and 25 are DNA

<400> SEQUENCE: 177
gcaccagagc caauggaacu ugatg                                              25

<210> SEQ ID NO 178
<211> LENGTH: 27
<212> TYPE: RNA
<213> ORGANISM: Artificial
<220> FEATURE:
<223> OTHER INFORMATION: siRNA

<400> SEQUENCE: 178
caucaaguuc cauuggcucu ggugcuu                                            27

<210> SEQ ID NO 179
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 179
gcaccagagc caauggaacu ugatg                                              25

<210> SEQ ID NO 180
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 7, 9, 11, 13, 15, 17, 19, 21, 23 and 25
      are 2' OMe derivatives

<400> SEQUENCE: 180
caucaaguuc cauuggcucu ggugcuu                                            27

<210> SEQ ID NO 181
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 6, 8, 10, 12, 14, 16 and 18 are 2'
      OMe derivatives
<220> FEATURE:
<221> NAME/KEY: misc_feature
<222> LOCATION: (24)..(25)
<223> OTHER INFORMATION: bases 24 and 25 are DNA

<400> SEQUENCE: 181
gcaccagagc caauggaacu ugatg                                              25

<210> SEQ ID NO 182
<211> LENGTH: 27
<212> TYPE: RNA
```

-continued

```
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 9, 11, 13, 15, 17, 19, 21, 23 and 25 are
      2' OMe derivatives

<400> SEQUENCE: 182
caucaaguuc cauuggcucu ggugcuu                                          27

<210> SEQ ID NO 183
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 183
gcaccagagc caauggaacu ugatg                                            25

<210> SEQ ID NO 184
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 9, 11, 13, 15, 17, 19, 21, 23 and 25 are
      2' OMe derivatives

<400> SEQUENCE: 184
caucaaguuc cauuggcucu ggugcuu                                          27

<210> SEQ ID NO 185
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 1, 3, 6-9, 12, 13 and 15-18 are 2' OMe
      derivatives
<220> FEATURE:
<221> NAME/KEY: misc_feature
<222> LOCATION: (24)..(25)
<223> OTHER INFORMATION: bases 24 and 25 are DNA

<400> SEQUENCE: 185
gcaccagagc caauggaacu ugatg                                            25

<210> SEQ ID NO 186
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 12, 15, 16, 21, 22 and 24 are 2' OMe
      derivatives
```

<400> SEQUENCE: 186
caucaaguuc cauuggcucu ggugcuu         27

<210> SEQ ID NO 187
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 1, 3, 6-9, 12, 13 and 15-18 are 2' OMe
      derivatives
<220> FEATURE:
<221> NAME/KEY: misc_feature
<222> LOCATION: (24)..(25)
<223> OTHER INFORMATION: bases 24 and 25 are DNA

<400> SEQUENCE: 187
gcaccagagc caauggaacu ugatg           25

<210> SEQ ID NO 188
<211> LENGTH: 27
<212> TYPE: RNA
<213> ORGANISM: Artificial
<220> FEATURE:
<223> OTHER INFORMATION: siRNA

<400> SEQUENCE: 188
caucaaguuc cauuggcucu ggugcuu         27

<210> SEQ ID NO 189
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 189
gcaccagagc caauggaacu ugatg           25

<210> SEQ ID NO 190
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 12, 15, 16, 21, 22 and 24 are 2' OMe
      derivatives

<400> SEQUENCE: 190
caucaaguuc cauuggcucu ggugcuu         27

<210> SEQ ID NO 191
<211> LENGTH: 25
<212> TYPE: DNA
<213> ORGANISM: Artificial
<220> FEATURE:
<223> OTHER INFORMATION: siRNA
<220> FEATURE:

```
<221> NAME/KEY: misc_RNA
<222> LOCATION: (1)..(25)
<223> OTHER INFORMATION: bases 2, 4, 5, 10, 11, 14, 19 and 20 are 2' F
      derivatives
<220> FEATURE:
<221> NAME/KEY: misc_feature
<222> LOCATION: (24)..(25)
<223> OTHER INFORMATION: bases 24 and 25 are DNA

<400> SEQUENCE: 191
gcaccagagc caauggaacu ugatg                                          25

<210> SEQ ID NO 192
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 8-11, 13, 14, 17-20, 23, 25 and 26 are 2'
      F derivatives

<400> SEQUENCE: 192
caucaaguuc cauuggcucu ggugcuu                                        27

<210> SEQ ID NO 193
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 5, 10, 11, 14, 19 and 20 are 2' F
      derivatives
<220> FEATURE:
<221> NAME/KEY: misc_feature
<222> LOCATION: (24)..(25)
<223> OTHER INFORMATION: bases 24 and 25 are DNA

<400> SEQUENCE: 193
gcaccagagc caauggaacu ugatg                                          25

<210> SEQ ID NO 194
<211> LENGTH: 27
<212> TYPE: RNA
<213> ORGANISM: Artificial
<220> FEATURE:
<223> OTHER INFORMATION: siRNA

<400> SEQUENCE: 194
caucaaguuc cauuggcucu ggugcuu                                        27

<210> SEQ ID NO 195
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 5, 10, 11, 14, 19 and 20 are 2' F
      derivatives
<220> FEATURE:
<221> NAME/KEY: misc_feature
<222> LOCATION: (24)..(25)
<223> OTHER INFORMATION: bases 24 and 25 are DNA
```

```
<400> SEQUENCE: 195
gcaccagagc caauggaacu ugatg                                              25

<210> SEQ ID NO 196
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 12, 15, 16, 21, 22 and 24 are 2' OMe
      derivatives

<400> SEQUENCE: 196
caucaaguuc cauuggcucu ggugcuu                                            27

<210> SEQ ID NO 197
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 197
gcaccagagc caauggaacu ugatg                                              25

<210> SEQ ID NO 198
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 8-11, 13, 14, 17-20, 23, 25 and 26 are 2'
      F derivatives

<400> SEQUENCE: 198
caucaaguuc cauuggcucu ggugcuu                                            27

<210> SEQ ID NO 199
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 1, 3, 6-9, 12, 13 and 15-18 are 2' OMe
      derivatives
<220> FEATURE:
<221> NAME/KEY: misc_feature
<222> LOCATION: (24)..(25)
<223> OTHER INFORMATION: bases 24 and 25 are DNA

<400> SEQUENCE: 199
gcaccagagc caauggaacu ugatg                                              25

<210> SEQ ID NO 200
<211> LENGTH: 27
```

```
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 8-11, 13, 14, 17-20, 23, 25 and 26 are 2'
      F derivatives

<400> SEQUENCE: 200
caucaaguuc cauuggcucu ggugcuu                                            27

<210> SEQ ID NO 201
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 201
gcaccagagc caauggaacu ugatg                                              25

<210> SEQ ID NO 202
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 12, 15, 16, 21, 22 and 24 are 2' OMe
      derivatives and bases 8-11, 13, 14, 17-20, 23, 25 and 26 are 2' F
      derivatives

<400> SEQUENCE: 202
caucaaguuc cauuggcucu ggugcuu                                            27

<210> SEQ ID NO 203
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 1, 3, 6-9, 12, 13 and 15-18 are 2' OMe
      derivatives
<220> FEATURE:
<221> NAME/KEY: misc_feature
<222> LOCATION: (24)..(25)
<223> OTHER INFORMATION: bases 24 and 25 are DNA

<400> SEQUENCE: 203
gcaccagagc caauggaacu ugatg                                              25

<210> SEQ ID NO 204
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
```

```
<223> OTHER INFORMATION: bases 12, 15, 16, 21, 22 and 24 are 2' OMe
      derivatives and bases
      8-11, 13, 14, 17-20, 23, 25 and 26 are 2' F derivatives

<400> SEQUENCE: 204
caucaaguuc cauuggcucu ggugcuu                                       27

<210> SEQ ID NO 205
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 5, 10, 11, 14, 19 and 20 are 2' F
      derivatives
<220> FEATURE:
<221> NAME/KEY: misc_feature
<222> LOCATION: (24)..(25)
<223> OTHER INFORMATION: bases 24 and 25 are DNA

<400> SEQUENCE: 205
gcaccagagc caauggaacu ugatg                                         25

<210> SEQ ID NO 206
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 12, 15, 16, 21, 22 and 24 are 2' OMe
      derivatives and bases 8-11, 13, 14, 17-20, 23, 25 and 26 are 2' F
      derivatives

<400> SEQUENCE: 206
caucaaguuc cauuggcucu ggugcuu                                       27

<210> SEQ ID NO 207
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 9, 11, 13, 15, 17, 19, 21, 23 and 25-27
      are 2' OMe derivatives

<400> SEQUENCE: 207
caucaaguuc cauuggcucu ggugcuu                                       27

<210> SEQ ID NO 208
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 208
acccugaagu ucaucugcac caccg                                         25
```

<210> SEQ ID NO 209
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 2, 11, 13, 15, 17, 19, 21, 23 and 25-27
      are 2' OMe derivatives

<400> SEQUENCE: 209
cgguggugca gaugaacuuc aggguca                                        27

<210> SEQ ID NO 210
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 6, 8, 10, 12, 14, 16 and 18 are 2'
      OMe derivatives
<220> FEATURE:
<221> NAME/KEY: misc_feature
<222> LOCATION: (24)..(25)
<223> OTHER INFORMATION: bases 24 and 25 are DNA

<400> SEQUENCE: 210
acccugaagu ucaucugcac caccg                                          25

<210> SEQ ID NO 211
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 9, 11, 13, 15, 17, 19, 21, 23 and 25-27
      are 2' OMe derivatives

<400> SEQUENCE: 211
cgguggugca gaugaacuuc aggguca                                        27

<210> SEQ ID NO 212
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 1, 2, 9, 11, 13, 15, 17, 19, 21, 23 and
      25-27 are 2' OMe derivatives

<400> SEQUENCE: 212
cgguggugca gaugaacuuc aggguca                                        27

<210> SEQ ID NO 213
<211> LENGTH: 27
<212> TYPE: RNA
<213> ORGANISM: Artificial
<220> FEATURE:

```
<223> OTHER INFORMATION: siRNA

<400> SEQUENCE: 213
cgguggugca gaugaacuuc agguca                                              27

<210> SEQ ID NO 214
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 214
gccagacuuu cuuggauuug aaatt                                               25

<210> SEQ ID NO 215
<211> LENGTH: 27
<212> TYPE: RNA
<213> ORGANISM: Artificial
<220> FEATURE:
<223> OTHER INFORMATION: siRNA

<400> SEQUENCE: 215
aauuucaaau ccaacaaagu cuggcuu                                             27

<210> SEQ ID NO 216
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_RNA
<222> LOCATION: (1)..(25)
<223> OTHER INFORMATION: bases 2, 4, 6, 8, 10, 12, 14, 16 and 18 are 2'
      OMe derivatives
<220> FEATURE:
<221> NAME/KEY: misc_feature
<222> LOCATION: (24)..(25)
<223> OTHER INFORMATION: bases 24 and 25 are DNA

<400> SEQUENCE: 216
gccagacuuu cuuggauuug aaatt                                               25

<210> SEQ ID NO 217
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 9, 11, 13, 15, 17, 19, 21, 23 and 25-27
      are 2' OMe derivatives

<400> SEQUENCE: 217
aauuucaaau ccaacaaagu cuggcuu                                             27

<210> SEQ ID NO 218
<211> LENGTH: 27
<212> TYPE: RNA
<213> ORGANISM: Artificial
<220> FEATURE:
<223> OTHER INFORMATION: siRNA
```

```
<220> FEATURE:
<221> NAME/KEY: misc_RNA
<222> LOCATION: (1)..(27)
<223> OTHER INFORMATION: bases 1, 2, 9, 11, 13, 15, 17, 19, 21, 23 and
      25-27 are 2' OMe derivatives

<400> SEQUENCE: 218
aauuucaaau ccaacaaagu cuggcuu                                              27

<210> SEQ ID NO 219
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 1, 3, 5, 7, 9, 11, 13, 15, 17, 19, 21, 23
      and 25-27 are 2' OMe derivatives

<400> SEQUENCE: 219
aauuucaaau ccaacaaagu cuggcuu                                              27

<210> SEQ ID NO 220
<211> LENGTH: 25
<212> TYPE: DNA
<213> ORGANISM: Artificial
<220> FEATURE:
<223> OTHER INFORMATION: siRNA
<220> FEATURE:
<221> NAME/KEY: misc_feature
<222> LOCATION: (24)..(25)
<223> OTHER INFORMATION: bases 24 and 25 are DNA

<400> SEQUENCE: 220
gccagacuuu guuggauuug agccg                                                25

<210> SEQ ID NO 221
<211> LENGTH: 27
<212> TYPE: RNA
<213> ORGANISM: Artificial
<220> FEATURE:
<223> OTHER INFORMATION: siRNA

<400> SEQUENCE: 221
cggcucaaau ccaacaaagu cuggcuu                                              27

<210> SEQ ID NO 222
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 1, 3, 5, 7, 9, 11, 13, 15, 17, 19, 21, 23
      and 25-27 are 2' OMe derivatives

<400> SEQUENCE: 222
cggcucaaau ccaacaaagu cuggcuu                                              27

<210> SEQ ID NO 223
<211> LENGTH: 25
<212> TYPE: DNA
<213> ORGANISM: Artificial
<220> FEATURE:
<223> OTHER INFORMATION: siRNA
```

```
<220> FEATURE:
<221> NAME/KEY: misc_feature
<222> LOCATION: (24)..(25)
<223> OTHER INFORMATION: bases 24 and 25 are DNA

<400> SEQUENCE: 223
cuuccucucu uucucuccu uguga                                              25

<210> SEQ ID NO 224
<211> LENGTH: 27
<212> TYPE: RNA
<213> ORGANISM: Artificial
<220> FEATURE:
<223> OTHER INFORMATION: siRNA

<400> SEQUENCE: 224
ucacaaggga gagaaagaga ggaagga                                           27

<210> SEQ ID NO 225
<211> LENGTH: 21
<212> TYPE: RNA
<213> ORGANISM: Artificial
<220> FEATURE:
<223> OTHER INFORMATION: siRNA

<400> SEQUENCE: 225
gccagacuuu guuggauuug a                                                 21

<210> SEQ ID NO 226
<211> LENGTH: 21
<212> TYPE: RNA
<213> ORGANISM: Artificial
<220> FEATURE:
<223> OTHER INFORMATION: siRNA

<400> SEQUENCE: 226
aaauccaaca aagucuggcu u                                                 21

<210> SEQ ID NO 227
<211> LENGTH: 21
<212> TYPE: RNA
<213> ORGANISM: Artificial
<220> FEATURE:
<223> OTHER INFORMATION: siRNA

<400> SEQUENCE: 227
gccagacuuu guuggauuug a                                                 21

<210> SEQ ID NO 228
<211> LENGTH: 21
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(21)
<223> OTHER INFORMATION: bases 3, 5, 7, 9, 11, 13, 15, 17 and 19-21 are
      2' OMe derivatives

<400> SEQUENCE: 228
aaauccaaca aagucuggcu u                                                 21

<210> SEQ ID NO 229
<211> LENGTH: 22
<212> TYPE: RNA
<213> ORGANISM: Artificial
```

```
<220> FEATURE:
<223> OTHER INFORMATION: siRNA

<400> SEQUENCE: 229
gccagacuuu guuggauuug aa                                            22

<210> SEQ ID NO 230
<211> LENGTH: 22
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(22)
<223> OTHER INFORMATION: bases 4, 6, 8, 10, 12, 14, 16, 18 and 20-22 are
      2' OMe
      derivatives

<400> SEQUENCE: 230
caaauccaac aaagucuggc uu                                            22

<210> SEQ ID NO 231
<211> LENGTH: 22
<212> TYPE: RNA
<213> ORGANISM: Artificial
<220> FEATURE:
<223> OTHER INFORMATION: siRNA

<400> SEQUENCE: 231
gccagacuuu guuggauuug aa                                            22

<210> SEQ ID NO 232
<211> LENGTH: 21
<212> TYPE: RNA
<213> ORGANISM: Artificial
<220> FEATURE:
<223> OTHER INFORMATION: siRNA

<400> SEQUENCE: 232
gccagacuuu guuggauuug a                                             21

<210> SEQ ID NO 233
<211> LENGTH: 21
<212> TYPE: RNA
<213> ORGANISM: Artificial
<220> FEATURE:
<223> OTHER INFORMATION: siRNA

<400> SEQUENCE: 233
aaauccaaca aagucuggcu u                                             21

<210> SEQ ID NO 234
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_RNA
<222> LOCATION: (1)..(27)
<223> OTHER INFORMATION: bases 9, 11, 13, 15, 17, 19, 21, 23 and 25-27
      are 2' OMe derivatives

<400> SEQUENCE: 234
aauuucaaau ccaacaaagu cuggcuu                                       27
```